(12) United States Patent
Chu et al.

(10) Patent No.: US 11,566,067 B2
(45) Date of Patent: *Jan. 31, 2023

(54) METHODS OF LOWERING TRIGLYCERIDE LEVELS WITH AN ANGPTL8-BINDING ANTIBODY OR ANTIGEN-BINDING FRAGMENT THEREOF

(71) Applicant: NGM Biopharmaceuticals, Inc., South San Francisco, CA (US)

(72) Inventors: Chun Chu, Foster City, CA (US); Xunshan Ding, Millbrae, CA (US); Zhonghao Liu, Redwood City, CA (US); Yan Wang, Foster City, CA (US); Yiyuan Yin, Fremont, CA (US); Wenwu Zhai, Redwood City, CA (US)

(73) Assignee: NGM Biopharmaceuticals, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/996,623

(22) Filed: Aug. 18, 2020

(65) Prior Publication Data

US 2021/0095014 A1 Apr. 1, 2021

Related U.S. Application Data

(63) Continuation of application No. 16/184,548, filed on Nov. 8, 2018, now Pat. No. 10,774,139.

(60) Provisional application No. 62/584,637, filed on Nov. 10, 2017.

(51) Int. Cl.

| | |
|---|---|
| *A61K 39/395* | (2006.01) |
| *A61P 3/06* | (2006.01) |
| *C07K 16/22* | (2006.01) |
| *A61K 49/00* | (2006.01) |
| *A61K 47/68* | (2017.01) |
| *A61K 31/20* | (2006.01) |
| *A61K 31/455* | (2006.01) |
| *A61K 51/10* | (2006.01) |
| *C07K 14/475* | (2006.01) |
| *A61P 3/10* | (2006.01) |
| *A61K 45/06* | (2006.01) |
| *A61K 39/00* | (2006.01) |

(52) U.S. Cl.
CPC .............. *C07K 16/22* (2013.01); *A61K 31/20* (2013.01); *A61K 31/455* (2013.01); *A61K 39/395* (2013.01); *A61K 39/3955* (2013.01); *A61K 47/6845* (2017.08); *A61K 49/0058* (2013.01); *A61K 51/1021* (2013.01); *A61P 3/06* (2018.01); *A61K 45/06* (2013.01); *A61K 2039/505* (2013.01); *A61P 3/10* (2018.01); *C07K 14/475* (2013.01); *C07K 2317/21* (2013.01); *C07K 2317/24* (2013.01); *C07K 2317/34* (2013.01); *C07K 2317/565* (2013.01); *C07K 2317/567* (2013.01); *C07K 2317/76* (2013.01); *C07K 2317/92* (2013.01)

(58) Field of Classification Search
CPC ....... C07K 16/22; A61K 39/3955; A61P 3/10; A61P 3/06
See application file for complete search history.

(56) References Cited

U.S. PATENT DOCUMENTS

| | | |
|---|---|---|
| 10,071,139 B2 | 9/2018 | Liu et al. |
| 10,702,587 B2 | 7/2020 | Liu et al. |
| 10,774,139 B2 | 9/2020 | Chu et al. |
| 2005/0100991 A1 | 5/2005 | Rosen |
| 2014/0179596 A1 | 6/2014 | Rosen et al. |
| 2014/0219956 A1 | 8/2014 | Govindan et al. |
| 2014/0303078 A1 | 10/2014 | Melton |
| 2016/0264662 A1 | 9/2016 | Dimitrov et al. |
| 2017/0037124 A1 | 2/2017 | Gusarova et al. |
| 2017/0143799 A1 | 5/2017 | Liu et al. |
| 2018/0134781 A1 | 5/2018 | Gusarova et al. |
| 2019/0060408 A1 | 2/2019 | Liu et al. |
| 2019/0169281 A1 | 6/2019 | Chu et al. |
| 2021/0015902 A1 | 1/2021 | Liu et al. |

FOREIGN PATENT DOCUMENTS

| | | |
|---|---|---|
| JP | 2014523871 | 9/2014 |
| WO | WO 2011/084714 | 7/2011 |
| WO | WO 2012/167744 | 12/2012 |
| WO | WO 2012/170977 | 12/2012 |
| WO | WO 2014/110368 | 7/2014 |
| WO | WO 2016/054494 | 4/2016 |
| WO | WO 2016/122701 | 8/2016 |
| WO | WO 2017/027316 | 2/2017 |
| WO | WO 2017/177181 | 10/2017 |
| WO | WO 2019/094533 | 5/2019 |

OTHER PUBLICATIONS

Abu-Farha et al., "ANGPTL8 (betatrophin) role in diabetes and metabolic diseases," Diabetes Metab. Res. Rev., 2017, 8 pages.
Anonymous: "UPI0001 D3DA7B", Jul. 27, 2011 {Jul. 27, 2011), XP0554.54807, Retrieved from the Internet: URL:http://www.uniprot.org/uniparc/UPI0001D3DA7B [retrieved on Jul. 27, 2011], 1 page.
Chi et al., "ANGPTL8 promotes the ability of ANGPTL3 to bind and inhibit lipoprotein lipase," Molecular Metabolism, 2017, 6:1137-1149.
Dewey et al.. "Genetic and Pharmacologic Inactivation of ANGPTL3 and Cardiovascular Disease," The New England Journal Of Medicine. Jun. 2017, 11 pages.

(Continued)

*Primary Examiner* — Zachary C Howard
(74) *Attorney, Agent, or Firm* — Fish & Richardson P.C.

(57) ABSTRACT

The present disclosure provides binding agents, such as antibodies, that specifically bind Angiopoietin-like protein 8 (ANGPTL8), including human ANGPTL8, and methods of their use.

38 Claims, 8 Drawing Sheets

Specification includes a Sequence Listing.

(56) References Cited

OTHER PUBLICATIONS

Fu et al., "A lipasin/Angptl8 monoclonal antibody lowers mouse serum triglycerides involving increased postprandial activity of the cardiac lipoprotein lipase," Scientific Reports, 2015, 9 pages.
Fu et al., "Elevated circulating lipasin/betatrophin in human type 2 diabetes and obesity." Scientific Reports, 4:5013, 5 pages.
Fu et al., "Supplemental Materials: A lipasin/Angptl8 monoclonal antibody lowers mouse serum triglycerides involving increased postprandial activity of the cardiac lipoprotein lipase," Scientific Reports, 2015, 3 pages.
Gusarova et al., "ANGPTL8 Blockade With a Monoclonal Antibody Promotes Triglyceride Clearance, Energy Expenditure, and Weight Loss in Mice," Endocrinology, May 2017, 158(5):1252-1259.
Gusarova et al., "ANGPTL8/betatrophin does not control pancreatic beta cell expansion"; Cell, 2014, 159 (3):691-696.
Haller et al., "ANGPTL8 requires ANGPTL3 to inhibit lipoprotein lipase and plasma triglyceride clearance," Journal of Lipid Research, 2017, 58: 1166-1173.
Kersten, "Physiological regulation of lipoprotein lipase," Biochimica et Biophysica Acta, Jul. 2014, 1841(7):919-933.
Lee et at. "Association between betatrophin/ANGPTL8 and non-alcoholic fatty liver disease: animal and human studies," Nature Scientific Reports, 2016, 6(1):1-12.
Lonardo et al., "Nonalcoholic fatty liver disease: Evolving paradigms," World J. Gastroenterol, Sep. 2017, 23(36):6571-6592.
Masana, "Pitavastatin in cardiometabolic disease: therapeutic profile." Cardiovascular Diabetology, 2013, 8 pages.
Mattijssen & Kersten, "Regulation of triglyceride metabolism by Angiopoietin-like proteins," Biochimica et Biophysica Acta, 2012, 782-789.
Mele et al., "Circulating angiopoietin-like 8 (ANGPTL8) is a marker of liver steatosis and is negatively regulated by Prader-Willi Syndrome." Scientific Reports, 2017, 7 pages.
Oh et al., "Management of Hypertriglyceridemia," American Family Physician, 2017, 75(9), 7 pages.
Pascual-Corrales et al., "Circulating ANGPTL8/Betatrophin Concentrations Are Increased After Surgically Induced Weight Loss, but Not After Diet-Induced Weight Loss," Obesity Surgery, 2016, 1881-1889.
PCT International Search Report and Written Opinion in Appln. No. PCT/US15/53700, dated Jan. 7, 2016, 12 pages.
PCT International Search Report and Written Opinion in Appln No. PCT/US2018/059734, dated Mar. 22, 2019, 11 pages.
Quagliarini et al., "Atypical angiopoietin-like protein that regulates ANGPTL3." PNAS. Nov. 2012, 109(48): 19751-19756.
Saku et al., "Randomized Head-to-Head Comparison of Pitavastatin, Atorvastatin, and Rosuvastatin for Safety and Efficacy (Quantity and Quality of LDL)," Circulation Journal., 2011, 75:1493-1505.
Santulli G, "Angiopoietin-like proteins: a comprehensive look," Frontiers in Endocrinology, 2014, 5:1-6.
Siddiqa et al., "Structural characterization of ANGPTL8 (betatrophin) with its interacting partner lipoprotein lipase," Computational Bioiogv and Chemistry, 2016, 61:210-220.
Tseng et al., "Emerging Regulation and Function of Betatrophin." International Journal of Molecular Sciences, 2014, 15:23640-23657.

Wang et al., "Mice lacking ANGPTL8 (Betatrophin) manifest disrupted triglyceride metabolism without impaired glucose homeostasis," PNAS, 2013, 110(40):16109-16114.
Wang et al., "Dysglycemia and Dyslipidemia Models in Nonhuman Primates: Part II. Model of Naturally Occurring or Experimental Obesity," Journal of Diabetes & Metabolism, 2016, 7(1):1000641, 11 pages.
Wang et al., "Mice lacking ANGPTL8 (Betatrophin) manifest disrupted triglyceride metabolism without impaired glucose homeostasis." PNAS. Oct. 2013. 110(40):16109-16114.
Wang et al., "The Effects of Serum ANGPTL8/ betatrophin on the Risk of Developing the Metabolic Syndrome—A Prospective Study," Nature, Jun. 2016, 6:28431, 8 pages.
Yi et al., "RETRACTED: Betatrophin: A Hormone that Controls Pancreatic β Cell Proliferation." 2013, 747-758.
Yi et al., "Retraction Notice to: Betatrophin: A Hormone tliat Controls Pancreatic β Cell Proliferation" Cell, 168(1 -2):326.
Yi et al., "Supplemental Material: Betatrophin: a hormone that controls pancreatic β cell proliferation," 2013, 10 pages.
Yi et al., "Betatrophin: A Hormone tliat Controls Pancreatic β Cell Proliferation" Cell, 153 (4):747-58.
Yuan et al., "Hypertriglyceridemia: its etiology, effects and treatment," CMAJ, Apr. 2007, 176(8) 1113-1120.
Zhang et al., "Angiopoietin-like protein 8 (betatrophin) is a stress-response protein that down-regulates expression of adipocyte triglyceride lipase," Biochimica el Biophysica Acta, 2016, 130-137.
Zhang et al., "Emerging roles of Lipasin as a critical lipid regulator", Biochemical and Biophysical Research Communications, Feb. 2013, 432(3):401-405.
Zhang et al., "A dual role of lipasin (betatrophin) in lipid metabolism and glucose homeostasis: consensus and controversy." Cardiovascular Diabetology, 2014,13:133.
U.S. Appl. No. 16/184,548, 2019/0169281, U.S. Pat. No. 10,774,139, filed Nov. 8, 2018, Chun Chu.
U.S. Appl. No. 16/056,068, 2019/0060408, U.S. Pat. No. 10,702,587, filed Aug. 6, 2018, Zhonghao Liu.
U.S. Appl. No. 15/318,937, 2017/0143799, U.S. Pat. No. 10,071,139, filed Dec. 14, 2016, Zhonghao Liu.
U.S. Appl. No. 16/888,249, 2021/0015902, filed May 29, 2020, Zhonghao Liu.
U.S. Appl. No. 16/888,249, filed May 29, 2020, Zhonghao Liu.
EP Partial Supplementary European Search Report in European Appln. No. 18877271.9, dated Jun. 30, 2021, 16 pages.
Zhang et al., "OR13-6: A Monoclonal Neutralizing Antibody Against Lipasin (Angptl8), a Novel Lipid Regulator, Reduces Serum Triglycerides in Mice By Enhancing Lipoprotein Lipase-Mediated Triglyceride Clearance," Endocrine Society's 97th Annual Meeting and Expo, Mar. 5-8, 2015, San Diego, 2 pages, Abstract.
Extended European Search Report in European Appln. No. 18877271. 9, dated Sep. 29, 2021, 19 pages.
Rudikoff et al., "Single amino acid substitution altering antigen-binding specificity," Proceedings of the National Academy of Sciences, Mar. 1, 1982, 79(6):1979-83.
EP Extended European Search Report in European Appln. No. 15848061.6, dated Apr. 25, 2018, 12 pages.
Extended European Search Report in European Appln. No. 20185093. 0, dated Apr. 20, 2021, 9 pages.

FIG. 1A

Heavy chain variable region sequence alignments

```
Kabat      1 ----10          22        31----35         40   50-a----60---65
AbM        1 ----10          22    26----35             40   50-a----58      65
Chothia    1 ----10          22    26----32             40        a-55       65
Contact    1 ----10          22       30----35          40        a----58    65
IMGT       1 ----10          23    27----38  41         40              56----65  74
AHon       1 ----10          23          27     42                         57      76

1E5        QVQLQQSGAELVRPGTSVRLSCKAS GYTFTDYTIH WVKLRSGQGLEWIG WFYPGSDNIKYNAKFKD
1E9        QVQLQQSGTELVRPGASVKLSCKAS GYTFTDYTIH WVKQRSGQGLEWIG WFYPGSDNIKFNAKFRD
1A8        QVQLQQSGAELVRPGASVKLSCKAS GYTFTDYTIH WVKQRSGQGLEWIG WFYPGSDNIKYNEKFRD
Consensus                            GYTFTDYTIH                 WFYPGSDNIKXNXKFXD
                                    (SEQ ID NO:11)              (SEQ ID NO:59)

Kabat       70      80 abc         90   95----------102          110
AbM         70      80 abc         90   95----------102          110
Chothia     70      80 abc         90      96--------101         110
Contact     70      80 abc         90   93----------101          110
IMGT    75          89             105----------------117        138
AHon                                                109

1E5        KATLTADKSSTVYMDLGRLTSEDSAVYFCAR HEAFSYYDVAWFAY WGQGTLVTVSA (SEQ ID NO:35)
1E9        KATLTADKSSTVYMELSRLTSEDSAVYFCAR HEAFYYVDVAWFAN WGQGTLVTVST (SEQ ID NO:44)
1A8        KATLTADKSSSIVVMELSRLTSEDSAVYFCAR HEAYYYVDVAWFAY WGQGTLVTVSA (SEQ ID NO:56)
Consensus                                  HEAXXXYDVAWFAX
                                          (SEQ ID NO:59)
```

FIG. 1B

Light chain variable region sequence alignments

```
Kabat       1          10         20         24-27--------34         40                    50-----56
AbM         1          10         20         24-----30-----34        40                    50-----56
Chothia     1          10         20         26---------32           40                    50---
Contact     1          10         20                  30---------36  40           46-------55
IMGT        1                                27--------------38  41                56-65  69
                       23                                                          |   |
AHon        1                                                                      58     72
                       23                                          42

1E5      DVVMTQTPLSLPVSLGDQASISC RSSQSLVHSNGNTYLH WYLQKPGQSPKLLIY TVSNRFS
1E9      DVVMTQTPLSLPVSLGDQASISC RSSQSLVHSNGNTYLH WFLQKPGQSPNLLIY TVSNRFS
1A8      DVVMTQTPLSLPVSLGDQASISC SSSQSLVHSNGNTFLH WFLQRPGQSPKLLIY TVSNRFS
Consensus                        XSSQSLVHSNGNTXLH                  TVSNRFS
                                  (SEQ ID NO:60)                    (SEQ ID NO:29)

Kabat      60         70         80         89-------97
AbM        60         70         80         89-------97
Chothia    60         70         80                   91----96
Contact    60         70         80         89-------96
IMGT                  70                                         105--------117       (SEQ ID NO:36)
                      89                                                              (SEQ ID NO:45)
AHon                  73         91                              107       138        (SEQ ID NO:57)

1E5      GVPDRFSGSGSGSDFTLNFSRVEAEDLGVYFC SQTTHFPYT FGGGTKLEIK (SEQ ID NO:36)
1E9      GVPDRFSGSGSGSGTDFTLKISRVEAGDLGVYFC SQSTHFPYT FGGGTKLEIK (SEQ ID NO:45)
1A8      GVPDRFSGSGSGTDFTLKISRVEAEDLGVYFC SQSTHFPYT FGGGTTLEIK (SEQ ID NO:57)
Consensus                                 SQXTHFPYT
                                          (SEQ ID NO:61)
```

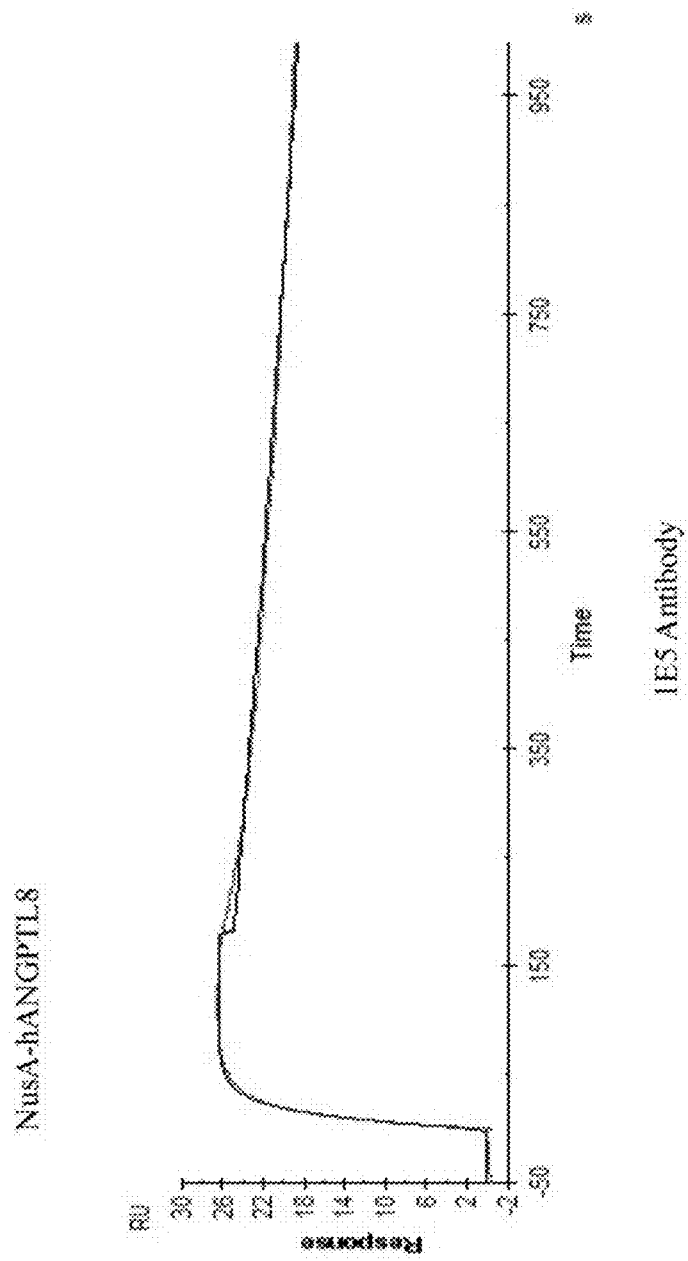

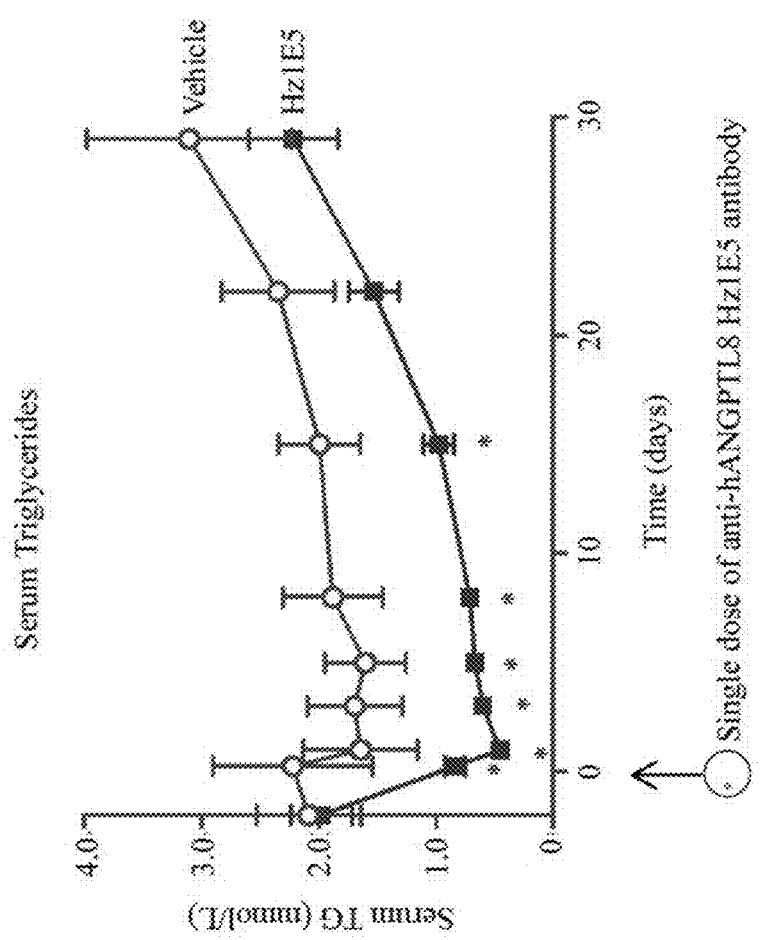

METHODS OF LOWERING TRIGLYCERIDE LEVELS WITH AN ANGPTL8-BINDING ANTIBODY OR ANTIGEN-BINDING FRAGMENT THEREOF

CROSS-REFERENCE TO RELATED APPLICATIONS

This application is a continuation of U.S. application Ser. No. 16/184,548, filed Nov. 8, 2018, issued as U.S. Pat. No. 10,774,139, which claims the benefit of priority to U.S. Ser. Application No. 62/584,637 filed Nov. 10, 2017, the contents of both applications are hereby incorporated herein by reference in its entirety.

SEQUENCE LISTING

The instant application contains a Sequence Listing which has been submitted electronically in ASCII format and is hereby incorporated by reference in its entirety. Said ASCII copy, created on Aug. 17, 2020, is named 47702-0010002_SEQ.txt, and is 40 KB in size.

FIELD OF THE INVENTION

The present disclosure generally relates to agents that bind angiopoietin-like protein 8 (ANGPTL8), particularly antibodies that bind human ANGPTL8, as well as therapeutic methods of using the agents.

BACKGROUND

Angiopoietin-like protein 8 (ANGPTL8) is an ANGPTL family member that has been implicated in both triglyceride and glucose metabolism. ANGPTL8 is also referred to in the literature as betatrophin, lipasin, TD26, RIFL (refeeding-induced fat and liver protein), and C19orf80. ANGPTL8 is produced by the liver and in white adipose tissue and circulates in the blood. ANGPTL8 is considered a mediator of post-prandial trafficking of fatty acids to adipose tissue and a regulator of postprandial glucose metabolism, but its mechanism of action remains unclear. Overexpression of ANGPTL8 has been associated with elevated triglyceride levels. (See, e.g., Santulli G, 2014, *Frontiers in Endocrinology*, 5:1-6; Zhang R and Abou-Samra A B, 2014, *Cardiovascular Diabetology*, 13:133).

Elevated blood triglyceride levels and hypertriglyceridemia are significant contributing factors to cardiovascular diseases. Elevated triglyceride levels can also be a sign of, and contributing factor to, conditions that increase a person's overall risk of heart disease, these conditions may include obesity, metabolic syndrome, excess body fat, high blood pressure, high blood sugar, and abnormal cholesterol levels. In addition, high triglyceride levels also contribute to decreased health status in subjects with poorly controlled type 2 diabetes, hypothyroidism, liver disease, kidney disease, and genetic metabolic disorders. Further complicating treatment for associated conditions, elevated triglyceride levels are a common side effect of routinely prescribed medications such as beta blockers, birth control, diuretics, steroids, and certain cancer treatments, such as tamoxifen.

Although there are therapeutics available that may reduce elevated triglyceride levels in a subject, there is a need for new agents that effectively reduce elevated triglyceride levels. In addition, there is a need for agents that may be used in methods of treatment for a variety of diseases and disorders associated with elevated triglycerides levels, high LDL-cholesterol levels, and/or low HDL-cholesterol levels.

BRIEF SUMMARY

The present disclosure provides agents that bind to and/or interact with ANGPTL8. The agents may include, but are not limited to, polypeptides such as antibodies that specifically bind ANGPTL8. Such agents may bind ANGPTL8, an ANGPTL8 fragment, an ANGPTL8 peptide, and/or an ANGPTL8 epitope. These agents may be referred to herein as "ANGPTL8-binding agents." In some embodiments, the agent is an ANGPTL8 antagonist. In some embodiments, the agent is an ANGPTL8 agonist. The disclosure provides methods of using the agents. In some embodiments, the agents are used for lowering triglyceride levels. In some embodiments, the agents are used for treating a disease or disorder associated with elevated triglyceride levels. In some embodiments, the disease or disorder includes, but is not limited to, hypertriglyceridemia, metabolic syndrome, atherosclerosis, obesity, diabetes, hypothyroidism, acute pancreatitis, liver disease, or kidney disease. In some embodiments, the agents are used for increasing HDL-cholesterol levels. In some embodiments, the agents are used for lowering LDL-cholesterol levels. In some embodiments, the agents are used in combination with at least one additional therapeutic agent.

The disclosure also provides compositions, such as pharmaceutical compositions, comprising the agents described herein. Polynucleotides and/or vectors encoding the agents and methods of making the agents are also provided. Cells comprising or producing the agents described herein are provided as well as cells comprising the polynucleotides and/or the vectors described herein.

In one aspect, the present disclosure provides agents that bind ANGPTL8. In some embodiments, the agent binds human ANGPTL8. In some embodiments, the agent binds cynomolgus monkey ("cyno") ANGPTL8. In some embodiments, the agent binds human ANGPTL8 and cyno ANGPTL8. In some embodiments, the agent is an antibody. In some embodiments, the agent is an antibody that binds human ANGPTL8. In some embodiments, the agent is an antibody that binds cyno ANGPTL8. In some embodiments, the agent is an antibody that binds human ANGPTL8 and cyno ANGPTL8. In some embodiments, the agent is an antibody that binds human ANGPTL8 and does not bind mouse ANGPTL8.

In some embodiments, an antibody or antigen-binding fragment thereof specifically binds an N-terminal region of human ANGPTL8, wherein the N-terminal region comprises amino acids 25-60 of SEQ ID NO:1 and wherein the antibody (i) lowers triglyceride levels, (ii) lowers LDL-cholesterol, and/or (iii) increases HDL-cholesterol in a subject. In some embodiments, an antibody or antigen-binding fragment thereof specifically binds human ANGPTL8 and comprises: (a) a heavy chain CDR1 comprising GYTFTDYTIH (SEQ ID NO:11); a heavy chain CDR2 comprising WFYPGSDNIKX$_1$NX$_2$KFX$_3$D, wherein X$_1$ is Y or F, X$_2$ is A or E and X$_3$ is K or R (SEQ ID NO:58); and a heavy chain CDR3 comprising HEAX$_1$X$_2$X$_3$YDVAWFAX$_4$, wherein X$_1$ is F or Y, X$_2$ is S or Y, X$_3$ is Y or V, and X$_4$ is Y or N (SEQ ID NO:59); and/or (b) a light chain CDR1 comprising X$_1$SQSLVHSNGNTX$_2$LH, wherein X$_1$ is R or S and X$_2$ is Y or F (SEQ ID NO:60); a light chain CDR2 comprising TVSNRFS (SEQ ID NO:29); and a light chain CDR3 comprising SQX$_1$THFPYT, wherein X$_1$ is T or S (SEQ ID NO:61). In some embodiments, the antibody or antigen-binding fragment thereof comprises: (a) a heavy chain CDR1 comprising SEQ ID NOs:11, 12, 13, 14, or 15, a heavy chain CDR2 comprising SEQ ID NOs:16, 17, 18, 19, or 20, and a heavy chain CDR3 comprising SEQ ID NOs:21, 22, 23, or 24, and (b) a light chain CDR1 comprising SEQ ID NOs:25, 26, 27, or 28, a light chain CDR2 comprising SEQ ID NOs:29, 30, or 31, and a light chain CDR3 comprising SEQ ID NOs:32, 33, or 34. In some embodiments, the antibody or antigen-binding fragment thereof comprises: (a) a heavy chain CDR1 comprising SEQ ID NOs:11, 12, 13, 14, or 15, a heavy chain CDR2 comprising SEQ ID NOs:37, 17, 18, 19, or 20, and a heavy chain CDR3 comprising SEQ ID NOs:38, 39, 68, or 69, and (b) a light chain CDR1 comprising SEQ ID NOs:25, 26, 27, or 40, a light chain CDR2 comprising SEQ ID NOs:29, 30, or 31, and a light chain CDR3 comprising SEQ ID NOs:41, 42, or 43. In some embodiments, the antibody or antigen-binding fragment thereof comprises: (a) a heavy chain CDR1 comprising SEQ ID NOs:11, 12, 13, 14, or 15, a heavy chain CDR2 comprising SEQ ID NOs:46, 17, 18, 47, or 20, and a heavy chain CDR3 comprising SEQ ID NOs:48, 49, 50, or 51, and (b) a light chain CDR1 comprising SEQ ID NOs:52, 53, 54, or 55, a light chain CDR2 comprising SEQ ID NOs:29, 30, or 31, and a light chain CDR3 comprising SEQ ID NOs:41, 42, or 43. In some embodiments, the antibody or antigen-binding fragment thereof further comprises (a) a heavy chain FR1, a heavy chain FR2, a heavy chain FR3, and a heavy chain FR4; and/or (b) a light chain FR1, a light chain FR2, a light chain FR3, and a light chain FR4.

In some embodiments, an antibody or antigen-binding fragment thereof, comprises: (a) a heavy chain variable region having at least 90% sequence identity to SEQ ID NOs:35, 44, 56, or 62; and/or (b) a light chain variable region having at least 90% sequence identity to SEQ ID NOs:36, 45, 57, or 63. In some embodiments, an antibody or antigen-binding fragment thereof, comprises a heavy chain variable region having at least 95% sequence identity to SEQ ID NO:35 and a light chain variable region having at least 95% sequence identity to SEQ ID NO:36. In some embodiments, an antibody or antigen-binding fragment thereof, comprises a heavy chain variable region having at least 95% sequence identity to SEQ ID NO:44 and a light chain variable region having at least 95% sequence identity to SEQ ID NO:45. In some embodiments, an antibody or antigen-binding fragment thereof, comprises a heavy chain variable region having at least 95% sequence identity to SEQ ID NO:56 and a light chain variable region having at least 95% sequence identity to SEQ ID NO:57. In some embodiments, an antibody or antigen-binding fragment thereof, comprises a heavy chain variable region having at least 95% sequence identity to SEQ ID NO:62 and a light chain variable region having at least 95% sequence identity to SEQ ID NO:63. In some embodiments, an antibody or antigen-binding fragment thereof, comprises a heavy chain variable region comprising SEQ ID NO:35, and a light chain variable region comprising SEQ ID NO:36. In some embodiments, an antibody or antigen-binding fragment thereof, comprises a heavy chain variable region comprising SEQ ID NO:44 and a light chain variable region comprising SEQ ID NO:45. In some embodiments, an antibody or antigen-binding fragment thereof, comprises a heavy chain variable region comprising SEQ ID NO:56 and a light chain variable region comprising SEQ ID NO:57. In some embodiments, an antibody or antigen-binding fragment thereof of comprises a heavy chain variable region comprising SEQ ID NO:62 and a light chain variable region comprising SEQ ID NO:63.

In some embodiments, an antibody or antigen-binding fragment thereof that specifically binds ANGPTL8 comprises the heavy chain CDR1, CDR2, and CDR3, and/or the light chain CDR1, CDR2, and CDR3 from: (a) the antibody designated 1E5 that comprises a heavy chain variable region comprising SEQ ID NO:35 and a light chain variable region comprising SEQ ID NO:36; (b) the antibody designated Hz1E5 that comprises a heavy chain variable region comprising SEQ ID NO:62 and a light chain variable region comprising SEQ ID NO:63; (c) the antibody designated 1E9 that comprises a heavy chain variable region comprising SEQ ID NO:44 and a light chain variable region comprising SEQ ID NO:45; or (d) the antibody designated 1A8 that comprises a heavy chain variable region comprising SEQ ID NO:56 and a light chain variable region comprising SEQ ID NO:57. In some embodiments, the antibody or antigen-binding fragment thereof, comprises the CDR1, CDR2, and CDR3 from a heavy chain variable region comprising SEQ ID NO:35 and the CDR1, CDR2, and CDR3 from a light chain variable region comprising SEQ ID NO:36. In some embodiments, the antibody or antigen-binding fragment thereof, comprises the CDR1, CDR2, and CDR3 from a heavy chain variable region comprising SEQ ID NO:62 and the CDR1, CDR2, and CDR3 from a light chain variable region comprising SEQ ID NO:63. In some embodiments, the antibody or antigen-binding fragment thereof, comprises the CDR1, CDR2, and CDR3 from a heavy chain variable region comprising SEQ ID NO:44 and the CDR1, CDR2, and CDR3 from a light chain variable region comprising SEQ ID NO:45. In some embodiments, the antibody or antigen-binding fragment thereof, comprises the CDR1, CDR2, and CDR3 from a heavy chain variable region comprising SEQ ID NO:56 and the CDR1, CDR2, and CDR3 from a light chain variable region comprising SEQ ID NO:57.

In some embodiments, an antibody or antigen-binding fragment thereof that specifically binds ANGPTL8 comprises: (a) a heavy chain variable region comprising a CDR1, a CDR2, and a CDR3 amino acid sequence depicted in Tables 1-3; and/or (b) a light chain variable region comprising a CDR1, a CDR2, and a CDR3 amino acid sequence depicted in Tables 1-3.

In some embodiments, an antibody that specifically binds ANGPTL8 comprises a heavy chain of SEQ ID NO:64 and/or a light chain of SEQ ID NO:65.

In another aspect of the disclosure, an antibody or antigen-binding fragment thereof competes for binding to ANGPTL8 with a reference antibody, wherein the reference antibody comprises: (a) a heavy chain CDR1 comprising GYTFTDYTIH (SEQ ID NO:11); a heavy chain CDR2 comprising WFYPGSDNIKX$_1$NX$_2$KFX$_3$D, wherein X$_1$ is Y or F, X$_2$ is A or E and X$_3$ is K or R (SEQ ID NO:58); and a heavy chain CDR3 comprising HEAX$_1$X$_2$X$_3$YDVAWFAX$_4$, wherein X$_1$ is F or Y, X$_2$ is S or Y, X$_3$ is Y or V, and X$_4$ is Y or N (SEQ ID NO:59); and/or (b) a light chain CDR1 comprising X$_1$SSQSLVHSNGNTX$_2$LH, wherein X$_1$ is R or S and X$_2$ is Y or F (SEQ ID NO:60); a light chain CDR2 comprising TVSNRFS (SEQ ID NO:29); and a light chain CDR3 comprising SQX$_1$THFPYT, wherein X$_1$ is T or S (SEQ ID NO:61). In some embodiments, an antibody or antigen-binding fragment thereof binds an epitope on ANGPTL8 recognized by a reference antibody, wherein the reference antibody comprises: (a) a heavy chain CDR1 comprising GYTFTDYTIH (SEQ ID NO:11); a heavy chain CDR2 comprising WFYPGSDNIKX$_1$NX$_2$KFX$_3$D, wherein X$_1$ is Y or F, X$_2$ is A or E and X$_3$ is K or R (SEQ ID NO:58); and a heavy chain CDR3 comprising HEAX$_1$X$_2$X$_3$YDVAWFAX$_4$, wherein X$_1$ is F or Y, X$_2$ is S or Y, X$_3$ is Y or V, and X$_4$ is Y or N (SEQ ID NO:59); and/or (b) a light chain CDR1 comprising XISSQSLVHSNGNTX$_2$LH, wherein X$_1$ is R or S and X$_2$ is Y or F (SEQ ID NO:60); a light chain CDR2 comprising TVSNRFS (SEQ ID NO:29); and a light chain CDR3 comprising SQX$_1$THFPYT, wherein X$_1$ is T or S (SEQ ID NO:61). In some embodiments, the reference antibody further comprises (a) a heavy chain variable region FR1, a heavy chain variable region FR2, a heavy chain variable region FR3, and a heavy chain variable region FR4, and (b) a light chain variable region FR1, a light chain variable region FR2, a light chain variable region FR3, and a light chain variable region FR4.

In some embodiments, the reference antibody comprises: (a) a heavy chain CDR1 comprising SEQ ID NOs:11, 12, 13, 14, or 15, a heavy chain CDR2 comprising SEQ ID NOs:16, 17, 18, 19, or 20, and a heavy chain CDR3 comprising SEQ ID NOs:21, 22, 23, or 24, and (b) a light chain CDR1 comprising SEQ ID NOs:25, 26, 27, or 28, a light chain CDR2 comprising SEQ ID NOs:29, 30, or 31, and a light chain CDR3 comprising SEQ ID NOs:32, 33, or 34. In some embodiments, the reference antibody comprises: (a) a heavy chain CDR1 comprising SEQ ID NOs:11, 12, 13, 14, or 15, a heavy chain CDR2 comprising SEQ ID NOs:37, 17, 18, 19, or 20, and a heavy chain CDR3 comprising SEQ ID NOs:38, 39, 68, or 69, and (b) a light chain CDR1 comprising SEQ ID NOs:25, 26, 27, or 40, a light chain CDR2 comprising SEQ ID NOs:29, 30, or 31, and a light chain CDR3 comprising SEQ ID NOs:41, 42, or 43. In some embodiments, the reference antibody comprises: (a) a heavy chain CDR1 comprising SEQ ID NOs:11, 12, 13, 14, or 15, a heavy chain CDR2 comprising SEQ ID NOs:46, 17, 18, 47, or 20, and a heavy chain CDR3 comprising SEQ ID NOs:48, 49, 50, or 51, and (b) a light chain CDR1 comprising SEQ ID NOs:52, 53, 54, or 55, a light chain CDR2 comprising SEQ ID NOs:29, 30, or 31, and a light chain CDR3 comprising SEQ ID NOs:41, 42, or 43. In some embodiments, the reference antibody further comprises (a) a heavy chain variable region FR1, a heavy chain variable region FR2, a heavy chain variable region FR3, and a heavy chain variable region FR4, and (b) a light chain variable region FR1, a light chain variable region FR2, a light chain variable region FR3, and a light chain variable region FR4.

In some embodiments, the reference antibody comprises a heavy chain variable region comprising SEQ ID NOs:25, 44, 56, or 62; and a light chain variable region comprising SEQ ID NOs:26, 45, 57, or 63. In some embodiments, the reference antibody comprises a heavy chain variable region comprising SEQ ID NO:25 and a light chain variable region comprising SEQ ID NO:26. In some embodiments, the reference antibody comprises a heavy chain variable region comprising SEQ ID NO:44 and a light chain variable region comprising SEQ ID NO:45. In some embodiments, the reference antibody comprises a heavy chain variable region comprising SEQ ID NO:56 and a light chain variable region comprising SEQ ID NO:57. In some embodiments, the reference antibody comprises a heavy chain variable region comprising SEQ ID NO:62 and a light chain variable region comprising SEQ ID NO:63.

In some embodiments, the reference antibody binds an N-terminal region of ANGPTL8, wherein the N-terminal region comprises SEQ ID NO:3. In some embodiments, the reference antibody binds an N-terminal region of ANGPTL8, wherein the N-terminal region comprises SEQ ID NO:6. In some embodiments, the reference antibody binds an N-terminal region of ANGPTL8, wherein the N-terminal region comprises SEQ ID NO:7. In some embodiments, the reference antibody binds an N-terminal region of ANGPTL8, wherein the N-terminal region comprises SEQ ID NO:8.

In some embodiments of each of the aforementioned aspects and embodiments, as well as other aspects and embodiments described herein, the antibody is a monoclonal antibody. In some embodiments, the antibody is a humanized antibody. In some embodiments, the antibody is a human antibody. In some embodiments, the antibody is a human chimeric antibody. In some embodiments, the antibody or antibody fragment thereof is a Fab, Fab', F(ab')$_2$, Fv, scFv, (scFv)$_2$, single chain antibody, dual variable region antibody, single variable region antibody, linear antibody, a V region, a bispecific antibody, or a multispecific antibody.

In some embodiments of each of the aforementioned aspects and embodiments, as well as other aspects and embodiments described herein, an antibody or antigen-binding fragment thereof described herein is conjugated to a detectable marker. In some embodiments, the detectable marker is selected from a radioisotope, a metal chelator, an enzyme, a fluorescent compound, a bioluminescent compound, and a chemiluminescent compound.

In some embodiments, an antibody or antigen-binding fragment thereof described herein is conjugated to a cytotoxic agent.

In some embodiments of each of the aforementioned aspects and embodiments, as well as other aspects and embodiments described herein, an antibody or antigen-binding fragment thereof described herein is an antagonist of ANGPTL8. In some embodiments, the antibody or antigen-binding fragment thereof reduces or decreases ANGPTL8 levels. In some embodiments, the antibody or antigen-binding fragment thereof inhibits ANGPTL8 activity. In some embodiments, the antibody or antigen-binding fragment thereof modulates lipoprotein lipase (LPL) activity. In some embodiments, the antibody or antigen-binding fragment thereof increases or enhances LPL activity. In some embodiments, the antibody or antigen-binding fragment thereof lowers or reduces triglyceride levels. In some embodiments, the antibody or antigen-binding fragment thereof lowers or reduces LDL-cholesterol levels. In some embodiments, the antibody or antigen-binding fragment thereof increases HDL-cholesterol levels. In some embodiments, the antibody or antigen-binding fragment thereof lowers triglyceride levels and increases HDL-cholesterol levels.

In some embodiments of each of the aforementioned aspects and embodiments, as well as other aspects and embodiments described herein, an agent described herein specifically binds ANGPTL8 and (i) lowers triglyceride levels in a subject; (ii) increases HDL-cholesterol levels in a subject; and/or (iii) lowers LDL-cholesterol levels in a subject.

In another aspect, the disclosure provides compositions comprising an ANGPTL8-binding agent (e.g., an antibody or antigen-binding fragment thereof) described herein. Methods of using a composition comprising an ANGPTL8-binding agent (e.g., an antibody or antigen-binding fragment thereof) described herein are also provided.

In another aspect, the disclosure provides pharmaceutical compositions comprising an ANGPTL8-binding agent (e.g., an antibody or antigen-binding fragment thereof) described herein and a pharmaceutically acceptable carrier.

In some embodiments of each of the aforementioned aspects, as well as other aspects and/or embodiments described elsewhere herein, the ANGPTL8-binding agent (e.g., an antibody or antigen-binding fragment thereof) is isolated. In some embodiments, the ANGPTL8-binding agent (e.g., an antibody or antigen-binding fragment thereof) is substantially pure.

In another aspect, the disclosure provides polynucleotides comprising a polynucleotide that encodes an ANGPTL8-binding agent described herein. In some embodiments, the polynucleotide is isolated. In some embodiments, a vector comprises a polynucleotide that encodes an ANGPTL8-binding agent described herein. In some embodiments, an isolated cell comprises a polynucleotide that encodes an ANGPTL8-binding agent described herein. In some embodiments, an isolated cell comprises a vector comprising a polynucleotide that encodes an ANGPTL8-binding agent described herein. In some embodiments, the disclosure also provides cells comprising or producing an ANGPTL8-binding agent described herein. In some embodiments, the cell is a monoclonal cell line. In some embodiments, the cell is a hybridoma. In some embodiments, the cell produces an anti-ANGPTL8 antibody described herein. In some embodiments, a transgenic animal produces an ANGPTL8-binding agent described herein.

In another aspect, the disclosure provides a binding agent that binds to essentially the same epitope on ANGPTL8 as an antibody described herein. In some embodiments, the binding agent is a heterodimeric molecule comprising an anti-ANGPTL8 antibody or antigen-binding fragment thereof described herein. In some embodiments, the binding agent comprises a scaffold protein comprising one or more of the CDRs shown in Tables 1-3. In some embodiments, the binding agent competes with one or more of the anti-ANGPTL8 antibodies described herein for binding to ANGPTL8 in a competitive binding assay.

In another aspect, the disclosure provides methods of using the ANGPTL8-binding agents (e.g., an antibody or antigen-binding fragment thereof) described herein. In some embodiments, a method of lowering triglyceride levels in a subject with elevated triglyceride levels comprises administering to the subject a therapeutically effective amount of an ANGPTL8-binding agent (e.g., antibody or antigen-binding fragment thereof) described herein. In some embodiments, a method of treating a disease or disorder associated with elevated triglyceride levels in a subject comprises administering to the subject a therapeutically effective amount of an ANGPTL8-binding agent (e.g., antibody or antigen-binding fragment thereof) described herein. In some embodiments, the disease or disorder is metabolic syndrome, obesity, diabetes, atherosclerosis, cardiovascular disease, hyperlipidemia, hypertriglyceridemia, pancreatitis, renal disease, liver disease, or hypothyroidism. In some embodiments, the elevated triglyceride levels are elevated plasma triglyceride levels. Those of skill in the art generally consider a "normal" plasma triglyceride level to be less than 150 mg/dL. In some embodiments, the elevated plasma triglyceride level is 150 mg/dL or higher. In some embodiments, the elevated plasma triglyceride level is about 150 to about 200 mg/dL. In some embodiments, the elevated plasma triglyceride level is about 200 to about 500 mg/dL. In some embodiments, the elevated plasma triglyceride level is about 500 mg/dL or higher. In some embodiments, after administration of the ANGPTL8-binding agent to the subject, the elevated triglyceride level is reduced by at least 5%, by at least 10%, by about 10-15%, by about 10-20%, by about 20-30%, or by more than 25% as compared to triglyceride levels in the subject prior to the administration of the agent.

In some embodiments, a method of increasing HDL-cholesterol levels in a subject comprises administering to the subject a therapeutically effective amount of an ANGPTL8-binding agent (e.g., antibody or antigen-binding fragment thereof) described herein. In some embodiments, a method of reducing LDL-cholesterol levels in a subject comprises administering to the subject a therapeutically effective amount of an ANGPTL8-binding agent (e.g., antibody or antigen-binding fragment thereof) described herein.

In some embodiments of the methods described herein, the subject has metabolic syndrome, has been diagnosed with metabolic syndrome, has symptoms of metabolic syndrome, or is at risk for developing metabolic syndrome. In some embodiments, the subject has hyperlipidemia or dyslipidemia, has been diagnosed with hyperlipidemia or dyslipidemia, has symptoms of hyperlipidemia or dyslipidemia, or is at risk for developing hyperlipidemia or dyslipidemia. In some embodiments, the subject has cardiovascular disease, has been diagnosed with cardiovascular disease, has symptoms of cardiovascular disease, or is at risk for developing cardiovascular disease. In some embodiments, the subject has diabetes (e.g., type 2 diabetes), has been diagnosed with diabetes (e.g., type 2 diabetes), has symptoms of diabetes (e.g., type 2 diabetes), or is at risk for developing diabetes (e.g., type 2 diabetes). In some embodiments, the subject is overweight or obese or is at risk of becoming overweight or obese.

In some embodiments of the methods described herein, the subject is administered one or more additional therapeutic agents. In some embodiments, the additional therapeutic agent(s) is selected from the group consisting of: a fibrate, a statin, omega-3 fatty acids, and niacin.

Also disclosed herein is the use of an ANGPTL8-binding agent (e.g., antibody or antigen-binding fragment thereof) described herein in the manufacture of a medicament for lowering triglyceride levels. The use of an ANGPTL8-binding agent (e.g., antibody or antigen-binding fragment thereof) described herein in the manufacture of a medicament for treatment of a disease or disorder associated with elevated triglyceride levels. The use of an ANGPTL8-binding agent (e.g., antibody or antigen-binding fragment thereof) described herein in the manufacture of a medicament for increasing HDL-cholesterol levels. The use of an ANGPTL8-binding agent (e.g., antibody or antigen-binding fragment thereof) described herein in the manufacture of a medicament for lowering LDL-cholesterol levels.

In some embodiments of each of the aforementioned aspects and embodiments, as well as other aspects and embodiments described herein, the subject is human.

Where aspects or embodiments of the disclosure are described in terms of a Markush group or other grouping of alternatives, the present disclosure encompasses not only the entire group listed as a whole, but also each member of the group individually and all possible subgroups of the main group, and also the main group absent one or more of the group members. The present disclosure also envisages the explicit exclusion of one or more of any of the group members in the claimed disclosure.

BRIEF DESCRIPTION OF THE FIGURES

FIGS. 1A-1B. Amino acid sequence alignments for exemplary anti-ANGPTL8 antibodies. FIG. 1A. Heavy chain variable region sequence alignment with consensus CDR sequences. FIG. 1B. Light chain variable region sequence alignment with consensus CDR sequences.

FIG. 2A. Representative diagrams of the human ANGPTL8 deletion variants V2-V5. FIG. 2B. Plasma triglyceride levels in mice injected with rAAVs expressing human ANGPTL8, or one of variants V2, V3, V4, and V5. Control animals were injected with a control rAAV.

FIG. 4. Binding affinity measurement of 1E5 antibody to NusA-hANGPTL8 fusion protein.

FIG. 5A. Binding affinity measurements of chimeric 1E5 antibody and humanized antibody Hz1E5 to human SE1 peptide. FIG. 5B. Plasma triglyceride levels in mice injected with a rAAV expressing human ANGPTL8 and treated with anti-hANGPTL8 antibodies (i) parental 1E5 from hybridoma, (ii) chimeric antibody 1E5, or (iii) humanized antibody Hz1E5. Control animals were (i) injected with a rAAV expressing hANGPTL8 and treated with a control anti-KLH antibody, or (ii) injected with a rAAV expressing GFP.

FIG. 6A-6B. FIG. 6A. Plasma triglyceride levels in cynomolgus monkeys treated with anti-hANGPTL8 antibody Hz1E5 or a vehicle control. FIG. 6B. Plasma HDL-cholesterol levels in cynomolgus monkeys treated with anti-hANGPTL8 antibody Hz1E5 or a vehicle control.

DETAILED DESCRIPTION

Figure 2B:
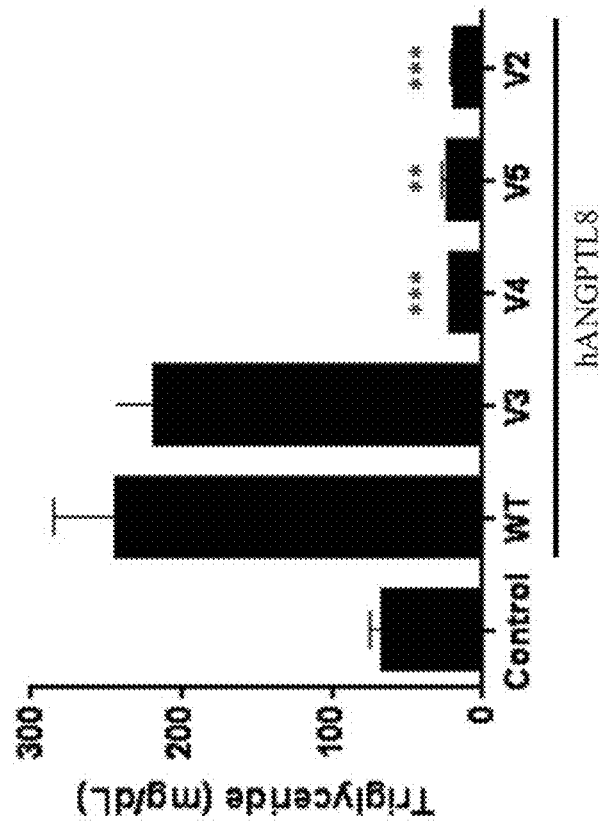
FIGS. 2A-2B.

The present disclosure provides novel agents, including but not limited to polypeptides such as antibodies, that bind ANGPTL8. The ANGPTL8-binding agents include, but are not limited to, polypeptides, antibodies, scaffold proteins, and heterodimeric molecules. ANGPTL8-binding agents include, but are not limited to, antagonists of ANGPTL8 activity and/or agents that modulate ANGPTL8 activity. Related polypeptides, polynucleotides, compositions comprising the agents, and methods of making the agents are also provided. Methods of using the novel agents, such as methods of treating an ANGPTL8-related disorder or disease are provided. Methods of lowering elevated triglyceride levels, of increasing HDL-cholesterol levels, and/or lowering LDL-cholesterol levels are also provided.

I. Definitions

Unless otherwise defined herein, technical and scientific terms used in the present description have the meanings that are commonly understood by those of ordinary skill in the art. For purposes of interpreting this specification, the following description of terms will apply and whenever appropriate, terms used in the singular will also include the plural and vice versa. In the event that any description of a term set forth conflicts with any document incorporated herein by reference, the description of the term set forth below shall control.

The term "binding agent" as used herein refers to a molecule which binds a specific antigen or target (e.g., ANGPTL8). A binding agent may comprise a protein, peptide, nucleic acid, carbohydrate, lipid, or small molecular weight compound. In some embodiments, a binding agent comprises an antibody or an antigen-binding fragment thereof. In some embodiments, a binding agent is an antibody or an antigen-binding fragment thereof. In some embodiments, a binding protein comprises an alternative protein scaffold or artificial scaffold and an antigen-binding site comprising CDRs or CDR derivatives. In some embodiments, a binding protein is a fusion protein comprising an antigen-binding site. In some embodiments, a binding protein is a bispecific or multispecific molecule comprising at least one antigen-binding site.

The term "antibody" as used herein refers to an immunoglobulin molecule that recognizes and binds a target through at least one antigen-binding site. "Antibody" is used herein in the broadest sense and encompasses various antibody structures, including but not limited to, polyclonal antibodies, recombinant antibodies, monoclonal antibodies, chimeric antibodies, humanized antibodies, human antibodies, bispecific antibodies, multispecific antibodies, diabodies, tribodies, tetrabodies, single chain Fv (scFv) antibodies, and antibody fragments as long as they exhibit the desired antigen-binding activity.

The term "intact antibody" or "full-length antibody" refers to an antibody having a structure substantially similar to a native antibody structure. This includes an antibody comprising two light chains each comprising a variable region and a light chain constant region (CL) and two heavy chains each comprising a variable region and at least heavy chain constant regions CH1, CH2, and CH3.

The term "antibody fragment" as used herein refers to a molecule other than an intact antibody that comprises a portion of an antibody and generally an antigen-binding site. Examples of antibody fragments include, but are not limited to, Fab, Fab', F(ab')2, Fv, disulfide-linked Fv (sdFv), Fd, linear antibodies, single chain antibody molecules (e.g., scFv), diabodies, tribodies, tetrabodies, minibodies, dual variable domain antibodies (DVD), single variable domain antibodies, and multispecific antibodies formed from antibody fragments.

The term "variable region" as used herein refers to the region of an antibody light chain or the region of an antibody heavy chain that is involved in binding the antibody to antigen. The variable region of an antibody heavy chain and an antibody light chain have similar structures, and generally comprise four framework regions and three complementarity determining regions (CDRs) (also known as hypervariable regions).

The term "framework region" refers to amino acid residues other than the CDR residues within a variable region. The framework region (FR) generally comprises four domains, FR1, FR2, FR3, and FR4.

The term "monoclonal antibody" as used herein refers to a substantially homogenous antibody population involved in the highly specific recognition and binding of a single antigenic determinant or epitope. The individual antibodies comprising the population are identical, except for possible naturally occurring mutations that may be present in minor amounts. The term "monoclonal antibody" encompasses intact and full-length monoclonal antibodies as well as antibody fragments (e.g., Fab, Fab', F(ab')2, Fv), single chain (scFv) antibodies, fusion proteins comprising an antibody fragment, and any other modified immunoglobulin molecule comprising an antigen-binding site. Furthermore, "monoclonal antibody" refers to such antibodies made by any number of techniques, including but not limited to, hybridoma production, phage library display, recombinant expression, and transgenic animals.

The term "chimeric antibody" refers to an antibody in which a portion of the heavy and/or light chain is derived from a particular source or species, while the remainder of the heavy and/or light chain is derived from a different source or species.

The term "humanized antibody" as used herein refers to a chimeric antibody that includes human immunoglobulins (e.g., recipient antibody) in which the native CDR residues are replaced by residues from corresponding CDRs from a nonhuman species (e.g., donor antibody) such as mouse, rat, rabbit, or nonhuman primate, wherein the donor antibody has the desired specificity, affinity, and/or activity. In some instances, one or more framework region residues of the human immunoglobulin are replaced by corresponding non-human residues. Furthermore, humanized antibodies can comprise residues that are not found in the recipient antibody or in the donor antibody. These modifications may be made to further refine and/or optimize antibody characteristics. A humanized antibody may comprise variable regions containing all or substantially all of the CDRs that correspond to those of a nonhuman immunoglobulin and all or substantially all of the framework regions that correspond to those of a human immunoglobulin. In some embodiments, the humanized antibody will comprise at least a portion of an immunoglobulin constant region (Fc), typically that of a human immunoglobulin.

The term "human antibody" as used herein refers to an antibody that possesses an amino acid sequence that corresponds to an antibody produced by a human and/or an antibody that has been made using any of the techniques that are known to those of skill in the art for making human antibodies. These techniques include, but not limited to, phage display libraries, yeast display libraries, transgenic animals, and B-cell hybridoma technology.

The terms "epitope" and "antigenic determinant" are used interchangeably herein and refer to that portion of an antigen or target capable of being recognized and bound by a particular antibody. When the antigen or target is a polypeptide, epitopes can be formed both from contiguous amino acids and noncontiguous amino acids juxtaposed by tertiary folding of the protein. Epitopes formed from contiguous amino acids (also referred to as linear epitopes) are typically retained upon protein denaturing, whereas epitopes formed by tertiary folding (also referred to as conformational epitopes) are typically lost upon protein denaturing. An epitope typically includes at least 3, and more usually, at least 5, 6, 7, or 8-10 amino acids in a unique spatial conformation. In some cases, X-ray crystallography is used to predict potential epitopes on a target protein. In some cases, X-ray crystallography is used to characterize an epitope on a target protein by analyzing the amino acid residue interactions of an antigen/antibody complex.

The term "specifically binds" as used herein refers to an agent (e.g., an antibody) that interacts more frequently, more rapidly, with greater duration, with greater affinity, or with some combination of the above to a particular antigen, epitope, protein, or target molecule than with alternative substances. In some embodiments, an agent (e.g., an antibody) that specifically binds an antigen (e.g., human ANGPTL8) may bind related antigens (e.g., cyno ANGPTL8). An antibody that specifically binds an antigen can be identified, for example, by immunoassays, ELISAs, BIACORE assays, or other techniques known to those of skill in the art.

The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification. Also included within the definition are, for example, polypeptides containing one or more analogs of an amino acid, including but not limited to, unnatural amino acids, as well as other modifications known in the art. It is understood that, because the polypeptides of this disclosure may be based upon antibodies, the term "polypeptide" encompasses polypeptides as a single chain and polypeptides of two or more associated chains.

The terms "polynucleotide" and "nucleic acid" and "nucleic acid molecule" are used interchangeably herein and refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software that may be used to obtain alignments of amino acid or nucleotide sequences are well-known in the art. These include, but are not limited to, BLAST, ALIGN, Megalign, BestFit, GCG Wisconsin Package, and variants thereof. In some embodiments, two nucleic acids or polypeptides of the disclosure are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the sequences that is at least about 10, at least about 20, at least about 40-60 nucleotides or amino acid residues, at least about 60-80 nucleotides or amino acid residues in length or any integral value there between. In some embodiments, identity exists over a longer region than 60-80 nucleotides or amino acid residues, such as at least about 80-100 nucleotides or amino acid residues, and in some embodiments the sequences are substantially identical over the full length of the sequences being compared, for example, (i) the coding region of a nucleotide sequence or (ii) an amino acid sequence.

The phrase "conservative amino acid substitution" as used herein refers to a substitution in which one amino acid residue is replaced with another amino acid residue having a similar side chain. Families of amino acid residues having similar side chains have been generally defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is considered to be a conservative substitution. Generally, conservative substitutions in the sequences of polypeptides and/or antibodies do not abrogate the binding of the polypeptide or antibody to the target binding site. Methods of identifying nucleotide and amino acid conservative substitutions that do not eliminate binding are well-known in the art.

The term "vector" as used herein means a construct, which is capable of delivering, and usually expressing, one or more gene(s) or sequence(s) of interest in a host cell. Examples of vectors include, but are not limited to, viral vectors, naked DNA or RNA expression vectors, plasmid, cosmid, or phage vectors, DNA or RNA expression vectors associated with cationic condensing agents, and DNA or RNA expression vectors encapsulated in liposomes.

The term "isolated" as used herein refers to a polypeptide, soluble protein, antibody, polynucleotide, vector, cell, or composition which is in a form not found in nature. An "isolated" antibody is substantially free of material from the cellular source from which it is derived. In some embodiments, isolated polypeptides, soluble proteins, antibodies, polynucleotides, vectors, cells, or compositions are those which have been purified to a degree that they are no longer in a form in which they are found in nature. In some embodiments, a polypeptide, soluble protein, antibody, polynucleotide, vector, cell, or composition which is isolated is substantially pure. A polypeptide, soluble protein, antibody, polynucleotide, vector, cell, or composition may be isolated from a natural source or from a source such as an engineered cell line.

The term "substantially pure" as used herein refers to material which is at least 50% pure (i.e., free from contaminants), at least 90% pure, at least 95% pure, at least 98% pure, or at least 99% pure.

The term "subject" refers to any animal (e.g., a mammal), including, but not limited to, humans, non-human primates, canines, felines, rabbits, rodents, and the like, which is to be the recipient of a treatment or therapy. Generally, the terms "subject" and "patient" are used interchangeably herein in reference to a human subject.

The term "pharmaceutically acceptable" as used herein refers to a substance approved or approvable by a regulatory agency or listed in the U.S. Pharmacopeia, European Pharmacopeia, or other generally recognized pharmacopeia for use in animals, including humans.

The terms "pharmaceutically acceptable excipient, carrier, or adjuvant" or "acceptable pharmaceutical carrier" as used herein refer to an excipient, carrier, or adjuvant that can be administered to a subject, together with at least one therapeutic agent (e.g., an antibody), and which does not destroy the pharmacological activity of the therapeutic agent. In general, those of skill in the art and the U.S. FDA consider a pharmaceutically acceptable excipient, carrier, or adjuvant to be an inactive ingredient of any formulation.

The term "pharmaceutical formulation" as used herein refers to a preparation which is in such form as to permit the biological activity of the agent (e.g., an antibody) to be effective. A pharmaceutical formulation generally comprises additional components, such as a pharmaceutically acceptable excipient, carrier, adjuvant, buffers, etc.

The term "effective amount" or "therapeutically effective amount" as used herein refers to the amount of an agent (e.g., an antibody) which is sufficient to reduce and/or ameliorate the severity and/or duration of a disease, disorder or condition and/or a symptom in a subject. The term also encompasses an amount of an agent necessary for the (i) reduction or amelioration of the advancement or progression of a given disease, disorder, or condition, (ii) reduction or amelioration of the recurrence, development, or onset of a given disease, disorder, or condition, and/or (iii) the improvement or enhancement of the prophylactic or therapeutic effect(s) of another agent or therapy (e.g., an agent other than the binding agents provided herein).

The term "therapeutic effect" as used herein refers to the effect and/or ability of an agent (e.g., an antibody) to reduce and/or ameliorate the severity and/or duration of a disease, disorder, or condition and/or a symptom in a subject. The term also encompasses the ability of an agent to (i) reduce or ameliorate the advancement or progression of a given disease, disorder, or condition, (ii) reduce or ameliorate the recurrence, development, or onset of a given disease, disorder, or condition, and/or (iii) to improve or enhance the prophylactic or therapeutic effect(s) of another agent or therapy (e.g., an agent other than the binding agents provided herein).

The term "treat" or "treatment" or "treating" or "to treat" or "alleviate" or "alleviation" or "alleviating" or "to alleviate" as used herein refers to both (1) therapeutic measures that aim to cure, slow down, lessen symptoms of, and/or halt progression of a pathologic condition or disorder and (2) prophylactic or preventative measures that aim to prevent or slow the development of a targeted pathologic condition or disorder. Thus, those in need of treatment include those already with the disorder, those at risk of having/developing the disorder, and those in whom the disorder is to be prevented.

The term "prevent" or "prevention" or "preventing" as used herein refers to the partial or total inhibition of the development, recurrence, onset, or spread of a disease, disorder, or condition, or a symptom thereof in a subject.

The term "prophylactic agent" as used herein refers to an agent that can partially or totally inhibit the development, recurrence, onset, or spread of a disease, disorder or condition, or a symptom thereof in a subject.

As used herein, reference to "about" or "approximately" a value or parameter includes (and describes) embodiments that are directed to that value or parameter. For example, a description referring to "about X" includes description of "X."

The phrase "substantially all" as used herein refers to at least about 60%, at least about 65%, at least about 70%, at least about 75%, at least about 80%, at least about 85%, at least about 90%, at least about 95%, at least about 96%, at least about 97%, at least about 98%, at least about 99%, or about 100%.

As used in the present disclosure and claims, the singular forms "a," "an" and "the" include plural forms unless the context clearly dictates otherwise.

It is understood that wherever embodiments are described herein with the term "comprising" otherwise analogous embodiments described in terms of "consisting of" and/or "consisting essentially of" are also provided. It is also understood that wherever embodiments are described herein with the phrase "consisting essentially of" otherwise analogous embodiments described in terms of "consisting of" are also provided.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. ANGPTL8-Binding Agents

Angiopoietin-like protein 8 (ANGPTL8) belongs to a family of proteins that is structurally similar to the angiopoietins, and are referred to as angiopoietin-like proteins or ANGPTLs. To date, the ANGPTL family includes eight proteins, ANGPTL1 to ANGPTL8. ANGPTL proteins have a similar biological structure and generally contain an amino-terminal coiled-coil domain, a linker region, and a carboxyl-terminal fibrinogen-like domain. In contrast to other members of the family, ANGPTL8 does not have a fibrinogen-like domain. The amino acid (aa) sequences for human ANGPTL8 (UniProtKB No. Q6UXH0), cynomolgus monkey ("cyno") ANGPTL8 (NCBI Ref. No. XP_005588064.1) and mouse ANGPTL8 (UniProtKB No. Q8R1L8) are provided herein as SEQ ID NO:1, SEQ ID NO:9, and SEQ ID NO:10, respectively. As used herein, reference to amino acid positions of ANGPTL8 refer to the numbering of amino acid sequences including the signal sequence.

The present disclosure provides agents that bind ANGPTL8. In some embodiments, the ANGPTL8-binding agent binds a fragment of ANGPTL8. In some embodiments, the ANGPTL8-binding agent binds within a specific region of ANGPTL8. In some embodiments, the ANGPTL8-binding agent binds an epitope on ANGPTL8. In some embodiments, the ANGPTL8-binding agent binds mouse ANGPTL8. In some embodiments, the ANGPTL8-binding agent binds human ANGPTL8. In some embodiments, the ANGPTL8-binding agent binds cyno ANGPTL8. In some embodiments, the ANGPTL8-binding agent binds human ANGPTL8 and cyno ANGPTL8.

In some embodiments, the ANGPTL8-binding agent binds within amino acids 22-83 of human ANGPTL8 and/or amino acids 22-83 of cyno ANGPTL8. In some embodiments, the ANGPTL8-binding agent binds within amino acids 84-138 of human ANGPTL8 and/or amino acids 84-138 of cyno ANGPTL8. In some embodiments, the ANGPTL8-binding agent binds within amino acids 139-198 of human ANGPTL8 and/or amino acids 139-198 of cyno ANGPTL8. In some embodiments, the ANGPTL8-binding agent binds within amino acids 25-60 of human ANGPTL8 and/or amino acids 25-60 of cyno ANGPTL8. In some embodiments, the ANGPTL8-binding agent binds within amino acids 22-46 of human ANGPTL8 and/or amino acids 22-46 of cyno ANGPTL8. In some embodiments, the ANGPTL8-binding agent binds within amino acids 32-46 of human ANGPTL8 and/or amino acids 32-46 of cyno ANGPTL8.

In some embodiments, the ANGPTL8-binding agent binds within amino acids 22-83 of SEQ ID NO:1. In some embodiments, the ANGPTL8-binding agent binds within amino acids 84-138 of SEQ ID NO:1. In some embodiments, the ANGPTL8-binding agent binds within amino acids 139-198 of SEQ ID NO:1. In some embodiments, the ANGPTL8-binding agent binds within amino acids 25-60 of SEQ ID NO:1. In some embodiments, the ANGPTL8-binding agent binds within amino acids 22-46 of SEQ ID NO:1. In some embodiments, the ANGPTL8-binding agent binds within amino acids 32-46 of SEQ ID NO:1.

In some embodiments, the ANGPTL8-binding agent binds an epitope comprising amino acids within SEQ ID NO:2. In some embodiments, the ANGPTL8-binding agent binds an epitope comprising amino acids within SEQ ID NO:3. In some embodiments, the ANGPTL8-binding agent binds an epitope comprising amino acids within SEQ ID NO:4. In some embodiments, the ANGPTL8-binding agent binds an epitope comprising amino acids within SEQ ID NO:5. In some embodiments, the ANGPTL8-binding agent binds an epitope comprising amino acids within SEQ ID NO:6. In some embodiments, the ANGPTL8-binding agent binds an epitope comprising amino acids within SEQ ID NO:7. In some embodiments, the ANGPTL8-binding agent binds an epitope comprising amino acids within SEQ ID NO: 8. In some embodiments, the ANGPTL8-binding agent binds at least one amino acid within SEQ ID NO:3. In some embodiments, the ANGPTL8-binding agent binds at least one amino acid within SEQ ID NO:4. In some embodiments, the ANGPTL8-binding agent binds at least one amino acid within SEQ ID NO:5. In some embodiments, the ANGPTL8-binding agent binds at least one amino acid within SEQ ID NO:6. In some embodiments, the ANGPTL8-binding agent binds at least one amino acid within SEQ ID NO:7. In some embodiments, the ANGPTL8-binding agent binds at least one amino acid within SEQ ID NO:8.

In some embodiments, the ANGPTL8-binding agent is an antibody. In some embodiments, the antibody is a recombinant antibody. In some embodiments, the antibody is a monoclonal antibody. In some embodiments, the antibody is a chimeric antibody. In some embodiments, the antibody is a humanized antibody. In some embodiments, the antibody is a human antibody. In some embodiments, the antibody is an IgA, IgD, IgE, IgG, or IgM antibody. In some embodiments, the antibody is an IgG1 antibody. In some embodiments, the antibody is an IgG2 antibody. In some embodiments, the antibody is an IgG4 antibody. In some embodiments, the antibody is an antibody fragment comprising an antigen-binding site. In some embodiments, the antibody is a bispecific antibody or a multispecific antibody. In some embodiments, the antibody is a monovalent antibody. In some embodiments, the antibody is a monospecific antibody. In some embodiments, the antibody is a bivalent antibody.

In some embodiments, the antibody is isolated. In some embodiments, the antibody is substantially pure.

In some embodiments, the ANGPTL8-binding agents are polyclonal antibodies. Polyclonal antibodies can be prepared by any known method. In some embodiments, polyclonal antibodies are produced by immunizing an animal (e.g., a rabbit, rat, mouse, goat, donkey) with an antigen of interest (e.g., a purified peptide fragment, a recombinant protein, or a fusion protein) using multiple subcutaneous or intraperitoneal injections. In some embodiments, the antigen is conjugated to a carrier such as keyhole limpet hemocyanin (KLH), serum albumin, bovine thyroglobulin, or soybean trypsin inhibitor. The antigen (with or without a carrier protein) is diluted in sterile saline and usually combined with an adjuvant (e.g., Complete or Incomplete Freund's Adjuvant) to form a stable emulsion. After a sufficient period of time, polyclonal antibodies are recovered from the immunized animal, usually from blood or ascites. The polyclonal antibodies can be purified from serum or ascites according to standard methods in the art including, but not limited to, affinity chromatography, ion-exchange chromatography, gel electrophoresis, and dialysis.

In some embodiments, an ANGPTL8-binding agent is a monoclonal antibody. In some embodiments, monoclonal antibodies are prepared using hybridoma methods known to one of skill in the art. For example, using the hybridoma method, a mouse, rat, rabbit, hamster, or other appropriate host animal, is immunized as described above to elicit the production of antibodies that specifically bind the immunizing antigen. In some embodiments, lymphocytes are immunized in vitro. In some embodiments, the immunizing antigen is a human protein or a fragment thereof. In some embodiments, the immunizing antigen is a mouse protein or a fragment thereof.

Following immunization, lymphocytes are isolated and fused with a suitable myeloma cell line using, for example, polyethylene glycol. The hybridoma cells are selected using specialized media as known in the art and unfused lymphocytes and myeloma cells do not survive the selection process. Hybridomas that produce monoclonal antibodies directed specifically against a chosen antigen can be identified by a variety of methods including, but not limited to, immunoprecipitation, immunoblotting, and in vitro binding assays (e.g., flow cytometry, FACS, ELISA, and radioimmunoassay). Once hybridoma cells that produce antibodies of the desired specificity, affinity, and/or activity are identified, the clones may be subcloned by limiting dilution techniques. The hybridomas can be propagated either in in vitro culture using standard methods or in vivo as ascites tumors in an animal. The monoclonal antibodies can be purified from the culture medium or ascites fluid according to standard methods in the art including, but not limited to, affinity chromatography, ion-exchange chromatography, gel electrophoresis, and dialysis.

In some embodiments, monoclonal antibodies are made using recombinant DNA techniques as known to one skilled in the art. For example, the polynucleotides encoding a monoclonal antibody are isolated from mature B-cells or hybridoma cells, such as by RT-PCR using oligonucleotide primers that specifically amplify the genes encoding the heavy and light chains of the antibody, and their sequence is determined using standard techniques. The isolated polynucleotides encoding the heavy and light chains are then cloned into suitable expression vectors which produce the monoclonal antibodies when transfected into host cells such as E. coli, simian COS cells, Chinese hamster ovary (CHO) cells, or myeloma cells that do not otherwise produce immunoglobulin proteins.

In some embodiments, recombinant monoclonal antibodies, or fragments thereof, are isolated from phage display libraries expressing variable domains or CDRs of a desired species. Screening of phage libraries can be accomplished by various techniques known in the art.

In some embodiments, a monoclonal antibody is modified, for example, by using recombinant DNA technology to generate alternative antibodies. In some embodiments, the constant domains of the light chain and heavy chain of, for example, a mouse monoclonal antibody are substituted for constant regions of, for example, a human antibody to generate a chimeric antibody, or for a non-immunoglobulin polypeptide to generate a fusion antibody. In some embodiments, the constant regions are truncated or removed to generate a desired antibody fragment of a monoclonal antibody. Site-directed or high-density mutagenesis of the variable region(s) can be used to optimize, for example, specificity and affinity of a monoclonal antibody.

In some embodiments, an ANGPTL8-binding agent is a humanized antibody. Various methods for generating humanized antibodies are known in the art. In some embodiments, a human antibody comprises one or more amino acid residues that have been introduced into it from a source that is non-human. These non-human amino acid residues are often referred to as "import" residues, which are typically taken from an "import" variable domain. In some embodiments, humanization is performed by substituting one or more non-human CDR sequences for the corresponding CDR sequences of a human antibody. In some embodiments, the humanized antibodies are constructed by CDR grafting, in which the amino acid sequences of all six CDRs of the parent non-human antibody (e.g., rodent) are grafted onto a human antibody framework.

The choice of which human heavy chain variable region and/or light chain variable region to be used in generating humanized antibodies can be made based on a variety of factors and by a variety of methods. In some embodiments, the "best-fit" method is used where the sequence of the variable region of a non-human (e.g., rodent) antibody is screened against the entire library of known human variable region sequences. The human sequence that is most similar to that of the rodent sequence is selected as the human variable region framework for the humanized antibody. In some embodiments, a method is used wherein a particular variable region framework derived from a consensus sequence of all human antibodies of a particular subgroup of light or heavy chains is selected. In some embodiments, the framework is derived from the consensus sequences of the most abundant human subclasses. In some embodiments, human germline genes are used as the source of the variable region framework sequences.

Other methods for humanization include, but are not limited to, a method called "superhumanization" which is described as the direct transfer of CDRs to a human germline framework, a method termed Human String Content (HSC) which is based on a metric of "antibody humanness," methods based on generation of large libraries of humanized variants (including phage, ribosomal, and yeast display libraries), and methods based on framework region shuffling.

In some embodiments, an ANGPTL8-binding agent is a human antibody. Human antibodies can be directly prepared using various techniques known in the art. In some embodiments, human antibodies are generated from immortalized human B lymphocytes immunized in vitro. In some embodiments, human antibodies are generated from lymphocytes isolated from an immunized individual. In any case, cells that produce an antibody directed against a target antigen can be generated and isolated. In some embodiments, a human antibody is selected from a phage library, where that phage library expresses human antibodies. Alternatively, phage display technology may be used to produce human antibodies and antibody fragments in vitro, from immunoglobulin variable region gene repertoires from unimmunized donors. Techniques for the generation and use of antibody phage libraries are well known in the art. Once antibodies are identified, affinity maturation strategies known in the art, including but not limited to, chain shuffling and site-directed mutagenesis, may be employed to generate higher affinity human antibodies.

In some embodiments, human antibodies are produced in transgenic mice that contain human immunoglobulin loci. Upon immunization these mice are capable of producing the full repertoire of human antibodies in the absence of endogenous immunoglobulin production.

In some embodiments, the ANGPTL8-binding agent is a bispecific antibody. Bispecific antibodies are capable of recognizing and binding at least two different antigens or epitopes. The different epitopes can either be within the same molecule (e.g., two epitopes on ANGPTL8) or on different molecules (e.g., one epitope on ANGPTL8 and one epitope on a different target). In some embodiments, a bispecific antibody has enhanced potency as compared to an individual antibody or to a combination of more than one antibody. In some embodiments, a bispecific antibody has reduced toxicity as compared to an individual antibody or to a combination of more than one antibody. It is known to those of skill in the art that any therapeutic agent may have unique pharmacokinetics (PK) (e.g., circulating half-life). In some embodiments, a bispecific antibody has the ability to synchronize the PK of two active binding agents wherein the two individual binding agents have different PK profiles. In some embodiments, a bispecific antibody has the ability to concentrate the actions of two agents in a common area (e.g., tissue) in a subject. In some embodiments, a bispecific antibody has the ability to concentrate the actions of two agents to a common target (e.g., a specific cell type). In some embodiments, a bispecific antibody has the ability to target the actions of two agents to more than one biological pathway or function. In some embodiments, a bispecific antibody has the ability to target two different cells and bring them closer together.

In some embodiments, a bispecific antibody has decreased toxicity and/or side effects. In some embodiments, a bispecific antibody has decreased toxicity and/or side effects as compared to a mixture of the two individual antibodies or the antibodies as single agents. In some embodiments, a bispecific antibody has an increased therapeutic index. In some embodiments, a bispecific antibody has an increased therapeutic index as compared to a mixture of the two individual antibodies or the antibodies as single agents.

Several techniques for making bispecific antibodies are known by those skilled in the art. In some embodiments, the bispecific antibodies comprise heavy chain constant regions with modifications in the amino acids which are part of the interface between the two heavy chains. In some embodiments, the bispecific antibodies are generated using a knobs-into-holes (KIH) strategy. In some embodiments, the bispecific antibodies comprise variant hinge regions incapable of forming disulfide linkages between the heavy chains. In some embodiments, the bispecific antibodies comprise heavy chains with changes in amino acids that result in altered electrostatic interactions. In some embodiments, the bispecific antibodies comprise heavy chains with changes in amino acids that result in altered hydrophobic/hydrophilic interactions.

Bispecific antibodies can be intact antibodies or antibody fragments comprising antigen-binding sites.

Antibodies with more than two valencies are also contemplated. For example, trispecific or tetraspecific antibodies can be prepared. Thus, in some embodiments the antibodies to ANGPTL8 are multispecific.

In some embodiments, the ANGPTL8-binding agent is an antibody that binds ANGPTL8. In some embodiments, the ANGPTL8-binding agent is an antibody that binds human ANGPTL8. In some embodiments, the ANGPTL8-binding agent is an antibody that binds cyno ANGPTL8. In some embodiments, the ANGPTL8-binding agent is an antibody that binds human and cyno ANGPTL8. In some embodiments, the ANGPTL8-binding agent is an antibody that binds mouse ANGPTL8. In some embodiments, the ANGPTL8-binding agent is an antibody that binds a portion or fragment of ANGPTL8. In some embodiments, the ANGPTL8-binding agent is an antibody that binds an ANGPTL8 peptide. In some embodiments, the ANGPTL8-binding agent is an antibody that binds the SE1 peptide. In some embodiments, the ANGPTL8-binding agent is an antibody that binds an ANGPTL8 epitope.

In some embodiments, the binding agent is an anti-ANGPTL8 antibody or antigen-binding fragment thereof that comprises one, two, three, four, five, and/or six CDRs of any one of the antibodies described herein. In some embodiments, an anti-ANGPTL8 antibody or antigen-binding fragment thereof comprises (i) one, two, and/or three heavy chain CDRs from Tables 1-3, and/or (ii) one, two, and/or three light chain CDRs from Tables 1-3.

In some embodiments, an antibody or antigen-binding fragment thereof that specifically binds ANGPTL8 comprises a heavy chain CDR1, CDR2, and CDR3 and a light chain CDR1, CDR2, CDR3 from Table 1. In some embodiments, an antibody or antigen-binding fragment thereof that specifically binds ANGPTL8 comprises a heavy chain CDR1, CDR2, and CDR3 and a light chain CDR1, CDR2, CDR3 from Table 2. In some embodiments, an antibody or antigen-binding fragment thereof that specifically binds ANGPTL8 comprises a heavy chain CDR1, CDR2, and CDR3 and a light chain CDR1, CDR2, CDR3 from Table 3.

TABLE 1

Antibody 1E5 CDR and Variable Region Sequences

| | Exemplary | IMGT | Kabat | Chothia | Contact | AbM |
|---|---|---|---|---|---|---|
| Heavy Chain CDR1 | GYTFTDYTIH (SEQ ID NO: 11) | GYTFTDYT (SEQ ID NO: 12) | DYTIH (SEQ ID NO: 13) | GYTFTDY (SEQ ID NO: 14) | TDYTIH (SEQ ID NO: 15) | GYTFTDYTIH (SEQ ID NO: 11) |
| Heavy Chain CDR2 | WFYPGSDNIKYNAKFKD (SEQ ID NO: 16) | FYPGSDNI (SEQ ID NO: 17) | WFYPGSDNIKYNAKFKD (SEQ ID NO: 16) | PGSD (SEQ ID NO: 18) | WIGWFYPGSDNIK (SEQ ID NO: 19) | WFYPGSDNIK (SEQ ID NO: 20) |
| Heavy Chain CDR3 | HEAFSYYDVAWFAY (SEQ ID NO: 21) | ARHEAFSYYDVAWFAY (SEQ ID NO: 22) | HEAFSYYDVAWFAY (SEQ ID NO: 21) | EAFSYYDVAWFA (SEQ ID NO: 23) | ARHEAFSYYDVAWFA (SEQ ID NO: 24) | HEAFSYYDVAWFAY (SEQ ID NO: 21) |
| Light Chain CDR1 | RSSQSLVHSNGNTYLH (SEQ ID NO: 25) | QSLVHSNGNTY (SEQ ID NO: 26) | RSSQSLVHSNGNTYLH (SEQ ID NO: 25) | SQSLVHSNGNTY (SEQ ID NO: 27) | VHSNGNTYLHWY (SEQ ID NO: 28) | RSSQSLVHSNGNTYLH (SEQ ID NO: 25) |
| Light Chain CDR2 | TVSNRFS (SEQ ID NO: 29) | TVS (SEQ ID NO: 30) | TVSNRFS (SEQ ID NO: 29) | TVS (SEQ ID NO: 30) | LLIYTVSNRF (SEQ ID NO: 31) | TVSNRFS (SEQ ID NO: 29) |
| Light Chain CDR3 | SQTTHFPYT (SEQ ID NO: 32) | SQTTHFPYT (SEQ ID NO: 32) | SQTTHFPYT (SEQ ID NO: 32) | TTHFPY (SEQ ID NO: 33) | SQTTHFPY (SEQ ID NO: 34) | SQTTHFPYT (SEQ ID NO: 32) |

TABLE 1-continued

Antibody 1E5 CDR and Variable Region Sequences

| Exemplary | IMGT | Kabat | Chothia | Contact | AbM |
|---|---|---|---|---|---|

1E5 Heavy Chain Variable Region
QVQLQQSGAELVKPGTSVRLSCKASGYTFTDYTIHWVKLRSGQGLEWIGWFYPGSDNIKYNAKFKDKATLTADKSSSTVYMDLGRL
TSEDSAVYFCARHEAFSYYDVAWFAYWGQGTLVTVSA (SEQ ID NO: 35)

1E5 Light Chain Variable Region
DVVMTQTPLSLPVSLGDQASISCRSSQSLVHSNGNTYLHWYLQKPGQSPKLLIYTVSNRFSGVPDRFSGSGSGSDFTLNFSRVEAE
DLGVYFCSQTTHFPYTFGGGTKLEIK (SEQ ID NO: 36)

Hz1E5.A1 Heavy Chain Variable Region
EVQLVQSGAEVKKPGSSVKVSCKASGYTFTDYTIHWVRQAPGQGLEWMGWFYPGSDNIKYNAKFKDRATLTADKSTSTAYMELSSL
RSEDTAVYYCARHEAFSYYDVAWFAYWGQGTLVTVSS (SEQ ID NO: 62)

Hz1E5.A1 Light Chain Variable Region
DVVMTQTPLSLPVTPGEPASISCRSSQSLVHSNGNTYLHWYLQKPGQSPQLLIYTVSNRFSGVPDRFSGSGSGSDFTLKISRVEAE
DVGVYFCSQTTHFPYTFGQGTKVEIK (SEQ ID NO: 63)

TABLE 2

Antibody 1E9 CDR and Variable Region Sequences

| | Exemplary | IMGT | Kabat | Chothia | Contact | AbM |
|---|---|---|---|---|---|---|
| Heavy Chain CDR1 | GYTFTDYTIH (SEQ ID NO: 11) | GYTFTDYT (SEQ ID NO: 12) | DYTIH (SEQ ID NO: 13) | GYTFTDY (SEQ ID NO: 14) | TDYTIH (SEQ ID NO: 15) | GYTFTDYTIH (SEQ ID NO: 11) |
| Heavy Chain CDR2 | WFYPGSDNIKFNAKFRD (SEQ ID NO: 37) | FYPGSDNI (SEQ ID NO: 17) | WFYPGSDNIKFNAKFRD (SEQ ID NO: 37) | PGSD (SEQ ID NO: 18) | WIGWFYPGSDNIK (SEQ ID NO: 19) | WFYPGSDNIK (SEQ ID NO: 20) |
| Heavy Chain CDR3 | HEAFYVYDVAWFAN (SEQ ID NO: 38) | ARHEAFYVYDVAWFAN (SEQ ID NO: 39) | HEAFYVYDVAWFAN (SEQ ID NO: 38) | EAFYVYDVAWFA (SEQ ID NO: 68) | ARHEAFYVYDVAWFA (SEQ ID NO: 69) | HEAFYVYDVAWFAN (SEQ ID NO: 38) |
| Light Chain CDR1 | RSSQSLVHSNGNTYLH (SEQ ID NO: 25) | QSLVHSNGNTY (SEQ ID NO: 26) | RSSQSLVHSNGNTYLH (SEQ ID NO: 25) | SQSLVHSNGNTY (SEQ ID NO: 27) | VHSNGNTYLHWF (SEQ ID NO: 40) | RSSQSLVHSNGNTYLH (SEQ ID NO: 25) |
| Light Chain CDR2 | TVSNRFS (SEQ ID NO: 29) | TVS (SEQ ID NO: 30) | TVSNRFS (SEQ ID NO: 29) | TVS (SEQ ID NO: 30) | LLIYTVSNRF (SEQ ID NO: 31) | TVSNRFS (SEQ ID NO: 29) |
| Light Chain CDR3 | SQSTHFPYT (SEQ ID NO: 41) | SQSTHFPYT (SEQ ID NO: 41) | SQSTHFPYT (SEQ ID NO: 41) | STHFPY (SEQ ID NO: 42) | SQSTHFPY (SEQ ID NO: 43) | SQSTHFPYT (SEQ ID NO: 41) |

1E9 Heavy Chain Variable Region
QVQLQQSGTELVKPGASVKLSCKASGYTFIDYTIHWVKQRSGQGLEWIGWFYPGSDNIKENAKFRDKATLTADKSSSIVYMELSRL
TSEDSAVYFCARHEAFYVYDVAWFANWGQGTLVTVST (SEQ ID NO: 44)

1E9 Light Chain Variable Region
DVVMTQTPLSLPVSLGDQASISCRSSQSLVHSNGNTYLHWFLQKPGQSPNLLIYIVSNRFSGVPDRFSGSGSGTDFILKISRVEAG
DLGVYFCSQSTHFPYTFGGGIKLEIK (SEQ ID NO: 45)

TABLE 3

Antibody 1A8 CDR and Variable Region Sequences

| | Exemplary | IMGT | Kabat | Chothia | Contact | AbM |
|---|---|---|---|---|---|---|
| Heavy Chain CDR1 | GYTFTDYTIH (SEQ ID NO: 11) | GYTFTDYT (SEQ ID NO: 12) | DYTIH (SEQ ID NO: 13) | GYTFTDY (SEQ ID NO: 14) | TDYTIH (SEQ ID NO: 15) | GYTFTDYTIH (SEQ ID NO: 11) |
| Heavy Chain CDR2 | WFYPGSDNIKYNEKFKD (SEQ ID NO: 46) | FYPGSDNI (SEQ ID NO: 17) | WFYPGSDNIKYNEKFKD (SEQ ID NO: 46) | PGSD (SEQ ID NO: 18) | WIGWFYPGSDNIKYNEKFKD (SEQ ID NO: 47) | WFYPGSDNIK (SEQ ID NO: 20) |

TABLE 3-continued

Antibody 1A8 CDR and Variable Region Sequences

| | Exemplary | IMGT | Kabat | Chothia | Contact | AbM |
|---|---|---|---|---|---|---|
| Heavy Chain CDR3 | HEAYYVYDVAWFAY (SEQ ID NO: 48) | ARHEAYYVYDVAW FAY (SEQ ID NO: 49) | HEAYYVYDVAWFAY (SEQ ID NO: 48) | EAYYVYDVAWFA (SEQ ID NO: 50) | ARHEAYYVYDVAWFA (SEQ ID NO: 51) | HEAYYVYDVAW FAY (SEQ ID NO: 48) |
| Light Chain CDR1 | SSSQSLVHSNGNT FLH (SEQ ID NO: 52) | QSLVHSNGNIF (SEQ ID NO: 53) | SSSQSLVHSNGNT FLH (SEQ ID NO: 52) | SQSLVHSNGNIF (SEQ ID NO: 54) | VHSNGNTFLHWF (SEQ ID NO: 55) | SSSQSLVHSNG NTFLH (SEQ ID NO: 52) |
| Light Chain CDR2 | TVSNRFS (SEQ ID NO: 29) | TVS (SEQ ID NO: 30) | TVSNRFS (SEQ ID NO: 29) | TVS (SEQ ID NO: 30) | LLIYTVSNRF (SEQ ID NO: 31) | TVSNRFS (SEQ ID NO: 29) |
| Light Chain CDR3 | SQSTHFPYT (SEQ ID NO: 41) | SQSTHFPYT (SEQ ID NO: 41) | SQSTHFPYT (SEQ ID NO: 41) | STHFPY (SEQ ID NO: 42) | SQSTHFPY (SEQ ID NO: 43) | SQSTHFPYT (SEQ ID NO: 41) |

1A8 Heavy Chain Variable Region
QVQLQQSGAELVKPGASVKLSCKASGYTFIDYTIHWVKQRSGQGLEWIGWFYPGSDNIKYNEKEKDKATLTADKSSIVYMELSRL
TSEDSAVYFCARHEAYYVYDVAWFAYWGQGTLVTVSA (SEQ ID NO: 56)

1A8 Light Chain Variable Region
DVVMTQTPLSLPVSLGDQASISCSSSQSLVHSNGNIFLHWFLQRPGQSPKLLIYIVSNRFSGVPDRFSGSGSGTDFILKISRVEAE
DLGVYFCSQSTHFPYTFGGGITLEIK (SEQ ID NO: 57)

CDRs are defined by a variety of methods/systems by those skilled in the art. These systems and/or definitions have been developed and refined over a number of years and include Kabat, Chothia, IMGT, AbM, and "contact." The Kabat definition is based on sequence variability and generally is the most commonly used. The Chothia definition is based on the location of the structural loop regions. The IMGT system is based on sequence variability and location within the structure of the variable domain. The AbM definition is a compromise between Kabat and Chothia. The "Contact" definition is based on analyses of the available antibody crystal structures. An Exemplary system, as included in Tables 1-3, is a combination of Kabat and Chothia. A comparison of these various definitions and numbering systems is shown below. These are also depicted in FIG. 1 which shows variable region sequence alignments of exemplary antibodies.

| | Exemplary | IMGT | Kabat | AbM | Chothia | Contact |
|---|---|---|---|---|---|---|
| HC CDR1 | 26-35 | 27-38 | 31-35 | 26-35 | 26-32 | 30-35 |
| HC CDR2 | 50-65 | 56-65 | 50-65 | 50-58 | 53-55 | 47-58 |
| HC CDR3 | 95-102 | 105-117 | 95-102 | 95-102 | 96-101 | 93-101 |
| LC CDR1 | 24-34 | 27-38 | 24-34 | 24-34 | 26-32 | 30-36 |
| LC CDR2 | 50-56 | 56-65 | 50-56 | 50-56 | 50-52 | 46-55 |
| LC CDR3 | 89-97 | 105-117 | 89-97 | 89-97 | 91-96 | 89-96 |

In some embodiments, an antibody that specifically binds ANGPTL8 comprises (a) a heavy chain CDR1 from Table 1, a heavy chain CDR2 from Table 1, and a heavy chain CDR3 from Table 1; and/or (b) a light chain CDR1 from Table 1, a light chain CDR2 from Table 1, and a light chain CDR3 from Table 1.

In some embodiments, an antibody that specifically binds ANGPTL8 comprises a heavy chain CDR1 comprising SEQ ID NOs:11, 12, 13, 14, or 15; a heavy chain CDR2 comprising SEQ ID NOs:16, 17, 18, 19, or 20; and a heavy chain CDR3 comprising SEQ ID NOs:21, 22, 23, or 24. In some embodiments, an anti-ANGPTL8 antibody further comprises a light chain CDR1 comprising SEQ ID NOs:25, 26, 27, or 28; a light chain CDR2 comprising SEQ ID NOs:29, 30, or 31; and a light chain CDR3 comprising SEQ ID NOs:32, 33, or 34. In some embodiments, an anti-ANGPTL8 antibody comprises a light chain CDR1 comprising SEQ ID NOs:25, 26, 27, or 28; a light chain CDR2 comprising SEQ ID NOs:29, 30, or 31; and a light chain CDR3 comprising SEQ ID NOs:32, 33, or 34. In some embodiments, an anti-ANGPTL8 antibody comprises a heavy chain CDR1 comprising SEQ ID NOs:11, 12, 13, 14, or 15; a heavy chain CDR2 comprising SEQ ID NOs:16, 17, 18, 19, or 20; a heavy chain CDR3 comprising SEQ ID NOs:21, 22, 23, or 24; a light chain CDR1 comprising SEQ ID NOs:25, 26, 27, or 28; a light chain CDR2 comprising SEQ ID NOs:29, 30, or 31; and a light chain CDR3 comprising SEQ ID NOs:32, 33, or 34. In some embodiments, an anti-ANGPTL8 antibody comprises a heavy chain CDR1 comprising SEQ ID NO:11; a heavy chain CDR2 comprising SEQ ID NO:16; a heavy chain CDR3 comprising SEQ ID NO:21; a light chain CDR1 comprising SEQ ID NO:25; a light chain CDR2 comprising SEQ ID NO:29; and a light chain CDR3 comprising SEQ ID NO:32. In some embodiments, an anti-ANGPTL8 antibody comprises a heavy chain CDR1 comprising SEQ ID NO:13; a heavy chain CDR2 comprising SEQ ID NO:16; a heavy chain CDR3 comprising SEQ ID NO:21; a light chain CDR1 comprising SEQ ID NO:25; a light chain CDR2 comprising SEQ ID NO:29; and a light chain CDR3 comprising SEQ ID NO:32.

In some embodiments, an antibody that specifically binds ANGPTL8 comprises: (a) a heavy chain CDR1 comprising SEQ ID NOs:11, 12, 13, 14, 15, or a variant thereof comprising 1, 2, 3, or 4 amino acid substitutions; a heavy chain CDR2 comprising SEQ ID NOs:16, 17, 18, 19, 20, or a variant thereof comprising 1, 2, 3, or 4 amino acid substitutions; a heavy chain CDR3 comprising SEQ ID NOs:21, 22, 23, 24, or a variant thereof comprising 1, 2, 3, or 4 amino acid substitutions; a light chain CDR1 comprising SEQ ID NOs:25, 26, 27, 28, or a variant thereof comprising 1, 2, 3, or 4 amino acid substitutions; a light chain CDR2 comprising SEQ ID NOs:29, 30, 31, or a variant thereof comprising 1, 2, 3, or 4 amino acid substitutions; and a light chain CDR3 comprising SEQ ID NOs:32, 33, 34, or a variant thereof comprising 1, 2, 3, or 4 amino acid substitutions. In some embodiments, the amino acid substitutions are conservative substitutions. In some embodiments, the substitutions are made as part of a humanization process. In some embodiments, the substitutions are made as part of a germline humanization process. In some embodiments, the substitutions are made as part of an affinity maturation process. In some embodiments, the substitutions are made as part of an optimization process.

In some embodiments, an antibody that specifically binds ANGPTL8 comprises (a) a heavy chain CDR1 from Table 2, a heavy chain CDR2 from Table 2, and a heavy chain CDR3 from Table 2; and/or (b) a light chain CDR1 from Table 2, a light chain CDR2 from Table 2, and a light chain CDR3 from Table 2.

In some embodiments, an antibody that specifically binds ANGPTL8 comprises a heavy chain CDR1 comprising SEQ ID NOs:11, 12, 13, 14, or 15; a heavy chain CDR2 comprising SEQ ID NOs:37, 17, 18, 19, or 20; and a heavy chain CDR3 comprising SEQ ID NOs:38, 39, 68, or 69. In some embodiments, an anti-ANGPTL8 antibody further comprises a light chain CDR1 comprising SEQ ID NOs:25, 26, 27, or 40; a light chain CDR2 comprising SEQ ID NOs:29, 30, or 31; and a light chain CDR3 comprising SEQ ID NOs:41, 42, or 43. In some embodiments, an anti-ANGPTL8 antibody comprises a light chain CDR1 comprising SEQ ID NOs:25, 26, 27, or 40; a light chain CDR2 comprising SEQ ID NOs:29, 30, or 31; and a light chain CDR3 comprising SEQ ID NOs:41, 42, or 43. In some embodiments, an anti-ANGPTL8 antibody comprises a heavy chain CDR1 comprising SEQ ID NOs:11, 12, 13, 14, or 15; a heavy chain CDR2 comprising SEQ ID NOs:37, 17, 18, 19, or 20; a heavy chain CDR3 comprising SEQ ID NOs:38, 39, 68, or 69; a light chain CDR1 comprising SEQ ID NOs:25, 26, 27, or 40; a light chain CDR2 comprising SEQ ID NOs:29, 30, or 31; and a light chain CDR3 comprising SEQ ID NOs:41, 42, or 43. In some embodiments, an anti-ANGPTL8 antibody comprises a heavy chain CDR1 comprising SEQ ID NO:11; a heavy chain CDR2 comprising SEQ ID NO:37; a heavy chain CDR3 comprising SEQ ID NO:38; a light chain CDR1 comprising SEQ ID NO:25; a light chain CDR2 comprising SEQ ID NO:29; and a light chain CDR3 comprising SEQ ID NO:41. In some embodiments, an anti-ANGPTL8 antibody comprises a heavy chain CDR1 comprising SEQ ID NO:13; a heavy chain CDR2 comprising SEQ ID NO:37; a heavy chain CDR3 comprising SEQ ID NO:38; a light chain CDR1 comprising SEQ ID NO:25; a light chain CDR2 comprising SEQ ID NO:29; and a light chain CDR3 comprising SEQ ID NO:41.

In some embodiments, an antibody that specifically binds ANGPTL8 comprises: (a) a heavy chain CDR1 comprising SEQ ID NOs:11, 12, 13, 14, 15, or a variant thereof comprising 1, 2, 3, or 4 amino acid substitutions; a heavy chain CDR2 comprising SEQ ID NOs:37, 17, 18, 19, 20, or a variant thereof comprising 1, 2, 3, or 4 amino acid substitutions; a heavy chain CDR3 comprising SEQ ID NOs:38, 39, 68, 69, or a variant thereof comprising 1, 2, 3, or 4 amino acid substitutions; a light chain CDR1 comprising SEQ ID NOs:25, 26, 27, 40, or a variant thereof comprising 1, 2, 3, or 4 amino acid substitutions; a light chain CDR2 comprising SEQ ID NOs:29, 30, 31, or a variant thereof comprising 1, 2, 3, or 4 amino acid substitutions; and a light chain CDR3 comprising SEQ ID NOs:41, 42, 43, or a variant thereof comprising 1, 2, 3, or 4 amino acid substitutions. In some embodiments, the amino acid substitutions are conservative substitutions. In some embodiments, the substitutions are made as part of a humanization process. In some embodiments, the substitutions are made as part of a germline humanization process. In some embodiments, the substitutions are made as part of an affinity maturation process. In some embodiments, the substitutions are made as part of an optimization process.

In some embodiments, an antibody that specifically binds ANGPTL8 comprises (a) a heavy chain CDR1 from Table 3, a heavy chain CDR2 from Table 3, and a heavy chain CDR3 from Table 3; and/or (b) a light chain CDR1 from Table 3, a light chain CDR2 from Table 3, and a light chain CDR3 from Table 3.

In some embodiments, an antibody that specifically binds ANGPTL8 comprises a heavy chain CDR1 comprising SEQ ID NOs:11, 12, 13, 14, or 15; a heavy chain CDR2 comprising SEQ ID NOs:46, 17, 18, 47, or 20; and a heavy chain CDR3 comprising SEQ ID NOs:48, 49, 50, 51. In some embodiments, an anti-ANGPTL8 antibody further comprises a light chain CDR1 comprising SEQ ID NOs:52, 53, 54, or 55; a light chain CDR2 comprising SEQ ID NOs:29, 30, or 31; and a light chain CDR3 comprising SEQ ID NOs:41, 42, or 43. In some embodiments, an anti-ANGPTL8 antibody comprises a light chain CDR1 comprising SEQ ID NOs:52, 53, 54, or 55; a light chain CDR2 comprising SEQ ID NOs:29, 30, or 31; and a light chain CDR3 comprising SEQ ID NOs:41, 42, or 43. In some embodiments, an anti-ANGPTL8 antibody comprises a heavy chain CDR1 comprising SEQ ID NOs:11, 12, 13, 14, or 15; a heavy chain CDR2 comprising SEQ ID NOs:46, 17, 18, 47, or 20; a heavy chain CDR3 comprising SEQ ID NOs:48, 49, 50, or 51; a light chain CDR1 comprising SEQ ID NOs:52, 53, 54, or 55; a light chain CDR2 comprising SEQ ID NOs:29, 30, or 31; and a light chain CDR3 comprising SEQ ID NOs:41, 42, or 43. In some embodiments, an anti-ANGPTL8 antibody comprises a heavy chain CDR1 comprising SEQ ID NO:11; a heavy chain CDR2 comprising SEQ ID NO:46; a heavy chain CDR3 comprising SEQ ID NO:48; a light chain CDR1 comprising SEQ ID NO:52; a light chain CDR2 comprising SEQ ID NO:29; and a light chain CDR3 comprising SEQ ID NO:41. In some embodiments, an anti-ANGPTL8 antibody comprises a heavy chain CDR1 comprising SEQ ID NO:13; a heavy chain CDR2 comprising SEQ ID NO:46; a heavy chain CDR3 comprising SEQ ID NO:48; a light chain CDR1 comprising SEQ ID NO:52; a light chain CDR2 comprising SEQ ID NO:29; and a light chain CDR3 comprising SEQ ID NO:41.

In some embodiments, an antibody that specifically binds ANGPTL8 comprises: (a) a heavy chain CDR1 comprising SEQ ID NOs:11, 12, 13, 14, 15, or a variant thereof comprising 1, 2, 3, or 4 amino acid substitutions; a heavy chain CDR2 comprising SEQ ID NOs:46, 17, 18, 47, 20, or a variant thereof comprising 1, 2, 3, or 4 amino acid substitutions; a heavy chain CDR3 comprising SEQ ID NOs:48, 49, 50, 51, or a variant thereof comprising 1, 2, 3, or 4 amino acid substitutions; a light chain CDR1 comprising SEQ ID NOs:52, 53, 54, 55, or a variant thereof comprising 1, 2, 3, or 4 amino acid substitutions; a light chain CDR2 comprising SEQ ID NOs:29, 30, 31, or a variant thereof comprising 1, 2, 3, or 4 amino acid substitutions; and a light chain CDR3 comprising SEQ ID NOs:41, 42, 43, or a variant thereof comprising 1, 2, 3, or 4 amino acid substitutions. In some embodiments, the amino acid substitutions are conservative substitutions. In some embodiments, the substitutions are made as part of a humanization process. In some embodiments, the substitutions are made as part of a germline humanization process. In some embodiments, the substitutions are made as part of an affinity maturation process. In some embodiments, the substitutions are made as part of an optimization process.

In some embodiments, the antibody or antigen-binding fragment thereof comprising the CDRs described herein further comprises (a) a heavy chain FR1, a heavy chain FR2, a heavy chain FR3, and a heavy chain FR4; and/or (b) a light chain FR1, a light chain FR2, a light chain FR3, and a light chain FR4.

Sequence alignments of the heavy chain variable regions and the light chain variable regions of the exemplary antibodies described herein were prepared and are shown in FIG. 1. In some embodiments, an anti-ANGPTL8 antibody comprises a heavy chain CDR1 comprising GYTFTDYTIH (SEQ ID NO:11); a heavy chain CDR2 comprising WFYPGSDNIKX$_1$NX$_2$KFX$_3$D, wherein X$_1$ is Y or F, X$_2$ is A or E and X$_3$ is K or R (SEQ ID NO:58); a heavy chain CDR3 comprising HEAX$_1$X$_2$X$_3$YDVAWFAX$_4$, wherein X$_1$ is F or Y, X$_2$ is S or Y, X$_3$ is Y or V, and X$_4$ is Y or N (SEQ ID NO:59); a light chain CDR1 comprising X$_1$SSQSLVHSNGNTX$_2$LH, wherein X$_1$ is R or S and X$_2$ is Y or F (SEQ ID NO:60); a light chain CDR2 comprising TVSNRFS (SEQ ID NO:29); and a light chain CDR3 comprising SQX$_1$THFPYT, wherein X$_1$ is T or S (SEQ ID NO:61).

In some embodiments, an antibody that specifically binds ANGPTL8 comprises a heavy chain variable region having at least about 80% sequence identity to SEQ ID NO:35, SEQ ID NO:44, or SEQ ID NO:56 and/or a light chain variable region having at least 80% sequence identity to SEQ ID NO:36, SEQ ID NO:45, or SEQ ID NO:57. In some embodiments, an anti-ANGPTL8 antibody comprises a heavy chain variable region having at least about 85%, at least about 90%, at least about 95%, at least about 97%, or at least about 99% sequence identity to SEQ ID NO:35. In some embodiments, an anti-ANGPTL8 antibody comprises a heavy chain variable region having at least about 85%, at least about 90%, at least about 95%, at least about 97%, or at least about 99% sequence identity to SEQ ID NO:44. In some embodiments, an anti-ANGPTL8 antibody comprises a heavy chain variable region having at least about 85%, at least about 90%, at least about 95%, at least about 97%, or at least about 99% sequence identity to SEQ ID NO:56. In some embodiments, an anti-ANGPTL8 antibody comprises a light chain variable region having at least about 85%, at least about 90%, at least about 95%, at least about 97%, or at least about 99% sequence identity to SEQ ID NO:36. In some embodiments, an anti-ANGPTL8 antibody comprises a light chain variable region having at least about 85%, at least about 90%, at least about 95%, at least about 97%, or at least about 99% sequence identity to SEQ ID NO:45. In some embodiments, an anti-ANGPTL8 antibody comprises a light chain variable region having at least about 85%, at least about 90%, at least about 95%, at least about 97%, or at least about 99% sequence identity to SEQ ID NO:57. In some embodiments, an anti-ANGPTL8 antibody comprises a heavy chain variable region having at least about 95% sequence identity to SEQ ID NO:35, SEQ ID NO:44, or SEQ ID NO:56 and/or a light chain variable region having at least about 95% sequence identity to SEQ ID NO:36, SEQ ID NO:45, or SEQ ID NO:57. In some embodiments, an anti-ANGPTL8 antibody comprises a heavy chain variable region comprising SEQ ID NO:35, SEQ ID NO:44, or SEQ ID NO:56 and/or a light chain variable region comprising SEQ ID NO:36, SEQ ID NO:45, or SEQ ID NO:57. In some embodiments, an anti-ANGPTL8 antibody comprises a heavy chain variable region comprising SEQ ID NO:35, SEQ ID NO:44, or SEQ ID NO:56 and a light chain variable region comprising SEQ ID NO:36, SEQ ID NO:45, or SEQ ID NO:57. In some embodiments, an anti-ANGPTL8 antibody comprises a heavy chain variable region consisting essentially of SEQ ID NO:35, SEQ ID NO:44, or SEQ ID NO:56 and a light chain variable region consisting essentially of SEQ ID NO:36, SEQ ID NO:45, or SEQ ID NO:57. In some embodiments, an anti-ANGPTL8 antibody comprises a heavy chain variable region consisting of SEQ ID NO:35, SEQ ID NO:44, or SEQ ID NO:56 and a light chain variable region consisting of SEQ ID NO:36, SEQ ID NO:45, or SEQ ID NO:57. In some embodiments, an anti-ANGPTL8 antibody comprises a heavy chain variable region comprising SEQ ID NO:35 and a light chain variable region comprising SEQ ID NO:36. In some embodiments, an anti-ANGPTL8 antibody comprises a heavy chain variable region comprising SEQ ID NO:44 and a light chain variable region comprising SEQ ID NO:45. In some embodiments, an anti-ANGPTL8 antibody comprises a heavy chain variable region comprising SEQ ID NO:56 and a light chain variable region comprising SEQ ID NO:57.

In some embodiments, an antibody that specifically binds ANGPTL8 comprises a humanized version or humanized variant of any one of the antibodies described herein. In some embodiments, an antibody is a humanized antibody comprising (a) a heavy chain CDR1 from Table 1, a heavy chain CDR2 from Table 1, and a heavy chain CDR3 from Table 1; and/or (b) a light chain CDR1 from Table 1, a light chain CDR2 from Table 1, and a light chain CDR3 from Table 1. In some embodiments, an antibody is a humanized antibody comprising (a) a heavy chain CDR1 from Table 2, a heavy chain CDR2 from Table 2, and a heavy chain CDR3 from Table 2; and/or (b) a light chain CDR1 from Table 2, a light chain CDR2 from Table 2, and a light chain CDR3 from Table 2. In some embodiments, an antibody is a humanized antibody comprising (a) a heavy chain CDR1 from Table 3, a heavy chain CDR2 from Table 3, and a heavy chain CDR3 from Table 3; and/or (b) a light chain CDR1 from Table 3, a light chain CDR2 from Table 3, and a light chain CDR3 from Table 3.

In some embodiments, an anti-ANGPTL8 antibody comprises a heavy chain variable region having at least about 80% sequence identity to SEQ ID NO:62 and a light chain variable region having at least about 80% sequence identity to SEQ ID NO:63. In some embodiments, an anti-ANGPTL8 antibody comprises a heavy chain variable region having at least about 85%, at least about 90%, at least about 95%, at least about 96%, at least about 97%, at least about 98%, at least about 99% sequence identity to SEQ ID NO:62 and a light chain variable region having at least about 85%, at least about 90%, at least about 95%, at least about 96%, at least about 97%, at least about 98%, at least about 99% sequence identity to SEQ ID NO:63. In some embodiments, an anti-ANGPTL8 antibody comprises a heavy chain variable region comprising SEQ ID NO:62 and a light chain variable region comprising SEQ ID NO:63. In some embodiments, an anti-ANGPTL8 antibody comprises a heavy chain comprising SEQ ID NO:64 and a light chain comprising SEQ ID NO:65.

Provided herein are antibodies that compete with one or more of the antibodies or antigen-binding fragments thereof described herein for binding to human ANGPTL8. In some embodiments, an antibody binds the same epitope as one of the antibodies described herein. In some embodiments, an antibody binds an epitope overlapping with an epitope bound by one of the antibodies described herein. Antibodies and antigen-binding fragments that compete with or bind to the same epitope as the antibodies described herein are expected to show similar functional properties.

The antibodies described herein and antigen-binding fragments thereof include those comprising one, two, three, four, five, and/or six of the CDRs provided in Tables 1-3. The antibodies described herein and antigen-binding fragments include those comprising a heavy chain variable region and/or a light chain variable region provided in Tables 1-3. As a specific but non-limiting example, antibodies provided herein include those that compete with an antibody comprising: (a) one, two, three, four, five, or all six of the CDRs provided in Tables 1-3; (b) a heavy chain variable region and a light chain variable region selected from those provided in Tables 1-3; or (c) two light chains and two heavy chains comprising a heavy chain variable region and a light chain variable region as provided in Tables 1-3.

In some embodiments, an antibody or antigen-binding fragment thereof competes for binding to ANGPTL8 with an anti-ANGPTL8 antibody described herein. In some embodiments, an antibody or antigen-binding fragment thereof competes for binding to ANGPTL8 with a reference antibody, wherein the reference antibody comprises: (a) comprises a heavy chain CDR1 comprising GYTFTDYTIH (SEQ ID NO:11); a heavy chain CDR2 comprising WFYPGSDNIKX$_1$NX$_2$KFX$_3$D, wherein X$_1$ is Y or F, X$_2$ is A or E and X$_3$ is K or R (SEQ ID NO:58); and a heavy chain CDR3 comprising HEAX$_1$X$_2$X$_3$YDVAWFAX$_4$, wherein X$_1$ is F or Y, X$_2$ is S or Y, X$_3$ is Y or V, and X$_4$ is Y or N (SEQ ID NO:59); and/or (b) a light chain CDR1 comprising X$_1$SSQSLVHSNGNTX$_2$LH, wherein X$_1$ is R or S and X$_2$ is Y or F (SEQ ID NO:60); a light chain CDR2 comprising TVSNRFS (SEQ ID NO:29); and a light chain CDR3 comprising SQX$_1$THFPYT, wherein X$_1$ is T or S (SEQ ID NO:61). In some embodiments, an antibody or antigen-binding fragment thereof competes for binding to ANGPTL8 with a reference antibody, wherein the reference antibody comprises a heavy chain CDR1 comprising SEQ ID NOs:11, 12, 13, 14, or 15; a heavy chain CDR2 comprising SEQ ID NOs:16, 17, 18, 19, or 20; a heavy chain CDR3 comprising SEQ ID NOs:21, 22, 23, or 24; a light chain CDR1 comprising SEQ ID NOs:25, 26, 27, or 28; a light chain CDR2 comprising SEQ ID NOs:29, 30, or 31; and a light chain CDR3 comprising SEQ ID NOs:32, 33, or 34. In some embodiments, an antibody or antigen-binding fragment thereof competes for binding to ANGPTL8 with a reference antibody, wherein the reference antibody comprises a heavy chain CDR1 comprising SEQ ID NOs:11, 12, 13, 14, or 15; a heavy chain CDR2 comprising SEQ ID NOs:37, 17, 18, 19, or 20; a heavy chain CDR3 comprising SEQ ID NOs:38, 39, 68, or 69; a light chain CDR1 comprising SEQ ID NOs:25, 26, 27, or 40; a light chain CDR2 comprising SEQ ID NOs:29, 30, or 31; and a light chain CDR3 comprising SEQ ID NOs:41, 42, or 43. In some embodiments, an antibody or antigen-binding fragment thereof competes for binding to ANGPTL8 with a reference antibody, wherein the reference antibody comprises a heavy chain CDR1 comprising SEQ ID NOs:11, 12, 13, 14, or 15; a heavy chain CDR2 comprising SEQ ID NOs:46, 17, 18, 47, or 20; a heavy chain CDR3 comprising SEQ ID NOs:48, 49, 50, or 51; a light chain CDR1 comprising SEQ ID NOs:52, 53, 54, or 55; a light chain CDR2 comprising SEQ ID NOs:29, 30, or 31; and a light chain CDR3 comprising SEQ ID NOs:41, 42, or 43.

In some embodiments, an antibody or antigen-binding fragment thereof competes for binding to ANGPTL8 with a reference antibody, wherein the reference antibody comprises (a) a heavy chain variable region comprising SEQ ID NO:35, 44, 56, or 62; and (b) a light chain variable region comprising SEQ ID NO:36, 45, 57, or 63. In some embodiments, an antibody competes for specific binding to ANGPTL8 with a reference antibody, wherein the reference antibody comprises a heavy chain variable region comprising SEQ ID NO:35 and a light chain variable region comprising SEQ ID NO:36. In some embodiments, an antibody competes for specific binding to ANGPTL8 with a reference antibody, wherein the reference antibody comprises a heavy chain variable region comprising SEQ ID NO:44 and a light chain variable region comprising SEQ ID NO:45. In some embodiments, an antibody competes for specific binding to ANGPTL8 with a reference antibody, wherein the reference antibody comprises a heavy chain variable region comprising SEQ ID NO:56 and a light chain variable region comprising SEQ ID NO:57. In some embodiments, an antibody competes for specific binding to ANGPTL8 with a reference antibody, wherein the reference antibody comprises a heavy chain variable region comprising SEQ ID NO:62 and a light chain variable region comprising SEQ ID NO:63.

In some embodiments, the ANGPTL8-binding agents described herein comprise antibodies (e.g., full-length antibodies or antigen-binding fragments thereof) in which at least one or more of the constant regions has been modified or deleted. In some embodiments, the antibodies may comprise modifications to one or more of the three heavy chain constant regions (CH1, CH2 or CH3) and/or to the light chain constant region (CL). In some embodiments, the heavy chain constant region of the modified antibodies comprises at least one human constant region. In some embodiments, the heavy chain constant region of the modified antibodies comprises more than one human constant region. In some embodiments, modifications to the constant region comprise additions, deletions, or substitutions of one or more amino acids in one or more regions. In some embodiments, one or more regions are partially or entirely deleted from the constant regions of the modified antibodies. In some embodiments, the entire CH2 domain has been removed from an antibody (ΔCH2 constructs). In some embodiments, a deleted constant region is replaced by a short amino acid spacer that provides some of the molecular flexibility typically imparted by the absent constant region. In some embodiments, a modified antibody comprises a CH3 domain directly fused to the hinge region of the antibody. In some embodiments, a modified antibody comprises a peptide spacer inserted between the hinge region and modified CH2 and/or CH3 domains.

It is known in the art that the constant region(s) of an antibody mediates several effector functions. For example, binding of the C1 component of complement to the Fc region of IgG or IgM antibodies (bound to antigen) activates the complement system. Activation of complement is important in the opsonization and lysis of cell pathogens. The activation of complement also stimulates the inflammatory response and can be involved in autoimmune hypersensitivity. In addition, the Fc region of an antibody can bind a cell expressing a Fc receptor (FcR). There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell cytotoxicity or ADCC), release of inflammatory mediators, placental transfer, and control of immunoglobulin production.

In some embodiments, the modified antibodies provide for altered effector functions that, in turn, affect the biological profile of the administered antibody. For example, in some embodiments, the deletion or inactivation (through point mutations or other means) of a constant region may reduce Fc receptor binding of the circulating modified antibody. In some embodiments, the constant region modifications increase the serum half-life of the antibody. In some embodiments, the constant region modifications reduce the serum half-life of the antibody. In some embodiments, the constant region modifications decrease or remove ADCC and/or complement dependent cytotoxicity (CDC) of the antibody. For example, specific amino acid substitutions in a human IgG1 Fc region with corresponding IgG2 or IgG4 residues may reduce effector functions (e.g., ADCC and CDC) in the modified antibody. Thus, in some embodiments, an antibody does not have one or more effector functions. In some embodiments, the antibody has no ADCC activity and/or no CDC activity. In some embodiments, the antibody does not bind an Fc receptor and/or complement factors. In some embodiments, the antibody has no effector function(s). In some embodiments, the constant region is modified to eliminate disulfide linkages or oligosaccharide moieties. In some embodiments, the constant region is modified to add/substitute one or more amino acids to provide, for example, one or more cytotoxin or carbohydrate attachment sites.

Modifications to the constant region of antibodies described herein may be made using well known biochemical or molecular engineering techniques. In some embodiments, antibody variants can be prepared by introducing appropriate nucleotide changes into the encoding DNA, and/or by synthesis of the desired antibody or polypeptide. In this respect it may be possible to disrupt the activity or effector function provided by a specific sequence or region while substantially maintaining the structure, binding activity, and other desired characteristics of the modified antibody.

The present disclosure further embraces additional variants and equivalents that are substantially homologous to the recombinant, monoclonal, chimeric, humanized, and human antibodies, or antibody fragments thereof, described herein. In some embodiments, it may be desirable to improve the binding affinity of the antibody. In some embodiments, it may be desirable to modulate other biological properties of the antibody, including but not limited to, specificity, thermostability, expression level, effector function(s), glycosylation, immunogenicity, or solubility. Those skilled in the art will appreciate that amino acid changes may alter post-translational processes of an antibody, such as changing the number or position of glycosylation sites or altering membrane anchoring characteristics.

Variations may be a substitution, deletion, or insertion of one or more nucleotides encoding the antibody or polypeptide that results in a change in the amino acid sequence as compared with the native antibody or polypeptide sequence. Amino acid substitutions can be the result of replacing one amino acid with another amino acid having similar structural and/or chemical properties, such as the replacement of a leucine with a serine, e.g., conservative amino acid replacements. Insertions or deletions may optionally be in the range of about 1 to 5 amino acids. In some embodiments, the substitution, deletion, or insertion includes less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the parent molecule. Variations in the amino acid sequence that are biologically useful and/or relevant may be determined by systematically making insertions, deletions, or substitutions in the sequence and testing the resulting variant proteins for activity as compared to the parental protein.

In some embodiments, variants may include addition of amino acid residues at the amino- and/or carboxyl-terminal end of the antibody or polypeptide. The length of additional amino acids residues may range from one residue to a hundred or more residues. In some embodiments, a variant comprises an N-terminal methionyl residue. In some embodiments, the variant comprises an additional polypeptide/protein, i.e., a fusion protein. In some embodiments, a variant is engineered to be detectable and may comprise a detectable label and/or protein (e.g., an enzyme).

In some embodiments, a cysteine residue not involved in maintaining the proper conformation of an antibody may be substituted or deleted to modulate the antibody's characteristics, e.g., to improve oxidative stability and/or prevent aberrant disulfide crosslinking. Conversely, in some embodiments, one or more cysteine residues may be added to create disulfide bond(s) to improve stability.

In some embodiments, an antibody of the present disclosure is "deimmunized." The deimmunization of antibodies generally consists of introducing specific amino acid mutations (e.g., substitutions, deletions, additions) to remove T-cell epitopes without significantly reducing the binding affinity or other desired activities of the antibody.

The variant antibodies or polypeptides described herein may be generated using methods known in the art, including but not limited to, site-directed mutagenesis, alanine scanning mutagenesis, and PCR mutagenesis.

In some embodiments, binding agents described herein are chemically modified. In some embodiments, the binding agents are antibodies that have been chemically modified by glycosylation, acetylation, pegylation, phosphorylation, amidation, derivatization by known protecting/blocking groups, proteolytic cleavage, and/or linkage to a cellular ligand or other protein. Any of numerous chemical modifications may be carried out by known techniques.

The present disclosure encompasses binding agents built upon non-immunoglobulin backbones, wherein the agents bind to the same epitope or essentially the same epitope as an anti-ANGPTL8 antibody disclosed herein. In some embodiments, a non-immunoglobulin-based binding agent is an agent that competes with an anti-ANGPTL8 antibody described herein in a competitive binding assay. In some embodiments, alternative binding agents comprise a scaffold protein. Generally, scaffold proteins can be assigned to one of three groups based on the architecture of their backbone (1) scaffolds consisting of α-helices; (2) small scaffolds with few secondary structures or an irregular architecture of α-helices and β-sheets; and (3) scaffolds consisting of predominantly β-sheets. Scaffold proteins include, but are not limited to, anticalins, which are based upon the lipocalin scaffold; adnectins, which are based on the $10^{th}$ domain of human fibronectin type 3; affibodies, which are based on the B-domain in the Ig-binding region of Staphylococcus aureus protein A; darpins, which are based on ankyrin repeat domain proteins; fynomers, which are based on the SH3 domain of the human Fyn protein kinase; affitins, which are based on Sac7d from *Sulfolobus acidocaldarius*; affilins, which are based on human γ-B-crystallin or human ubiquitin; avimers, which are based on the A-domains of membrane receptor proteins; knottins (cysteine knot miniproteins), which are based upon a stable 30-amino acid antiparallel β-strand protein fold; and Kunitz domain inhibitor scaffolds, which are based upon a structure that contains three disulfide bonds and three loops. In some embodiments, an ANGPTL8-binding agent comprises an engineered scaffold protein comprising one or more CDRs as shown in Tables 1-3.

Generally speaking, antigen-antibody interactions are non-covalent and reversible, formed by a combination of hydrogen bonds, hydrophobic interactions, electrostatic and van der Waals forces. When describing the strength of an antigen-antibody complex, affinity and/or avidity are usually mentioned. The binding of an antibody to its antigen is a reversible process, and the affinity of the binding is typically reported as an equilibrium dissociation constant ($K_D$) $K_D$ is the ratio of an antibody dissociation rate ($k_{off}$) (how quickly it dissociates from its antigen) to the antibody association rate ($k_{on}$) (how quickly it binds to its antigen). In some embodiments, $K_D$ values are determined by measuring the $k_{on}$ and $k_{off}$ rates of a specific antibody/antigen interaction and then using a ratio of these values to calculate the $K_D$ value. $K_D$ values may be used to evaluate and rank order the strength of individual antibody/antigen interactions. The lower the KD of an antibody, the higher the affinity of the antibody for its target. Avidity gives a measure of the overall strength of an antibody-antigen complex. It is dependent on three major parameters: (i) affinity of the antibody for the epitope, (ii) valency of both the antibody and antigen, and (iii) structural arrangement of the parts that interact.

In some embodiments, an ANGPTL8-binding agent (e.g., an antibody) binds ANGPTL8 with a dissociation constant (KD) of about 1 μM or less, about 100 nM or less, about 40 nM or less, about 20 nM or less, about 10 nM or less, about 1 nM or less, about 0.1 nM or less, 50 μM or less, 10 μM or less, or 1 μM or less. In some embodiments, an ANGPTL8-binding agent binds ANGPTL8 with a KD of about 20 nM or less. In some embodiments, an ANGPTL8-binding agent binds ANGPTL8 with a KD of about 10 nM or less. In some embodiments, an ANGPTL8-binding agent binds ANGPTL8 with a KD of about 1 nM or less. In some embodiments, an ANGPTL8-binding agent binds ANGPTL8 with a KD of about 0.5 nM or less. In some embodiments, an ANGPTL8-binding agent binds ANGPTL8 with a $K_D$ of about 0.1 nM or less. In some embodiments, an ANGPTL8-binding agent binds ANGPTL8 with a $K_D$ of about 50 pM or less. In some embodiments, an ANGPTL8-binding agent binds ANGPTL8 with a $K_D$ of about 25 pM or less. In some embodiments, an ANGPTL8-binding agent binds ANGPTL8 with a $K_D$ of about 10 pM or less. In some embodiments, an ANGPTL8-binding agent binds ANGPTL8 with a KD of about 1 pM or less. In some embodiments, the dissociation constant of the binding agent (e.g., an antibody) to ANGPTL8 is the dissociation constant determined using an ANGPTL8 fusion protein comprising at least a portion or antigen-binding fragment of ANGPTL8 immobilized on a BIACORE chip. In some embodiments, the dissociation constant of the binding agent (e.g., an antibody) to ANGPTL8 is the dissociation constant determined using an ANGPTL8 peptide (e.g., SE1 peptide) immobilized on a BIACORE chip. In some embodiments, the dissociation constant of the binding agent (e.g., an antibody) to ANGPTL8 is the dissociation constant determined using the binding agent captured by an anti-human IgG antibody on a BIACORE chip and soluble ANGPTL8 or a fragment thereof.

In some embodiments, the ANGPTL8-binding agent (e.g., an antibody) binds ANGPTL8 with a half maximal effective concentration (EC50) of about 1 μM or less, about 100 nM or less, about 40 nM or less, about 20 nM or less, about 10 nM or less, about 1 nM or less, or about 0.1 nM or less. In some embodiments, an ANGPTL8-binding agent binds to human ANGPTL8 with an EC50 of about 1 μM or less, about 100 nM or less, about 40 nM or less, about 20 nM or less, about 10 nM or less, about 1 nM or less, or about 0.1 nM or less. In some embodiments, an ANGPTL8-binding agent binds mouse ANGPTL8 and/or human ANGPTL8 with an EC50 of about 40 nM or less, about 20 nM or less, about 10 nM or less, about 1 nM or less or about 0.1 nM or less.

The binding agents (e.g., antibodies or antigen-binding fragments thereof) described herein can be produced by any suitable method known in the art. Such methods range from direct protein synthesis methods to constructing a DNA sequence encoding polypeptide sequences and expressing those sequences in a suitable host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional variants thereof. In some embodiments, a DNA sequence encoding a polypeptide of interest is constructed by chemical synthesis using an oligonucleotide synthesizer. Oligonucleotides can be designed based on the amino acid sequence of the desired polypeptide and selecting those codons that are favored in the host cell in which the recombinant polypeptide of interest will be produced. Standard methods can be applied to synthesize a polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis, or another method), the polynucleotide sequences encoding a particular polypeptide of interest can be inserted into an expression vector and operatively linked to an expression control sequence appropriate for expression of the protein in a desired host. Proper assembly can be confirmed by nucleotide sequencing, restriction enzyme mapping, and/or expression of a biologically active polypeptide in a suitable host. As is well-known in the art, in order to obtain high expression levels of a transfected gene in a host, the gene must be operatively linked to transcriptional and translational expression control sequences that are functional in the chosen expression host.

In some embodiments, recombinant expression vectors are used to amplify and express DNA encoding antibodies, or fragments thereof, against human ANGPTL8. For example, recombinant expression vectors can be replicable DNA constructs which have synthetic or cDNA-derived DNA fragments encoding a polypeptide chain of an ANGPTL8-binding agent, such as an anti-ANGPTL8 antibody, or antigen-binding fragment thereof, operatively linked to suitable transcriptional and/or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences. Regulatory elements can include an operator sequence to control transcription. The ability to replicate in a host, usually conferred by an origin of replication, and a selection gene to facilitate recognition of transformants can additionally be incorporated. DNA regions are "operatively linked" when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. In some embodiments, structural elements intended for use in yeast expression systems include a leader sequence enabling extracellular secretion of translated protein by a host cell. In some embodiments, in situations where recombinant protein is expressed without a leader or transport sequence, a polypeptide may include an N-terminal methionine residue. This residue can optionally be subsequently cleaved from the expressed recombinant protein to provide a final product.

The choice of an expression control sequence and an expression vector generally depends upon the choice of host. A wide variety of expression host/vector combinations can be employed. Useful expression vectors for eukaryotic hosts include, for example, vectors comprising expression control sequences from SV40, bovine papilloma virus, adenovirus, and cytomegalovirus. Useful expression vectors for bacterial hosts include known bacterial plasmids, such as plasmids from *E. coli*, including pCR1, pBR322, µMB9 and their derivatives, and wider host range plasmids, such as M13 and other filamentous single-stranded DNA phages.

The ANGPTL8-binding agents (e.g., antibodies) of the present disclosure can be expressed from one or more vectors. For example, in some embodiments, a heavy chain polypeptide is expressed by one vector and a light chain polypeptide is expressed by a second vector. In some embodiments, a heavy chain polypeptide and a light chain polypeptide are expressed by one vector.

Suitable host cells for expression of an ANGPTL8-binding agent (e.g., an antibody) or an ANGPTL8 protein or fragment thereof to use as an antigen or immunogen include prokaryotes, yeast cells, insect cells, or higher eukaryotic cells under the control of appropriate promoters. Prokaryotes include gram-negative or gram-positive organisms, for example *E. coli* or *Bacillus*. Higher eukaryotic cells include established cell lines of mammalian origin as described herein. Cell-free translation systems may also be employed. Appropriate cloning and expression vectors for use with bacterial, fungal, yeast, and mammalian cellular hosts, as well as methods of protein production, including antibody production are well known in the art.

Various mammalian culture systems may be used to express recombinant polypeptides. Expression of recombinant proteins in mammalian cells may be desirable because these proteins are generally correctly folded, appropriately modified, and biologically functional. Examples of suitable mammalian host cell lines include, but are not limited to, COS-7 (monkey kidney-derived), L-929 (murine fibroblast-derived), C127 (murine mammary tumor-derived), 3T3 (murine fibroblast-derived), CHO (Chinese hamster ovary-derived), HeLa (human cervical cancer-derived), BHK (hamster kidney fibroblast-derived), HEK-293 (human embryonic kidney-derived) cell lines and variants thereof. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences.

Expression of recombinant proteins in insect cell culture systems (e.g., baculovirus) also offers a robust method for producing correctly folded and biologically functional proteins. Baculovirus systems for production of heterologous proteins in insect cells are well-known to those of skill in the art.

Thus, the present disclosure provides cells comprising the ANGPTL8-binding agents described herein. In some embodiments, the cells produce the ANGPTL8-binding agents described herein. In some embodiments, the cells produce an antibody. In some embodiments, the cells produce an antibody that binds human ANGPTL8. In some embodiments, the cells produce an antibody that binds cyno ANGPTL8. In some embodiments, the cells produce an antibody that binds human ANGPTL8 and cyno ANGPTL8. In some embodiments, the cells produce an antibody designated 1E5. In some embodiments, the cells produce a humanized version of antibody 1E5, referred to as Hz1E5 or Hz1E5.A1. In some embodiments, the cells produce an antibody designated 1E9. In some embodiments, the cells produce an antibody designated 1A8. In some embodiments, the cell is a hybridoma cell. In some embodiments, the cell is a mammalian cell. In some embodiments, the cell is a prokaryotic cell. In some embodiments, the cell is an eukaryotic cell.

Proteins produced by a host cell can be purified according to any suitable method. Standard methods include chromatography (e.g., ion exchange, affinity, and sizing column chromatography), centrifugation, differential solubility, or by any other standard technique for protein purification. Affinity tags such as hexa-histidine, maltose binding domain, influenza coat sequence, and glutathione-S-transferase can be attached to the protein to allow easy purification by passage over an appropriate affinity column Affinity chromatography used for purifying immunoglobulins can include Protein A, Protein G, and Protein L chromatography. Isolated proteins can be physically characterized using such techniques as proteolysis, size exclusion chromatography (SEC), mass spectrometry (MS), nuclear magnetic resonance (NMR), isoelectric focusing (IEF), high performance liquid chromatography (HPLC), and x-ray crystallography. The purity of isolated proteins can be determined using techniques known to those of skill in the art, including but not limited to, SDS-PAGE, SEC, capillary gel electrophoresis, IEF, and capillary isoelectric focusing (cIEF).

In some embodiments, supernatants from expression systems which secrete recombinant protein into culture media are first concentrated using a commercially available protein concentration filter, for example, an Amicon or Millipore Pellicon ultrafiltration unit. Following the concentration step, the concentrate can be applied to a suitable purification matrix. In some embodiments, an anion exchange resin is employed, for example, a matrix or substrate having pendant diethylaminoethyl (DEAE) groups. The matrices can be acrylamide, agarose, dextran, cellulose, or other types commonly employed in protein purification. In some embodiments, a cation exchange step is employed. Suitable cation exchangers include various insoluble matrices comprising sulfopropyl or carboxymethyl groups. In some embodiments, a hydroxyapatite media is employed, including but not limited to, ceramic hydroxyapatite (CHT). In some embodiments, one or more reverse-phase HPLC steps employing hydrophobic RP-HPLC media, e.g., silica gel having pendant methyl or other aliphatic groups, are employed to further purify a recombinant protein (e.g., an ANGPTL-binding agent). Some or all of the foregoing purification steps, in various combinations, can be employed to provide a homogeneous recombinant protein.

Anti-ANGPTL8 antibodies of the present disclosure may be analyzed for their physical/chemical properties and/or biological activities by various assays known in the art. In some embodiments, an anti-ANGPTL8 antibody is tested for its ability to bind ANGPTL8. Binding assays include, but are not limited to, BIACORE, ELISA, and FACS. In some embodiments, an anti-ANGPTL8 antibody is tested for its ability to inhibit, reduce, or block ANGPTL8 activity.

In some embodiments, monoclonal antibodies generated against ANGPTL8 are grouped based upon the epitope each individual antibody recognizes, a process known as "epitope binning" Generally, in epitope binning antibodies are tested in a pairwise combinatorial manner and antibodies that compete with each other are grouped together into bins. For example, in a premix binning assay, a first antibody is immobilized on a surface and a premixed solution of the second antibody and antigen is flowed over the immobilized first antibody. In tandem, the target protein is immobilized on a surface and the two antibodies are flowed over the immobilized antigen and compete to bind. In each of these techniques, antibodies that block one another can be identified. A competitive blocking profile is created for each antibody relative to the others. The blocking results determine which bin each antibody is placed in. High-throughput methods of epitope binning are known in the art and allow for screening and characterization of large numbers of antibodies within a short period of time. Antibodies that bind similar epitopes often share a similar function. Conversely, antibodies that bind different epitopes may have different functional activities.

Epitope mapping is the process of identifying the binding site, or epitope on a target protein where an antibody (or other binding agent) binds. A variety of methods are known in the art for mapping epitopes on target proteins. These methods include mutagenesis, including but not limited to, shotgun mutagenesis, site-directed mutagenesis, and alanine scanning; domain or fragment scanning, peptide scanning (e.g., pepscan); display methods (e.g., phage display, microbial display, and ribosome/mRNA display); methods involving proteolysis and mass spectroscopy; and structural determination (e.g., x-ray crystallography and NMR).

In some embodiments, purified anti-ANGPTL8 antibodies are characterized by assays including, but not limited to, N-terminal sequencing, amino acid analysis, high pressure liquid chromatography (HPLC), mass spectrometry, ion exchange chromatography, and papain digestion.

In some embodiments, assays are provided for identifying anti-ANGPTL8 antibodies or antigen-binding fragments thereof that affect ANGPTL8 activity. For example, overexpression of ANGPTL8 has been shown to increase triglyceride levels in vivo models. Thus, in some embodiments, candidate ANGPTL8-binding agents are screened for their ability to lower, reduce, or block ANGPTL8-induced increases in triglyceride levels. Clearance of plasma triglycerides is primarily mediated by the activity of lipoprotein lipase (LPL). Studies have suggested that ANGPTL8 is involved, either directly or indirectly, in regulation of LPL activity. Thus, in some embodiments, candidate ANGPTL8-binding agents (e.g., antibodies) are screened for their ability to affect LPL activity (e.g, enhance or increase LPL activity).

The present disclosure also provides conjugates comprising any one of the anti-ANGPTL8 antibodies described herein. In some embodiments, the antibody is attached to a second molecule. In some embodiments, the antibody is conjugated to a cytotoxic agent or moiety. In some embodiments, the antibody is conjugated to a cytotoxic agent to form an ADC (antibody-drug conjugate). In some embodiments, the cytotoxic moiety is a chemotherapeutic agent including, but not limited to, methotrexate, adriamycin/doxorubicin, melphalan, mitomycin C, chlorambucil, duocarmycin, daunorubicin, pyrrolobenzodiazepines (PBDs), or other intercalating agents. In some embodiments, the cytotoxic moiety is a microtubule inhibitor including, but not limited to, auristatins, maytansinoids (e.g., DMI and DM4), and tubulysins. In some embodiments, the cytotoxic moiety is an enzymatically active toxin of bacterial, fungal, plant, or animal origin, or fragments thereof, including, but not limited to, diphtheria A chain, non-binding active fragments of diphtheria toxin, exotoxin A chain, ricin A chain, abrin A chain, modeccin A chain, alpha-sarcin, Aleurites fordii proteins, dianthin proteins, Phytolaca americana proteins (PAPI, PAPII, and PAP-S), Momordica charantia inhibitor, curcin, crotin, Sapaonaria officinalis inhibitor, gelonin, mitogellin, restrictocin, phenomycin, enomycin, and the tricothecenes. In some embodiments, an antibody is conjugated to one or more small molecule toxins, such as calicheamicins, maytansinoids, trichothenes, and CC1065. The derivatives of these toxins that retain cytotoxic activity can also be used.

In some embodiments, the antibody is conjugated to a radioisotope to produce a radioconjugate or a radioconjugated antibody. A variety of radionuclides are available for the production of radioconjugated antibodies including, but not limited to, $^{90}$Y, $^{125}$I, $^{131}$I, $^{123}$I, $^{111}$In, $^{131}$In, $^{105}$Rh, $^{153}$Sm, $^{67}$Cu, $^{67}$Ga, $^{166}$Ho, $^{177}$Lu, $^{186}$Re, $^{188}$Re and $^{212}$Bi.

Conjugates comprising an antibody may be made using any suitable method known in the art. In some embodiments, conjugates are made using a variety of bifunctional protein-coupling agents such as N-succinimidyl-3-(2-pyridyidithiol) propionate (SPDP), iminothiolane (IT), bifunctional derivatives of imidoesters (such as dimethyl adipimidate HC1), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

In some embodiments, antibodies are conjugated to detectable substances or molecules that allow the antibodies to be used for diagnosis and/or detection. The detectable substances may include but not limited to, enzymes, such as horseradish peroxidase, alkaline phosphatase, beta-galactosidase, and acetylcholinesterase; prosthetic groups, such as streptavidin/biotin and avidin/biotin; fluorescent materials, such as, umbelliferone, fluorescein, fluorescein isothiocynate, rhodamine, dichlorotriazinylamine fluorescein, dansyl chloride, and phycoerythrin; bioluminescent materials, such as luciferase, luciferin, and aequorin; chemiluminescent materials, such as luminol and acridinium; radioactive materials, such as $^{131}$I, $^{125}$I, $^{123}$I, and $^{121}$I, and $^{121}$I, $^{14}$C, $^{35}$S, $^{3}$H, $^{115}$In, $^{113}$In, $^{112}$In, and $^{111}$In., $^{99}$T), thallium $^{201}$Ti, $^{68}$Ga, $^{67}$Ga, $^{103}$Pd, $^{99}$Mo, $^{133}$Xe, $^{18}$F, $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Sn; positron emitting metals; and non-radioactive paramagnetic metal ions.

An antibody provided herein can also be conjugated to a second antibody to form an antibody heteroconjugate.

Antibodies that bind ANGPTL8 as described herein may also be attached to solid supports, which are particularly useful for immunoassays or purification of the target antigen. Such solid supports include, but are not limited to, glass, cellulose, polyacrylamide, nylon, polystyrene, polyvinyl chloride, or polypropylene.

III. Polynucleotides

In some embodiments, the disclosure encompasses polynucleotides comprising polynucleotides that encode an ANGPTL8-binding agent described herein. The term "polynucleotides that encode a polypeptide" encompasses a polynucleotide which includes only coding sequences for the polypeptide as well as a polynucleotide which includes additional coding and/or non-coding sequences. The polynucleotides of the disclosure can be in the form of RNA or in the form of DNA. DNA includes cDNA, genomic DNA, and synthetic DNA; and can be double-stranded or single-stranded, and if single stranded can be the coding strand or non-coding (anti-sense) strand.

In some embodiments, the polynucleotide comprises a polynucleotide (e.g., a nucleotide sequence) encoding a polypeptide comprising an amino acid sequence selected from the group consisting of: SEQ ID NOs:35, 36, 44, 45, 56, 57, 62, 63, 64, and 65. In some embodiments, the polynucleotide comprises a polynucleotide (e.g., a nucleotide sequence) encoding a polypeptide comprising more than one amino acid sequence selected from the group consisting of: SEQ ID NOs:35, 36, 44, 45, 56, 57, 62, 63, 64, and 65.

In some embodiments, a polynucleotide comprises a polynucleotide having a nucleotide sequence at least about 80% identical, at least about 85% identical, at least about 90% identical, at least about 95% identical, and in some embodiments, at least about 96%, 97%, 98%, or 99% identical to a polynucleotide encoding an amino acid sequence selected from the group consisting of: SEQ ID NOs:35, 36, 44, 45, 56, 57, 62, 63, 64, and 65. Also provided is a polynucleotide that comprises a polynucleotide that hybridizes to a polynucleotide encoding an amino acid sequence selected from the group consisting of: SEQ ID NOs:35, 36, 44, 45, 56, 57, 62, 63, 64, and 65. In some embodiments, the hybridization is under conditions of high stringency as is known to those skilled in the art.

In some embodiments, a polynucleotide comprises the coding sequence for a polypeptide (e.g., an antibody) fused in the same reading frame to a polynucleotide which aids, for example, in expression and secretion of a polypeptide from a host cell (e.g., a leader sequence which functions as a secretory sequence for controlling transport of a polypeptide). The polypeptide can have the leader sequence cleaved by the host cell to form a "mature" form of the polypeptide.

In some embodiments, a polynucleotide comprises the coding sequence for a polypeptide (e.g., an antibody) fused in the same reading frame to a marker or tag sequence. For example, in some embodiments, a marker sequence is a hexa-histidine tag supplied by a vector which allows efficient purification of the polypeptide fused to the marker in the case of a bacterial host. In some embodiments, a marker sequence is a hemagglutinin (HA) tag derived from the influenza hemagglutinin protein when a mammalian host (e.g., COS-7 cells) is used. In some embodiments, the marker sequence is a FLAG-tag, a peptide of sequence DYKDDDDK (SEQ ID NO:66). In some embodiments, a marker may be used in conjunction with other affinity tags.

The present disclosure further relates to variants of the polynucleotides described herein, wherein the variant encodes, for example, fragments, analogs, and/or derivatives of a polypeptide. In some embodiments, the present disclosure provides a polynucleotide comprising a polynucleotide having a nucleotide sequence at least about 80% identical, at least about 85% identical, at least about 90% identical, at least about 95% identical, and in some embodiments, at least about 96%, 97%, 98% or 99% identical to a polynucleotide encoding a polypeptide comprising an ANGPTL8-binding agent described herein.

As used herein, the phrase "a polynucleotide having a nucleotide sequence at least, for example, 95% "identical" to a reference nucleotide sequence" is intended to mean that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments, a polynucleotide variant contains alterations which produce silent substitutions, additions, or deletions, but does not alter the properties or activities of the encoded polypeptide. In some embodiments, a polynucleotide variant comprises silent substitutions that results in no change to the amino acid sequence of the polypeptide (due to the degeneracy of the genetic code). Polynucleotide variants can be produced for a variety of reasons, for example, to optimize codon expression for a particular host (i.e., change codons in the human mRNA to those preferred by a bacterial host such as *E. coli*). In some embodiments, a polynucleotide variant comprises at least one silent mutation in a non-coding or a coding region of the sequence.

In some embodiments, a polynucleotide variant is produced to modulate or alter expression (or expression levels) of the encoded polypeptide. In some embodiments, a polynucleotide variant is produced to increase expression of the encoded polypeptide. In some embodiments, a polynucleotide variant is produced to decrease expression of the encoded polypeptide. In some embodiments, a polynucleotide variant has increased expression of the encoded polypeptide as compared to a parental polynucleotide sequence. In some embodiments, a polynucleotide variant has decreased expression of the encoded polypeptide as compared to a parental polynucleotide sequence.

In some embodiments, the polynucleotides are isolated. In some embodiments, the polynucleotides are substantially pure.

Vectors and cells comprising the polynucleotides described herein are also provided. In some embodiments, an expression vector comprises a polynucleotide molecule.

In some embodiments, a host cell comprises an expression vector comprising the polynucleotide molecule. In some embodiments, a host cell comprises a polynucleotide molecule.

IV. Methods of Use and Pharmaceutical Compositions

The ANGPTL8-binding agents (e.g., antibodies or antigen-binding fragments thereof) of the disclosure are useful in a variety of applications including, but not limited to, therapeutic treatment methods, such as treatment of diseases or disorders associated with elevated triglycerides. In some embodiments, an ANGPTL8-binding agent described herein is useful in methods for reducing or lowering triglyceride levels. In some embodiments, an ANGPTL8-binding agent described herein is useful in methods for reducing or lowering LDL-cholesterol levels. In some embodiments, an ANGPTL8-binding agent described herein is useful in methods for increasing HDL-cholesterol levels. In some embodiments, an ANGPTL8-binding agent described herein is useful in methods for lowering triglycerides levels and increasing HDL-cholesterol levels. In some embodiments, an ANGPTL8-binding agent described herein is useful in methods for reducing or lowering ANGPTL8 levels (e.g., ANGPTL8 levels in the blood). In some embodiments, an ANGPTL8-binding agent described herein is useful in methods for inhibiting ANGPTL8 activity.

In some embodiments, a method of lowering triglyceride levels in a subject comprises administering to the subject an ANGPTL8-binding agent described herein. In some embodiments, a method of lowering triglyceride levels in a subject comprises administering to the subject a therapeutically effective amount of an anti-ANGPTL8 antibody described herein. In some embodiments, a method of lowering triglyceride levels in a subject comprises administering to the subject a therapeutically effective amount of an antibody that specifically binds ANGPTL8. In some embodiments, a method of lowering triglyceride levels in a subject comprises administering to the subject a therapeutically effective amount of an antibody that specifically binds ANGPTL8, wherein the antibody comprises one, two, three, four, five, and/or six CDRs provided in Tables 1-3. In some embodiments, a method of lowering triglyceride levels in a subject comprises administering to the subject a therapeutically effective amount of an antibody that specifically binds ANGPTL8, wherein the antibody comprises one, two, three, four, five, and/or six CDRs of antibody 1E5. In some embodiments, a method of lowering triglyceride levels in a subject comprises administering to the subject a therapeutically effective amount of an antibody that specifically binds ANGPTL8, wherein the antibody is antibody Hz1E5.

In some embodiments, a method of treating a disease or disorder associated with elevated triglyceride levels in a subject comprises administering to the subject an ANGPTL8-binding agent described herein. In some embodiments, a method of treating a disease or disorder associated with elevated triglyceride levels in a subject comprises administering to the subject a therapeutically effective amount of an anti-ANGPTL8 antibody described herein. In some embodiments, a method of treating a disease or disorder associated with elevated triglyceride levels in a subject comprises administering to the subject a therapeutically effective amount of an antibody that specifically binds ANGPTL8. In some embodiments, a method of treating a disease or disorder associated with elevated triglyceride levels in a subject comprises administering to the subject a therapeutically effective amount of an antibody that specifically binds ANGPTL8, wherein the antibody comprises one, two, three, four, five, and/or six CDRs provided in Tables 1-3. In some embodiments, a method of treating a disease or disorder associated with elevated triglyceride levels in a subject comprises administering to the subject a therapeutically effective amount of an antibody that specifically binds ANGPTL8, wherein the antibody comprises one, two, three, four, five, and/or six CDRs of antibody 1E5. In some embodiments, a method of treating a disease or disorder associated with elevated triglyceride levels in a subject comprises administering to the subject a therapeutically effective amount of an antibody that specifically binds ANGPTL8, wherein the antibody is antibody Hz1E5.

In some embodiments, a method of treating a subject diagnosed with a disease or disorder associated with elevated triglyceride levels comprises administering to the subject an ANGPTL8-binding agent described herein. In some embodiments, a method of treating a subject diagnosed with a disease or disorder associated with elevated triglyceride levels comprises administering to the subject a therapeutically effective amount of an anti-ANGPTL8 antibody described herein. In some embodiments, a method of treating a subject diagnosed with a disease or disorder associated with elevated triglyceride levels comprises administering to the subject a therapeutically effective amount of an antibody that specifically binds ANGPTL8. In some embodiments, a method of treating a subject diagnosed with a disease or disorder associated with elevated triglyceride levels comprises administering to the subject a therapeutically effective amount of an antibody that specifically binds ANGPTL8, wherein the antibody comprises one, two, three, four, five, and/or six CDRs provided in Tables 1-3. In some embodiments, a method of treating a subject diagnosed with a disease or disorder associated with elevated triglyceride levels comprises administering to the subject a therapeutically effective amount of an antibody that specifically binds ANGPTL8, wherein the antibody comprises one, two, three, four, five, and/or six CDRs of antibody 1E5. In some embodiments, a method of treating a subject diagnosed with a disease or disorder associated with elevated triglyceride levels comprises administering to the subject a therapeutically effective amount of an antibody that specifically binds ANGPTL8, wherein the antibody is antibody Hz1E5.

In some embodiments, a method of treating a subject having symptoms of a disease or disorder associated with elevated triglyceride levels comprises administering to the subject an ANGPTL8-binding agent described herein. In some embodiments, a method of treating a subject having symptoms of a disease or disorder associated with elevated triglyceride levels comprises administering to the subject a therapeutically effective amount of an anti-ANGPTL8 antibody described herein. In some embodiments, a method of treating a subject having symptoms of a disease or disorder associated with elevated triglyceride levels comprises administering to the subject a therapeutically effective amount of an antibody that specifically binds ANGPTL8. In some embodiments, a method of treating a subject having symptoms of a disease or disorder associated with elevated triglyceride levels comprises administering to the subject a therapeutically effective amount of an antibody that specifically binds ANGPTL8, wherein the antibody comprises one, two, three, four, five, and/or six CDRs provided in Tables 1-3. In some embodiments, a method of treating a subject having symptoms of a disease or disorder associated with elevated triglyceride levels comprises administering to the subject a therapeutically effective amount of an antibody that specifically binds ANGPTL8, wherein the antibody comprises one, two, three, four, five, and/or six CDRs of antibody 1E5. In some embodiments, a method of treating a subject having symptoms of a disease or disorder associated with elevated triglyceride levels comprises administering to the subject a therapeutically effective amount of an antibody that specifically binds ANGPTL8, wherein the antibody is antibody Hz1E5.

In some embodiments, a method of preventing elevated triglyceride levels in a subject comprises administering to the subject an ANGPTL8-binding agent described herein. In some embodiments, a method of preventing elevated triglyceride levels in a subject comprises administering to the subject a therapeutically effective amount of an anti-ANGPTL8 antibody described herein. In some embodiments, a method of preventing elevated triglyceride levels in a subject comprises administering to the subject a therapeutically effective amount of an antibody that specifically binds human ANGPTL8. In some embodiments, a method of preventing elevated triglyceride levels in a subject comprises administering to the subject a therapeutically effective amount of an antibody that specifically binds human ANGPTL8, wherein the antibody comprises one, two, three, four, five, and/or six CDRs provided in Tables 1-3. In some embodiments, a method of preventing elevated triglyceride levels in a subject comprises administering to the subject a therapeutically effective amount of an antibody that specifically binds human ANGPTL8, wherein the antibody comprises one, two, three, four, five, and/or six CDRs of antibody 1E5. In some embodiments, a method of preventing elevated triglyceride levels in a subject comprises administering to the subject a therapeutically effective amount of an antibody that specifically binds human ANGPTL8, wherein the antibody is antibody Hz1E5.

In some embodiments, a method of preventing a disease or disorder associated with elevated triglyceride levels in a subject comprises administering to the subject an ANGPTL8-binding agent described herein. In some embodiments, a method of preventing a disease or disorder associated with elevated triglyceride levels in a subject comprises administering to the subject a therapeutically effective amount of an anti-ANGPTL8 antibody described herein. In some embodiments, a method of preventing a disease or disorder associated with elevated triglyceride levels in a subject comprises administering to the subject a therapeutically effective amount of an antibody that specifically binds human ANGPTL8. In some embodiments, a method of preventing a disease or disorder associated with elevated triglyceride levels in a subject comprises administering to the subject a therapeutically effective amount of an antibody that specifically binds human ANGPTL8, wherein the antibody comprises one, two, three, four, five, and/or six CDRs provided in Tables 1-3. In some embodiments, a method of preventing a disease or disorder associated with elevated triglyceride levels in a subject comprises administering to the subject a therapeutically effective amount of an antibody that specifically binds human ANGPTL8, wherein the antibody comprises one, two, three, four, five, and/or six CDRs of antibody 1E5. In some embodiments, a method of preventing a disease or disorder associated with elevated triglyceride levels in a subject comprises administering to the subject a therapeutically effective amount of an antibody that specifically binds human ANGPTL8, wherein the antibody is antibody Hz1E5.

In some embodiments, a method of treating a subject at risk for elevated triglyceride levels comprises administering to the subject an ANGPTL8-binding agent described herein. In some embodiments, a method of treating a subject at risk for elevated triglyceride levels comprises administering to the subject a therapeutically effective amount of an anti-ANGPTL8 antibody described herein. In some embodiments, a method of treating a subject at risk for elevated triglyceride levels comprises administering to the subject a therapeutically effective amount of an antibody that specifically binds human ANGPTL8. In some embodiments, a method of treating a subject at risk for elevated triglyceride levels comprises administering to the subject a therapeutically effective amount of an antibody that specifically binds human ANGPTL8, wherein the antibody comprises one, two, three, four, five, and/or six CDRs provided in Tables 1-3. In some embodiments, a method of treating a subject at risk for elevated triglyceride levels comprises administering to the subject a therapeutically effective amount of an antibody that specifically binds human ANGPTL8, wherein the antibody comprises one, two, three, four, five, and/or six CDRs of antibody 1E5. In some embodiments, a method of treating a subject at risk for elevated triglyceride levels comprises administering to the subject a therapeutically effective amount of an antibody that specifically binds human ANGPTL8, wherein the antibody is antibody Hz1E5.

In some embodiments, a method of treating a subject at risk for a disease or disorder associated with elevated triglyceride levels comprises administering to the subject an ANGPTL8-binding agent described herein. In some embodiments, a method of treating a subject at risk for a disease or disorder associated with elevated triglyceride levels comprises administering to the subject a therapeutically effective amount of an anti-ANGPTL8 antibody described herein. In some embodiments, a method of treating a subject at risk for a disease or disorder associated with elevated triglyceride levels comprises administering to the subject a therapeutically effective amount of an antibody that specifically binds human ANGPTL8. In some embodiments, a method of treating a subject at risk for a disease or disorder associated with elevated triglyceride levels comprises administering to the subject a therapeutically effective amount of an antibody that specifically binds human ANGPTL8, wherein the antibody comprises one, two, three, four, five, and/or six CDRs provided in Tables 1-3. In some embodiments, a method of treating a subject at risk for a disease or disorder associated with elevated triglyceride levels comprises administering to the subject a therapeutically effective amount of an antibody that specifically binds human ANGPTL8, wherein the antibody comprises one, two, three, four, five, and/or six CDRs of antibody 1E5. In some embodiments, a method of treating a subject at risk for a disease or disorder associated with elevated triglyceride levels comprises administering to the subject a therapeutically effective amount of an antibody that specifically binds human ANGPTL8, wherein the antibody is antibody Hz1E5.

In some embodiments, a method of reducing ANGPTL8 levels in a subject wherein the ANGPTL8 levels are elevated, the method comprising administering to the subject an ANGPTL8-binding agent described herein. In some embodiments, a method of reducing ANGPTL8 levels in a subject wherein the ANGPTL8 levels are elevated, the method comprising administering to the subject a therapeutically effective amount of an anti-ANGPTL8 antibody described herein. In some embodiments, a method of reducing ANGPTL8 levels in a subject wherein the ANGPTL8 levels are elevated, the method comprising administering to the subject a therapeutically effective amount of an antibody that specifically binds human ANGPTL8. In some embodiments, a method of reducing ANGPTL8 levels in a subject wherein the ANGPTL8 levels are elevated, the method comprising administering to the subject a therapeutically effective amount of an antibody that specifically binds human ANGPTL8, wherein the antibody comprises one, two, three, four, five, and/or six CDRs provided in Tables 1-3. In some embodiments, a method of reducing ANGPTL8 levels in a subject wherein the ANGPTL8 levels are elevated, the method comprising administering to the subject a therapeutically effective amount of an antibody that specifically binds human ANGPTL8, wherein the antibody comprises one, two, three, four, five, and/or six CDRs of antibody 1E5. In some embodiments, a method of reducing ANGPTL8 levels in a subject wherein the ANGPTL8 levels are elevated, the method comprising administering to the subject a therapeutically effective amount of an antibody that specifically binds human ANGPTL8, wherein the antibody is antibody Hz1E5. In some embodiments, the method of reducing ANGPTL8 levels results in the lowering of triglycerides in the subject. In some embodiments, the method of reducing ANGPTL8 levels results in the prevention of elevated triglycerides in the subject.

In some embodiments, a method of inhibiting ANGPTL8 activity in a subject comprises administering to the subject an ANGPTL8-binding agent described herein. In some embodiments, a method of inhibiting ANGPTL8 activity in a subject comprises administering to the subject a therapeutically effective amount of an anti-ANGPTL8 antibody described herein. In some embodiments, a method of inhibiting ANGPTL8 activity in a subject comprises administering to the subject a therapeutically effective amount of an antibody that specifically binds human ANGPTL8. In some embodiments, a method of inhibiting ANGPTL8 activity in a subject comprises administering to the subject a therapeutically effective amount of an antibody that specifically binds human ANGPTL8, wherein the antibody comprises one, two, three, four, five, and/or six CDRs provided in Tables 1-3. In some embodiments, a method of inhibiting ANGPTL8 activity in a subject comprises administering to the subject a therapeutically effective amount of an antibody that specifically binds human ANGPTL8, wherein the antibody comprises one, two, three, four, five, and/or six CDRs of antibody 1E5. In some embodiments, a method of inhibiting ANGPTL8 activity in a subject comprises administering to the subject a therapeutically effective amount of an antibody that specifically binds human ANGPTL8, wherein the antibody is antibody Hz1E5. In some embodiments, the method of inhibiting ANGPTL8 activity results in the lowering of triglycerides in the subject. In some embodiments, the method of inhibiting ANGPTL8 activity results in the prevention of elevated triglycerides in the subject.

In some embodiments of the methods described herein, the disease or disorder associated with elevated triglyceride levels is metabolic syndrome, atherosclerosis, obesity, diabetes, cardiovascular disease, hyperlipidemia, hypertriglyceridemia, pancreatitis, renal disease, liver disease, or hypothyroidism.

In some embodiments of the methods described herein, the disease or disorder associated with elevated triglyceride levels is cardiovascular disease. Cardiovascular disease may include, but is not limited to, atherosclerosis, aneurysm, hypertension, angina, stroke, cerebrovascular diseases, congestive heart failure, coronary artery diseases, myocardial infarction, and peripheral vascular diseases. In some embodiments, the disease or disorder associated with elevated triglyceride levels is atherosclerosis.

In some embodiments, the disease or disorder associated with elevated triglyceride levels is dyslipidemia, atherogenic dyslipidemia, diabetic dyslipidemia, hypercholesterolemia, chylomicronemia, mixed dyslipidemia, lipodystrophy, or lipoatrophy.

In some embodiments, the disease or disorder associated with elevated triglyceride levels is hyperlipoproteinemia. There are several type of hyperlipoproteinemia, including primary and secondary hyperlipoproteinemia. Primary hyperlipoproteinemia, is often due to one or more familial or genetic conditions. Persistent hypertriglyceridemia, including hypertriglyceridemia that persists despite treatment of the underlying condition, may be associated with or caused by a primary form of hyperlipoproteinemia, such as familial hypertriglyceridemia. Additional familial conditions associated with elevated triglyceride levels include familial combined lipidemia and familial dysbetalipoproteinemia (Type III hyperlipoproteinemia). Secondary hyperlipoproteinemia is associated with, and a compounding factor of, several conditions, such as obesity, diabetes, renal disease, liver disease, pancreatitis, hypothyroidism, and alcoholism.

In some embodiments of the methods described herein, elevated triglyceride levels may be due to increased production and/or decreased elimination of very low-density lipoprotein (VLDL). In some embodiments, elevated triglyceride levels may be due to certain drug treatments, including but not limited to, beta blockers, birth control pills, estrogens, diuretics, steroids, tamoxifen, miconazole, spironolactone, isotretinoin (ACCUTANE), quinapril, or mirtazapine. In some embodiments of the methods described herein, elevated triglyceride levels may be due to genetic predisposition. In some embodiments of the methods described herein, elevated triglyceride levels may be due to diet and/or life style. In some embodiments, elevated triglyceride levels may be due to acute stress associated conditions. Acute stress associated states include but are not limited to, burns, trauma, myocardial infarction, and sepsis.

In some embodiments of the methods described herein, the elevated triglyceride levels are elevated blood or plasma triglyceride levels. It is generally accepted that a normal triglyceride level is less than 150 mg/dL (or less than 1.7 mmol/L). In some embodiments of the methods described herein, the elevated plasma triglyceride level is 150 mg/dL or higher. In some embodiments, the elevated plasma triglyceride level is about 150 to about 200 mg/dL. In some embodiments, the elevated plasma triglyceride level is about 200 to about 500 mg/dL. In some embodiments, the elevated plasma triglyceride level is about 500 or higher.

In some embodiments of the methods described herein, after administration of an anti-ANGPTL8 antibody the elevated triglyceride level is reduced by at least 5% as compared to triglyceride levels in the subject prior to the administration of the antibody. In some embodiments, the elevated triglyceride level is reduced by at least 10% as compared to triglyceride levels in the subject prior to the administration of the antibody. In some embodiments, the elevated triglyceride level is reduced by about 10-15% as compared to triglyceride levels in the subject prior to the administration of the antibody. In some embodiments, the elevated triglyceride level is reduced by about 10-20% as compared to triglyceride levels in the subject prior to the administration of the antibody. In some embodiments, the elevated triglyceride level is reduced by about 20-30% as compared to triglyceride levels in the subject prior to the administration of the antibody. In some embodiments, the elevated triglyceride level is reduced by more than 25% as compared to triglyceride levels in the subject prior to the administration of the antibody.

In some embodiments, a method of increasing HDL-cholesterol levels in a subject is provided. In some embodiments, a method of increasing HDL-cholesterol levels in a subject comprises administering to the subject an ANGPTL8-binding agent described herein. In some embodiments, a method of increasing HDL-cholesterol levels in a subject comprises administering to the subject a therapeutically effective amount of an anti-ANGPTL8 antibody described herein. In some embodiments, a method of increasing HDL-cholesterol levels in a subject comprises administering to the subject a therapeutically effective amount of an antibody that specifically binds human ANGPTL8. In some embodiments, a method of increasing HDL-cholesterol levels in a subject comprises administering to the subject a therapeutically effective amount of an antibody that specifically binds ANGPTL8, wherein the antibody comprises one, two, three, four, five, and/or six CDRs provided in Tables 1-3. In some embodiments, a method of increasing HDL-cholesterol levels in a subject comprises administering to the subject a therapeutically effective amount of an antibody that specifically binds ANGPTL8, wherein the antibody comprises one, two, three, four, five, and/or six CDRs of antibody 1E5. In some embodiments, a method of increasing HDL-cholesterol levels in a subject comprises administering to the subject a therapeutically effective amount of an antibody that specifically binds ANGPTL8, wherein the antibody is antibody Hz1E5.

It is generally accepted that HDL-cholesterol levels of less than 40 mg/dL are considered a risk for heart disease, levels of 40-59 mg/dl are considered good, and levels of 60 mg/dL or higher are considered to be protective against heart disease. In some embodiments of the methods described herein, HDL-cholesterol levels are increased to 40 mg/dL or above.

In some embodiments of the disclosure, a method of lowering LDL-cholesterol levels in a subject is provided. In some embodiments, a method of lowering LDL-cholesterol levels in a subject comprises administering to the subject an ANGPTL8-binding agent described herein. In some embodiments, a method of lowering LDL-cholesterol levels in a subject comprises administering to the subject a therapeutically effective amount of an anti-ANGPTL8 antibody described herein. In some embodiments, a method of lowering LDL-cholesterol levels in a subject comprises administering to the subject a therapeutically effective amount of an antibody that specifically binds human ANGPTL8. In some embodiments, a method of lowering LDL-cholesterol levels in a subject comprises administering to the subject a therapeutically effective amount of an antibody that specifically binds ANGPTL8, wherein the antibody comprises one, two, three, four, five, and/or six CDRs provided in Tables 1-3. In some embodiments, a method of lowering LDL-cholesterol levels in a subject comprises administering to the subject a therapeutically effective amount of an antibody that specifically binds ANGPTL8, wherein the antibody comprises one, two, three, four, five, and/or six CDRs of antibody 1E5. In some embodiments, a method of lowering LDL-cholesterol levels in a subject comprises administering to the subject a therapeutically effective amount of an antibody that specifically binds ANGPTL8, wherein the antibody is antibody Hz1E5.

It is generally accepted that LDL-cholesterol levels of less than 100 mg/dL are optimal, levels of 100-129 mg/dl are considered near optimal, levels of 130-159 mg/dL are considered borderline high, levels of 160-189 mg/dL are high, and levels of 190 mg/dL or above are very high. In some embodiments of the methods described herein, LDL-cholesterol levels are lowered to below about 190 mg/dL, to below about 160 mg/dL, to below about 130 mg/dL, or to below about 100 mg/dL.

In some embodiments of the methods described herein, the subject is overweight. In some embodiments, the subject is obese. In some embodiments, the subject has diabetes. In some embodiments, the subject has type 2 diabetes. In some embodiments, the subject has cardiovascular disease.

There has been at least one report that ANGPTL8 levels were elevated in patients with liver disease, such as non-alcoholic fatty liver disease (NAFLD) (see, e.g., Lee et al., 2016, Nature Scientific Reports, DOI: 10.1038/srep24013). Thus in some embodiments, a method of treating liver disease in a subject comprises administering to the subject a therapeutically effective amount of an antibody that specifically binds human ANGPTL8. In some embodiments, a method of treating liver disease in a subject comprises administering to the subject a therapeutically effective amount of an antibody that specifically binds ANGPTL8, wherein the antibody comprises one, two, three, four, five, and/or six CDRs provided in Tables 1-3. In some embodiments, a method of treating liver disease in a subject comprises administering to the subject a therapeutically effective amount of an antibody that specifically binds ANGPTL8, wherein the antibody comprises one, two, three, four, five, and/or six CDRs of antibody 1E5. In some embodiments, a method of treating liver disease in a subject comprises administering to the subject a therapeutically effective amount of an antibody that specifically binds ANGPTL8, wherein the antibody is antibody Hz1E5. In some embodiments, the liver disease is NAFLD. In some embodiments, the liver disease is non-alcoholic steatohepatitis (NASH).

In some embodiments of the methods described herein, a method comprises administering an ANGPTL8-binding agent described herein in combination with at least one additional therapeutic agent or therapeutic therapy. Treatment with two or more therapeutic agents often uses agents that work by different mechanisms of action, although this is not required. Combination therapy using agents with different mechanisms of action may result in additive or synergetic effects. Combination therapy may allow for a lower dose of each agent than is used in monotherapy, thereby reducing toxic side effects and/or increasing the therapeutic index of the agent(s). Combination therapy may decrease the likelihood that resistance to an agent will develop.

In some embodiments, the combination of an ANGPTL8-binding agent described herein and at least one additional therapeutic agent results in additive or synergistic results. In some embodiments, the combination therapy results in an increase in the therapeutic index of the ANGPTL8-binding agent. In some embodiments, the combination therapy results in an increase in the therapeutic index of the additional therapeutic agent(s). In some embodiments, the combination therapy results in a decrease in the toxicity and/or side effects of the ANGPTL8-binding agent. In some embodiments, the combination therapy results in a decrease in the toxicity and/or side effects of the additional therapeutic agent(s).

In some embodiments, an additional therapeutic agent can be administered prior to, concurrently with, and/or subsequently to, administration of the ANGPTL8-binding agent. In some embodiments, the at least one additional therapeutic agent comprises 1, 2, 3, or more additional therapeutic agents.

A combination treatment may comprise one additional therapeutic agent or two or more additional therapeutic agents. Treatment with an ANGPTL8-binding agent can occur prior to, concurrently with, or subsequent to administration of the additional therapeutic agents. Combined administration can include co-administration, either in a single pharmaceutical formulation or using separate formulations, or consecutive administration in either order but generally within a time period such that all active agents can exert their biological activities. Preparation and dosing schedules for additional therapeutic agents can be used according to manufacturers' instructions or as determined empirically by the skilled practitioner.

Additional therapeutic agents that may be administered in combination with the ANGPTL8-binding agents described herein include, but are not limited to, fibrates, statins, omega-3 fatty acids, and niacin. In some embodiments, an additional therapeutic agent is a fibrate. Fibrates are a class of amphipathic carboxylic acids and include, but are not limited to, aluminum clofibrate, bezafibrate, ciprofibrate, choline fenofibrae, clinofibrate, clofibrate (e.g., ATROMID-S), clofibride, fenofibrate (e.g., FIBRICOR, LOFIBRA, TRICOR), gemfibrozil (e.g., LOPID), ronifibrate, simfibrate, and fenofibric acid. In some embodiments, an additional therapeutic agent is a statin. Statins are HMG-CoA reductase inhibitors and include, but are not limited to, atorvastatin (LIPITOR), fluvastatin (LESCOL), lovastatin (MEVACOR), pravastatin (PRAVACHOL), rosuvastatin (ZOCOR), and pitavastatin (LIVALO). In some embodiments, the additional therapeutic agent is niacin (vitamin B3). In some embodiments, the additional therapeutic agent is an omega-3 fatty acid.

In some embodiments, an additional therapeutic agent is an obesity drug. Obesity drugs include, but are not limited to, orlistat (XENICAL), phentermine/topiramate (QSYMIA), lorcaserin (BELVIQ), naltrexone/bupropion (CONTRAVE) and liraglutide (SAXENDA).

In some embodiments, an additional therapeutic agent is a diabetes drug. Anti-diabetic drugs include, but are not limited to, insulin; PPAR (peroxisome proliferator-activated receptor) γ-agonists, such as pioglitazone, troglitazone, ciglitazone, rivogli alone, rosiglitazone, and other 2,4-thiazolidinedione derivatives; DPP-4 inhibitors, such as sitagliptin (JANUVIA), vildagliptin, saxagliptin, linagliptin (TRADJENTA), dutogliptin, gemigliptin, and alogliptin (NESINA); GLP-1 analogs, such as exenatide, liraglutide, taspoglutide, albiglutide, and lixisenatide; biguanidine derivatives, such as metformin (GLUMETZA, GLUCOPHAGE), buformin, and phenformin; ATP-sensitive potassium channel modulators, such as mitiglinide, repaglinide, and nateglinide; sulfonylurea derivatives, such as tolbutamide, chlorpropamide, tolazamide, acetohexamide, glipizide, gliclazide, glimepiride, gliquidone, glibornuride, glisoxepid, glibenclamide, glisentide, glisolamide, glybuzole, and glyclopyramide; α-glucosidase inhibitors, such as miglitol (GLYSET), acarbose (PRECOSE), and voglibose; and SGLT2 inhibitors, such as canagliflozin (INVOKANA), dapagliflozin (FARXIGA), and empagliflozin (JARDIANCE).

For the treatment of a disease, the appropriate dosage of an ANGPTL8-binding agent of the present disclosure depends on the disorder or disease to be treated, the severity and course of the disorder or disease, the responsiveness of the disorder or disease, whether the agent is administered for therapeutic or preventative purposes, previous therapy, the patient's clinical history, and so on. The ANGPTL8-binding agent can be administered one time or over a series of treatments lasting from several days to several months, or until a cure is effected or a diminution of the disease state is achieved.

It will be appreciated that the combination of an ANGPTL8-binding agent described herein and at least one additional therapeutic agent may be administered in any order or concurrently. In some embodiments, the ANGPTL8-binding agent is administered to subjects that have previously undergone treatment with a therapeutic agent. In some embodiments, the ANGPTL8-binding agent and a second therapeutic agent is administered substantially simultaneously or concurrently. For example, a subject may be given an ANGPTL8-binding agent while undergoing a course of treatment with a second therapeutic agent (e.g., statins). In some embodiments, an ANGPTL8-binding agent is administered within 1 year of the treatment with a second therapeutic agent. In some embodiments, an ANGPTL8-binding agent is administered within 10, 8, 6, 4, or 2 months of any treatment with a second therapeutic agent. In some embodiments, an ANGPTL8-binding agent is administered within 4, 3, 2, or 1 weeks of any treatment with a second therapeutic agent. In some embodiments, an ANGPTL8-binding agent is administered within 5, 4, 3, 2, or 1 days of any treatment with a second therapeutic agent. It will further be appreciated that the two (or more) agents or treatments may be administered to the subject within a matter of hours or minutes (i.e., substantially simultaneously).

The dose of an ANGPTL8-binding agent described herein may vary depending on the nature and/or severity of the disease or disorder, as well as the condition of the subject. In some embodiments, dosage of the agent is from 0.01 µg to 100 mg/kg of body weight, from 0.1 µg to 100 mg/kg of body weight, from 1 µg to 100 mg/kg of body weight, from 1 mg to 100 mg/kg of body weight, 1 mg to 80 mg/kg of body weight from 10 mg to 100 mg/kg of body weight, from 10 mg to 75 mg/kg of body weight, or from 10 mg to 50 mg/kg of body weight. In some embodiments, dosage of the agent is from about 0.1 mg to about 20 mg/kg of body weight. In some embodiments, dosage of the agent is about 0.5 mg/kg of body weight. In some embodiments, dosage of the agent is about 1 mg/kg of body weight. In some embodiments, dosage of the agent is about 1.5 mg/kg of body weight. In some embodiments, dosage of the agent is about 2 mg/kg of body weight. In some embodiments, dosage of the agent is about 2.5 mg/kg of body weight. In some embodiments, dosage of the agent is about 5 mg/kg of body weight. In some embodiments, dosage of the agent is about 7.5 mg/kg of body weight. In some embodiments, dosage of the agent is about 10 mg/kg of body weight. In some embodiments, dosage of the agent is about 12.5 mg/kg of body weight. In some embodiments, dosage of the agent is about 15 mg/kg of body weight. In some embodiments, the agent is dosed once or more daily, weekly, monthly, or yearly. In some embodiments, the agent is dosed once every week, once every two weeks, once every three weeks, or once every four weeks.

The present disclosure provides compositions comprising an ANGPTL8-binding agent described herein. The present disclosure also provides pharmaceutical compositions comprising an ANGPTL8-binding agent described herein and a pharmaceutically acceptable vehicle.

Formulations are prepared for storage and use by combining a purified antibody or agent of the present disclosure with a pharmaceutically acceptable vehicle (e.g., a carrier or excipient). Those of skill in the art generally consider pharmaceutically acceptable carriers, excipients, and/or stabilizers to be inactive ingredients of a formulation or pharmaceutical composition.

Suitable pharmaceutically acceptable vehicles include, but are not limited to, nontoxic buffers such as phosphate, citrate, and other organic acids; salts such as sodium chloride; antioxidants including ascorbic acid and methionine; preservatives such as octadecyldimethylbenzyl ammonium chloride, hexamethonium chloride, benzalkonium chloride, benzethonium chloride, phenol, butyl or benzyl alcohol, alkyl parabens, such as methyl or propyl paraben, catechol, resorcinol, cyclohexanol, 3-pentanol, and m-cresol; low molecular weight polypeptides (e.g., less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes such as Zn-protein complexes; and non-ionic surfactants such as TWEEN or polyethylene glycol (PEG). (*Remington: The Science and Practice of Pharmacy,* 22$^{nd}$ Edition, 2012, Pharmaceutical Press, London.). In some embodiments, the formulation is in the form of an aqueous solution. In some embodiments, the formulation is lyophilized or in an alternative dried form.

The therapeutic formulation can be in unit dosage form. Such formulations include tablets, pills, capsules, powders, granules, solutions or suspensions in water or non-aqueous media, or suppositories. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and diluents (e.g., water). These can be used to form a solid preformulation composition containing a homogeneous mixture of a compound of the present disclosure, or a non-toxic pharmaceutically acceptable salt thereof. The solid preformulation composition is then subdivided into unit dosage forms of a type described above. The tablets, pills, etc. of the formulation or composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials include a number of polymeric acids and mixtures of polymeric acids with such materials as shellac, cetyl alcohol, and cellulose acetate.

The binding agents of the present disclosure may be formulated in any suitable form for delivery to a target cell/tissue. In some embodiments, an ANGPTL8-binding agent can be formulated as a liposome, microparticle, microcapsule, albumin microsphere, microemulsion, nano-particle, nanocapsule, or macroemulsion. In some embodiments, the pharmaceutical formulation includes an agent of the present disclosure complexed with liposomes. Methods to produce liposomes are known to those of skill in the art. For example, some liposomes can be generated by reverse phase evaporation with a lipid composition comprising phosphatidylcholine, cholesterol, and PEG-derivatized phosphatidylethanolamine (PEG-PE).

In some embodiments, an ANGPTL8-binding agent is formulated as a sustained-release preparation. Suitable examples of sustained-release preparations include semi-permeable matrices of solid hydrophobic polymers containing an agent, where the matrices are in the form of shaped articles (e.g., films or microcapsules). Sustained-release matrices include but are not limited to polyesters, hydrogels such as poly(2-hydroxyethyl-methacrylate) or poly(vinyl alcohol), polylactides, copolymers of L-glutamic acid and 7 ethyl-L-glutamate, non-degradable ethylene-vinyl acetate, degradable lactic acid-glycolic acid copolymers such as the LUPRON DEPOTTM (injectable microspheres composed of lactic acid-glycolic acid copolymer and leuprolide acetate), sucrose acetate isobutyrate, and poly-D-(−)-3-hydroxybutyric acid.

The pharmaceutical compositions or formulations of the present disclosure can be administered in any number of ways for either local or systemic treatment. Administration can be topical by epidermal or transdermal patches, ointments, lotions, creams, gels, drops, suppositories, sprays, liquids and powders; pulmonary by inhalation or insufflation of powders or aerosols, including by nebulizer, intratracheal, and intranasal; oral; or parenteral including intravenous, intraarterial, intratumoral, subcutaneous, intraperitoneal, intramuscular (e.g., injection or infusion), or intracranial (e.g., intrathecal or intraventricular).

Various delivery systems are known and can be used to administer an ANGPTL8-binding agent described herein. In some embodiments, an ANGPTL8-binding agent or a composition described herein can be delivered in a controlled release or sustained release system. In some embodiments, a pump may be used to achieve controlled or sustained release. In some embodiments, polymeric materials can be used to achieve controlled or sustained release of the ANGPTL8-binding agent described herein. Examples of polymers used in sustained release formulations include, but are not limited to, poly 2-hydroxy ethyl methacrylate, polymethyl methacrylate, polyacrylic acid, polyethylene-co-vinyl acetate, polymethacrylic acid, polyglycolides (PLG), polyanhydrides, poly N-vinyl pyrrolidone, polyvinyl alcohol (PVA), polyacrylamide, polyethylene glycol (PEG), polylactides (PLA), polylactide-co-glycolides (PLGA), and polyorthoesters. Any polymer used in a sustained release formulation should be inert, free of leachable impurities, stable on storage, sterile, and biodegradable.

Additional delivery systems can be used to administer an ANGPTL8-binding agent described herein including, but not limited to, injectable drug delivery devices and osmotic pumps. Injectable drug delivery devices include, for example, hand-held devices (e.g., autoinjectors) or wearable devices. Different types of osmotic pump systems may include single compartment systems, dual compartment systems, and multiple compartment systems.

V. Assays and/or Kits Comprising ANGPTL8-Binding Agents

In some embodiments, the anti-ANGPTL8 antibodies and fragments thereof described herein are useful for detecting the presence of ANGPTL8 in a biological sample. Such anti-ANGPTL8 antibodies can include those that bind to human and/or cyno ANGPTL8, but do not inhibit ANGPTL8 activity. The term "detecting" as used herein encompasses quantitative or qualitative detection. In some embodiments, a biological sample comprises a cell, tissue, blood, or other bodily fluid.

In some embodiments, a method of detecting the presence of ANGPTL8 in a biological sample comprises contacting the biological sample with an anti-ANGPTL8 antibody under conditions permissive for binding of the anti-ANGPTL8 antibody to ANGPTL8, and detecting whether a complex is formed between the anti-ANGPTL8 antibody and ANGPTL8. The methods may include assays known by those of skill in the art, such as Western blot analyses, radioimmunoassays, ELISAs (enzyme linked immunosorbent assays), "sandwich" immunoassays, immunoprecipitation assays, fluorescent immunoassays, protein A immunoassays, and immunohistochemistry (IHC).

In some embodiments, the anti-ANGPTL8 antibody is tagged with a detectable label. The detectable label may be a fluorescent molecule, a chemiluminescent molecule, a bioluminescent molecule, an enzyme, or a radioisotope.

The present disclosure provides kits that comprise the ANGPTL8-binding agents described herein and that can be used to perform the methods described herein. In some embodiments, a kit comprises at least one purified ANGPTL8-binding agent in one or more containers. In some embodiments, the kits contain all of the components necessary and/or sufficient to perform a detection assay, including all controls, directions for performing assays, and any necessary software for analysis and presentation of results. One skilled in the art will readily recognize that the disclosed ANGPTL8-binding agents of the present disclosure can be readily incorporated into one of the established kit formats which are well known in the art.

Further provided are kits that comprise an ANGPTL8-binding agent as well as at least one additional therapeutic agent. In some embodiments, the second (or more) therapeutic agent is a fibrate, statin, niacin, and/or 3-omega fatty acid. In some embodiments, the second (or more) therapeutic agent is a second antibody.

EXAMPLES

Example 1

Overexpression of ANGPTL8 and ANGPTL8 Variants in Mice

It has previously been shown that overexpression of both mANGPTL8 and hANGPTL8 in mice significantly increased plasma triglycerides levels (see, e.g., International Publication No. WO 2016/054494). To further define the region(s) of human ANGPTL8 responsible for the increase in triglycerides, variants of human ANGPTL8 with deletions at the N-terminus were generated (FIG. 2A). Recombinant adeno-associated virus (rAAV) vectors expressing human ANGPTL8 or the deletion variants were produced by standard methods. One of skill in the art would know that the signal peptides are processed in vivo and human ANGPTL8 would correspond to SEQ ID NO:2. C57BL/6 mice (5-6 mice per a group) were administered $3 \times 10^{11}$ IU rAAV by tail vein injection in a single dose. An AAV vector expressing green fluorescent protein (AAV-GFP) was used as a control. Twelve days post-injection, blood samples were obtained from tail veins and plasma triglyceride levels were measured. Triglycerides were assayed using a L-Type Triglyceride M kit (Wako Diagnostics) following the manufacturer's instructions.

Figure 2A:
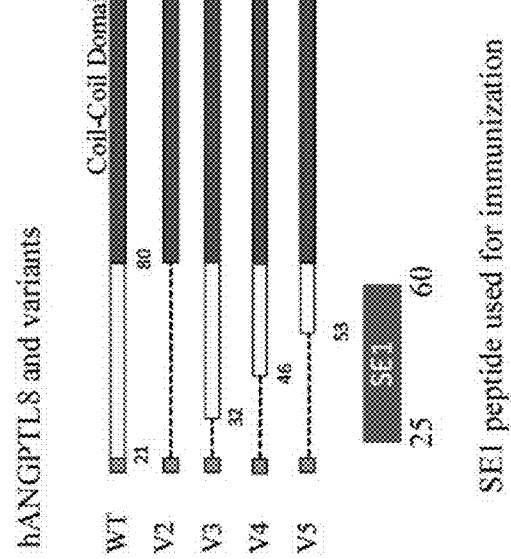

As shown in FIG. 2B, expression of wild-type hANGPTL8 and variant V3 increased plasma triglycerides levels by approximately three-fold. Variant V3 has a deletion of amino acids 22-31 of hANGPTL8 (SEQ ID NO:1). In contrast, expression of variants V2, V4 and V5 did not increase plasma triglyceride levels and appeared to actually reduce triglyceride levels below the control. Variant V2 has a deletion of amino acids 22-80 of hANGPTL8, variant V4 has a deletion of amino acids 22-45 of hANGPTL8, and variant V5 has a deletion of amino acids 22-52 of hANGPTL8. These results suggest that amino acids 32-46 are necessary for human ANGPTL8 to increase triglyceride levels.

Example 2

Generation of Antibodies

Anti-ANGPTL8 antibodies were generated using several different immunogens. Mice were immunized with (i) DNA encoding human ANGPTL8, (ii) a peptide comprising amino acids 25-60 of human ANGPTL8 (hSE1 peptide; SEQ ID NO:6) or (iii) a purified fusion protein comprising human ANGPTL8 (SEQ ID NO:2) linked to human serum albumin (HSA) and a FLAG tag (Flag-HSA-hANGPTL8). Single cell suspensions of lymphocytes were obtained from the spleens and draining lymph nodes of immunized animals after the animals had been determined to have suitable antibody titers. Lymphocytes were fused with SP2/0 myeloma cells by electrofusion. Fused cells were plated into semi-solid media in the presence of HAT selection. After 7-10 days of culture, hybridoma clones were selected and screened as described herein in Example 3.

Example 3

Screening of Antibodies

Hybridoma supernatants from the immunization and fusion campaigns described in Example 2 were screened by ELISA for binding to (i) human ANGPTL8, (ii) human SE1 peptide, (iii) a peptide comprising amino acids 22-46 of hANGPTL8 (SEQ ID NO:1), (iii) a peptide comprising amino acids 61-80 of hANGPTL8, (iv) a peptide comprising amino acids 80-138 of hANGPTL8, and (iv) a peptide comprising amino acids 139-198 of hANGPTL8. Hundreds of antibodies were identified as binders to human ANGPTL8 and/or fragments thereof.

A subpopulation of the antibodies identified by ELISA were tested in vivo for their ability to reduce plasma triglyceride levels in mice expressing hANGPTL8. C57BL/6J mice (6 mice per group) were administered one of the anti-hANGPTL8 antibodies or a control antibody (anti-KLH) by subcutaneous injection (Day-1). Antibodies were given as a single dose of 10 mg/kg. The next day (Day 0), the mice were injected with $1 \times 10^{11}$ IU of rAAV expressing hANGPTL8 (AAV-hANGPTL8) or a control rAAV expressing green fluorescent protein (AAV-GFP). One day after administration of AAVhANGPTL8 or AAV-GFP, blood was drawn from the tail veins of individual mice and triglyceride levels were determined as described herein.

Figure 3:
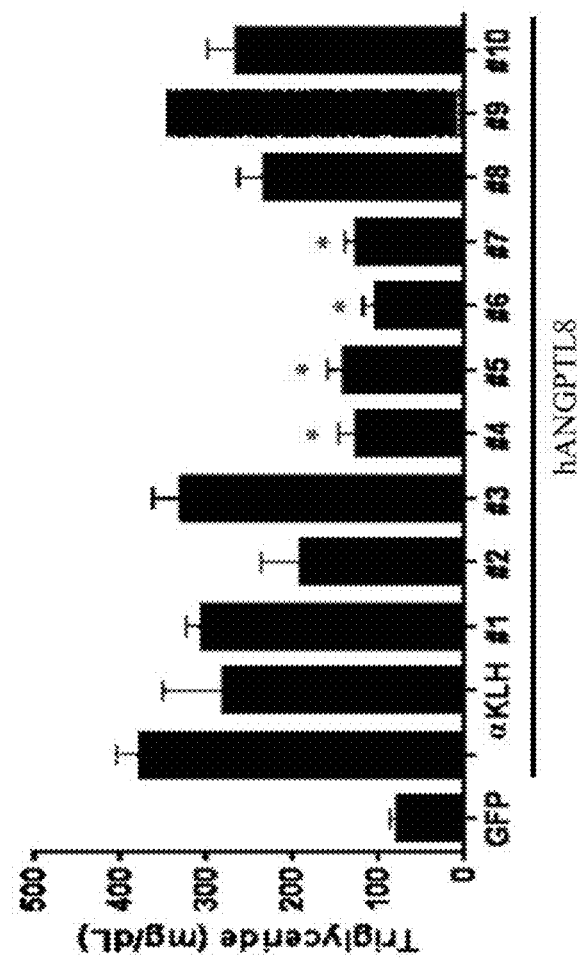
FIG. 3. Plasma triglyceride levels in mice injected with a rAAV expressing human ANGPTL8 and treated with anti-hANGPTL8 antibodies. Control animals were (i) injected with rAAV expressing hANGPTL8 and no antibody treatment; (ii) injected with rAAV expressing hANGPTL8 and treated with a control anti-KLH antibody; or (iii) injected with a rAAV expressing GFP.

As shown in FIG. 3, of the antibodies tested, four different antibodies reduced triglyceride levels or inhibited increased triglyceride levels induced by the expression of hANGPTL8 by approximately three-fold as compared to no antibody treatment. Three of these antibodies, 1E5, 1A8, and 1E9, were determined to bind within the N-terminal region of ANGPTL8 (SE1 peptide; amino acids 25-60).

Example 4

Antibody Binding Affinity

The binding affinities of antibodies 1E5, 1A8, and 1E9 to human ANGPTL8 were measured using a BIACORE system (GE Healthcare LifeSciences). Briefly, anti-mouse Fc antibody (Sigma-Aldrich) was immobilized on all four flow cells of a CM5 chip using amine coupling reagents (GE Healthcare LifeSciences). Antibody from hybridoma supernatants were captured on flow cells 2, 3, and 4 using flow cell 1 as a reference. The SE1 peptide of human ANGPTL8 (hSE1; SEQ ID NO:6), a corresponding SE1 peptide of cynomolgus monkey ANGPTL8 (cSE1; SEQ ID NO:67), or human ANGPTL8 was injected at a flow rate of 50 µL/min at 25° C. Kinetic data were collected over time and fit using the simultaneous global fit equation to yield affinity constants (KD values) for each antibody.

Human ANGPTL8 (SEQ ID NO:2) was produced as a fusion with bacterial NusA protein (NusA-hANGPTL8). An E. coli BL21 transformant containing a NusA-hANGPTL8-expressing construct was induced with 1 mM IPTG at 37° C. for 4 hours. The cells were harvested by centrifugation and the cell pellet was solubilized using BugBusterTM Protein Extraction Reagent (Novagen, Inc). NusA-hANGPTL8 was captured using a chelating Sepharose FF column and eluted using PBS containing 250 mM imidazole. The NusA-hANGPTL8 fusion protein was concentrated by ultrafiltration and further purified by column chromatography.

Assay results are shown in Table 4 and the BIACORE result for 1E5 binding to hANGPTL8 (NusA-hANGPTL8 fusion protein) is shown in FIG. 4.

TABLE 4

| Anti-ANGPTL8 Antibody | hSE1 | cSE1 Kd (nM) | NusA-hANGPTL8 |
|---|---|---|---|
| 1E5 | 0.41 | 0.67 | 0.44 |
| 1A8 | 0.80 | 1.04 | 2.5 |
| 1E9 | 0.92 | 1.80 | 2.1 |

Example 5

Humanized Antibody

The heavy chain and light chain variable region sequences as well as CDR sequences of antibodies 1E5, 1E9, and 1A8 are shown in Tables 1-3. Antibody 1E5 was humanized by methods known by those skilled in the art and is referred to herein as Hz1E5. The heavy chain variable sequence of Hz1E5 is SEQ ID NO:62 and the light chain variable sequences of Hz1E5 is SEQ ID NO:63.

Figure 5A:
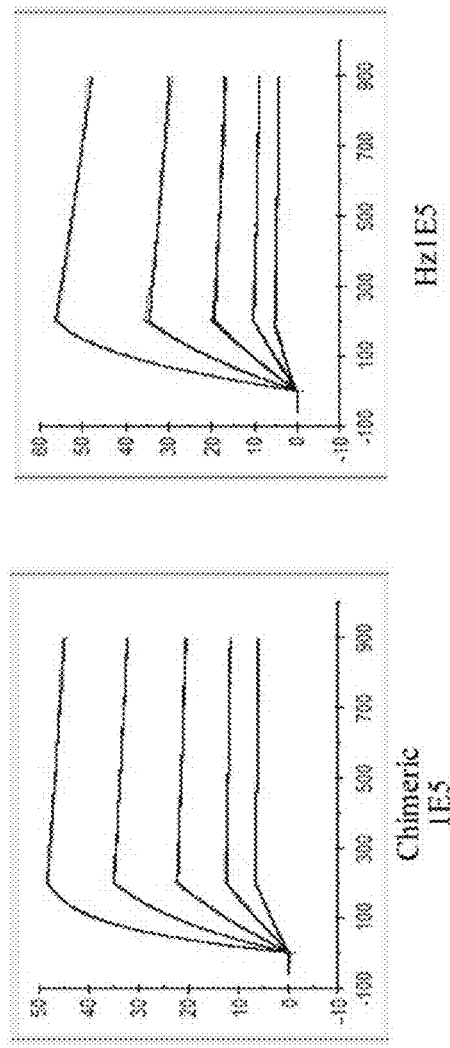
FIG. 5A-5B.

The binding affinity of Hz1E5 was determined using a BIACORE system as described herein and compared with the binding affinity of a chimeric 1E5 antibody containing the murine variable regions of 1E5 and a human Fc region. The humanized antibody Hz1E5 had a binding affinity to human SE1 peptide of 0.9 nM as compared to the chimeric antibody's binding affinity of 0.35 nM (FIG. 5A).

Humanized antibody Hz1E5 was tested in vivo for its ability to reduce plasma triglyceride levels in mice expressing hANGPTL8. C57BL/6J mice (6-8 mice per group) were administered parental antibody from hybridoma 1E5, chimeric antibody 1E5, humanized antibody Hz1E5, or a control antibody (anti-KLH) by subcutaneous injection (Day-1). Antibodies were administered as a single dose at 30 mg/kg. The next day (Day 0), the mice were injected with 1 x $10^{11}$ IU AAV-hANGPTL8 or control AAV-GFP. One day after injection with the AAVs, blood was obtained from the tail veins of individual mice and triglyceride levels were determined.

Figure 5B:
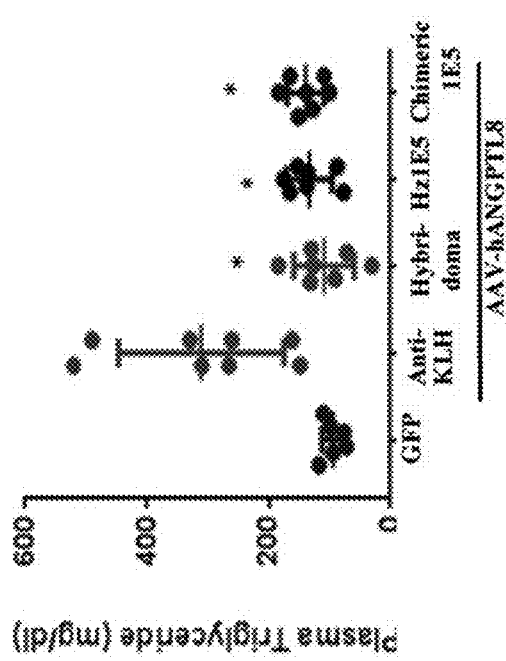

As shown in FIG. 5B, anti-hANGPTL8 antibody Hz1E5 lowered or inhibited the increase of plasma triglycerides induced by expression of hANGPTL8 to a similar extent as the parental antibody. These results suggest that humanization of antibody 1E5 had no effect on the activity of the antibody.

Example 6

Monkey Studies

The ability of anti-ANGPTL8 antibody Hz1E5 to reduce plasma triglyceride levels in vivo was studied in cynomolgus monkeys. Hypertriglyceridemic male cynomolgus monkeys were selected and baseline values of serum triglycerides and serum HDL-cholesterol were measured prior to treatment (Day −3). On Day 0, one group of animals (n=10) received a single dose of anti-hANGPTL8 antibody Hz1E5 (10 mg/kg) by subcutaneous injection. A group of control animals (n=10) received a single dose of vehicle. Blood samples were taken on Days −2, .25 (6 hrs.), 1, 3, 5, 8, 15, 22, and 29 for determination of serum triglycerides and HDL-cholesterol. During the study, all animals were closely monitored for health status.

Figure 6B:
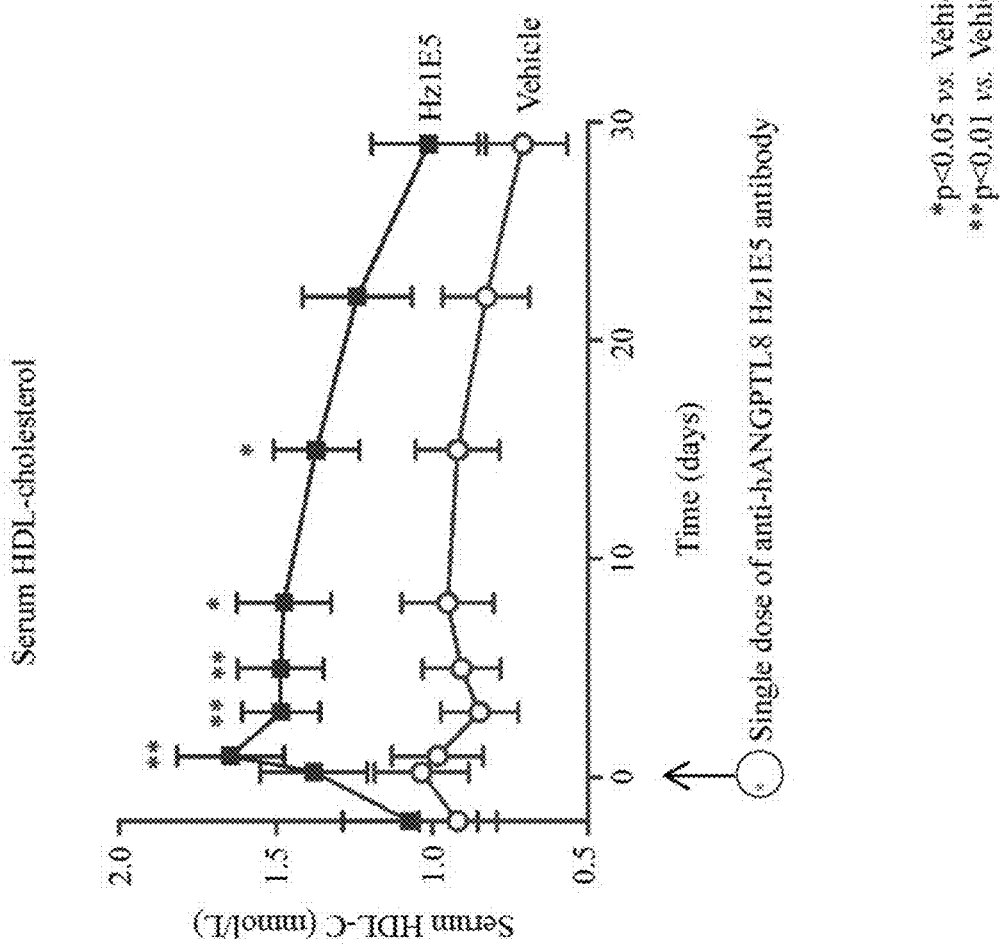

As shown in FIG. 6A, serum triglycerides in hypertriglyceridemic cynomolgus monkeys were significantly reduced as early as 6 hours ($p < 0.05$ vs vehicle) after a single treatment with anti-ANGPTL8 antibody Hz1E5 as compared to animals treated with control vehicle. The triglyceride level in treated animals gradually returned to pre-treatment levels by Day 29, but remained below levels observed in the control animals. In addition, the anti-ANGPTL8 antibody was effective in increasing HDL-cholesterol levels. HDL-cholesterol levels were significantly higher by Day 1 ($p < 0.01$ vs vehicle) in the animals treated with anti-ANGPTL8 antibody as compared to animals treated with control after a single dose of antibody (FIG. 6B). As with triglycerides levels, HDL-cholesterol levels gradually returned to pre-treatment levels by Day 29. These results demonstrated that in a non-human primate model for hypertriglyceridemia an exemplary anti-ANGPTL8 antibody is effective in reducing triglycerides levels and increasing HDL-cholesterol levels.

Although the foregoing present disclosure has been described in some detail by way of illustration and example for purposes of clarity of understanding, the descriptions and examples should not be construed as limiting the scope of the present disclosure. The embodiments of the present disclosure described herein are intended to be merely exemplary, and those skilled in the art will recognize numerous equivalents to the specific procedures described herein. All such equivalents are considered to be within the scope of the present disclosure and are covered by the embodiments.

All publications, patents, patent applications, internet sites, and accession numbers/database sequences including both polynucleotide and polypeptide sequences cited herein are hereby incorporated by reference in their entirety for all purposes to the same extent as if each individual publication, patent, patent application, internet site, or accession number/database sequence were specifically and individually indicated to be so incorporated by reference.

Following are the sequences disclosed in the application with the exception of the heavy chain and light chain CDR sequences defined in Tables 1-3.

```
Human ANGPTL8 amino acid sequence with predicted signal sequence
underlined
                                                       (SEQ ID NO: 1)
MPVPALCLLTNALAMVTRPASAAPMGGPELAQHEELTLLFHGTLQLGQALNGVYRTTEGRL

TKARNSLGLYGRTIELLGQEVSRGRDAAQELRASLLETQMEEDILQLQAEATAEVLGEVA

QAQKVLRDSVQRLEVQLRSATNLGPAYREFEVLKAHADKQSHILTNALIGHVQRQRREMVAQ

QHRLRQIQERLHTAALPA

Human ANGPTL8 amino acid sequence without predicted signal sequence
                                                       (SEQ ID NO: 2)
APMGGPELAQHEELTLLFHGTLQLGQALNGVYRTTEGRLTKARNSLGLYGRTIELLGQEV

SRGRDAAQELRASLLETQMEEDILQLQAEATAEVLGEVAQAQKVLRDSVQRLEVQLRSAW

LGPAYREFEVLKAHADKQSHILTNALTGHVQRQRREMVAQQHRLRQIQERLHTAALPA

Human ANGPTL8 amino acids 22-83
                                                       (SEQ ID NO: 3)
APMGGPELAQHEELTLLFHGTLQLGQALNGVYRTTEGRLTKARNSLGLYGRTIELLGQEV

SR

Human ANGPTL8 amino acids 84-138
                                                       (SEQ ID NO: 4)
GRDAAQELRASLLETQMEEDILQLQAEATAEVLGEVAQAQKVLRDSVQRLEVQLR Human ANGPTL8 amino acids 139-198
                                                       (SEQ ID NO: 5)
SAWLGPAYREFEVLKAHADKQSHILTATALIGHVQRQRREMVAQQHRLRQIQERLHTAALPA Human ANGPTL8 amino acids 25-60 (hSE1 peptide)
                                                       (SEQ ID NO: 6)
GGPELAQHEELTLLFHGTLQLGQALNGVYRTTEGRL Human ANGPTL8 amino acids 22-46 (Sumo peptide)
                                                       (SEQ ID NO: 7)
APMGGPELAQHEELTLLFHGTLQLG Human ANGPTL8 amino acids 32-46
                                                       (SEQ ID NO: 8)
HEELTLLFHGTLQLG Cynomolgus monkey ANGPTL8 amino acid sequence with signal sequence
                                                       (SEQ ID NO: 9)
MLVPALCLLTATALAMVIQPASAAPVGSPELAEHEELTLLFHGTLQLGQALNGVYKTTEGRL

TKARNSLGLYGRTVELLGQEVSRGRDAAQELRASLLETQMEEDILQLKAEAIAEVLEEVA

QAQKVLQDSVRRLEVQLRSAWLGPAYQEFEVLKAHADKQSHILTATALIGHVQRQRREMVAQ

QHRLRQIQERIHKAALPA

Mouse ANGPTL8 amino acid sequence with signal sequence
                                                       (SEQ ID NO: 10)
MAVLALCLLTNTLASAVRPAPVAPLGGPEPAQYEELTLLFHGALQLGQALNGVYRATEARL

TEAGHSLGLYDRALEFLGTEVRQGQDATQELRTSLSEIQVEEDALHLRAEATARSLGEVA

RAQQALRDTVRRLQVQLRGAWLGQAHQEFETLKARADKQSHLLTATALTGHVQRQQREMAEQ

QQWLRQIQQRLHTAALPA

1E5 Heavy chain variable region amino acid sequence
                                                       (SEQ ID NO: 35)
QVQLQQSGAELVKPGTSVRLSCKASGYTFTDYTIHTATVKLRSGQGLEWIGWFYPGSDNIKY

NAKFKDKATLTADKSSSTVYMDLGRLTSEDSAVYFCARHEAFSYYDVAWFAYTNGQGTLVT

VSA

1E5 Light chain variable region amino acid sequence
                                                       (SEQ ID NO: 36)
DVVMTQTPLSLPVSLGDQASISCRSSQSLVHSNGNTYLHTNYLQKPGQSPKLLIYTVSNRF

SGVPDRFSGSGSGSDFTLNFSRVEAEDLGVYFCSQTTHFPYTFGGGTKLEIK
```

-continued

1E9 Heavy chain variable region amino acid sequence
(SEQ ID NO: 44)
QVQLQQSGTELVKPGASVKLSCKASGYTFTDYTIHTAWKQRSGQGLEWIGWFYPGSDNIKF

NAKFRDKATLTADKSSSTVYMELSRLTSEDSAVYFCARHEAFYVYDVAWFANWGQGTLVT

VST

1E9 Light chain variable region amino acid sequence
(SEQ ID NO: 45)
DVVMTQTPLSLPVSLGDQASISCRSSQSLVHSNGNTYLHWFLQKPGQSPNLLIYTVSNRF

SGVPDRFSGSGSGTDFTLKISRVEAGDLGVYFCSQSTHFPYT FGGGTKLEIK

1A8 Heavy chain variable region amino acid sequence
(SEQ ID NO: 56)
QVQLQQSGAELVKPGASVKLSCKASGYTFTDYTIHWVKQRSGQGLEWIGWFYPGSDNIKY

NE KFKDKATLTADKSSSIVYMELSRLTSEDSAVYFCARHEAYYVYDVAWFAYWGQGTLVT

VSA

1A8 Light chain variable region amino acid sequence
(SEQ ID NO: 57)
DVVMTQTPLSLPVSLGDQASISCSSSQSLVHSNGNTFLHWFLQRPGQSPKLLIYTVSNRF

SGVPDRFSGSGSGTDFTLKISRVEAEDLGVYFCSQSTHFPYTEGGGTTLEIK

Heavy Chain CDR2 consensus sequence
(SEQ ID NO: 58)
WFYPGSDNIKX$_1$NX$_2$KFX$_3$D
X$_1$ = Y or F; X$_2$ = A or E; X$_3$ = K or R Heavy chain CDR3 consensus sequence
(SEQ ID NO: 59)
HEAX$_1$X$_2$X$_3$YDVAWFAX$_4$
X$_1$ = F or Y; X$_2$ = S or Y; X$_3$ = Y or V; X$_4$ = Y or N Light chain CDR1 consensus sequence
(SEQ ID NO: 60)
X$_1$SSQSLVHSNGNTX$_2$LH
X$_1$ = R or S  X$_2$ = Y or F Light chain CDR3 consensus sequence
(SEQ ID NO: 61)
SQX$_1$THFPYT
X$_1$ = T or S Hz1E5.A1 Heavy chain variable region amino acid sequence
(SEQ ID NO: 62)
EVQLVQSGAEVKKPGSSVKVSCKASGYTFTDYTIHWVRQAPGQGLEWMGWFYPGSDNIKY

NAKFKDRATLTADKSTTAYMELSSLRSEDTAVYYCARHEAFSYYDVAWFAYWGQGTLVT

VSS

Hz1E5.A1 Light chain variable region amino acid sequence
(SEQ ID NO: 63)
DVVMTQTPLSLPVTPGEPASISCRSSQSLVHSNGNTYLHWYLQKPGQSPQLLIYTVSNRF

SGVPDRFSGSGSGSDFTLKISRVEAEDVGVYFCSQTTHFPYTFGQGTKVEIK

Hz1E5.A1 Heavy chain amino acid sequence without signal sequence
(SEQ ID NO: 64)
EVQLVQSGAEVKKPGSSVKVSCKASGYTFTDYTIHWVRQAPGQGLEWMGWFYPGSDNIKY

NAKFKDRATLTADKSTSTAYMELSSLRSEDTAVYYCARHEAFSYYDVAWFAYWGQGTLVT

VSSASTKGPSVFPLAPSSKSTSGGTAALGCLVKDYFPEPVTVSWNSGALTSGVHTFPAVL

QSSGLYSLSSVVTVPSSSLGTQTYICNVNHKPSNTKVDKKVEPKSCDKTHTCPPCPAPEL

LGGPSVFLFPPKPKDTLMISRIPEVICVVVDVSHEDPEVKFNWYVDGVEVHNAKTKPREE

QYNSTYRVVSVLTVLHQDWLNGKEYKCKVSNKALPAPIEKTISKAKGQPREPQVYTLPPS

RE EMTKNQVSLTCLVKGFYPSDIAVEWESNGQPENNYKTTPPVLDSDGSFFLYSKLTVDK

SRWQQGNVFSCSVMHEALHNHYTQKSLSLSPGK

Hz1E5.A1 Light chain amino acid sequence without signal sequence
(SEQ ID NO: 65)
DVVMTQTPLSLPVTPGEPASISCRSSQSLVHSNGNTYLHWYLQKPGQSPQLLIYTVSNRF

SGVPDRFSGSGSGSDFTLKISRVEAEDVGVYFCSQTTHFPYTFGQGTKVEIKRTVAAPSV

FIFPPSDEQLKSGTASVVCLLNNFYPREAKVQWKVDNALQSGNSQESVTEQDSKDSTYSL

SSTLTLSKADYEKHKVYACEVTHQGLSSPVTKSFNRGEC

FLAG tag
(SEQ ID NO: 66)
DYKDDDDK

Cyno ANGPLT8 amino acids 25-60 (cSE1 peptide)
(SEQ ID NO: 67)
GSPELAEHEELTLLFHGTLQLGQALNGVYKTTEGRL

---

What is claimed:

1. A method of lowering triglyceride levels in a human subject, the method comprising administering to the human subject a therapeutically effective amount of an antibody or antigen-binding fragment thereof that specifically binds human Angiopoietin-like protein 8 (ANGPTL8), wherein the antibody or antigen-binding fragment thereof comprises:
   a) a heavy chain variable region (VH) comprising a VH complementarity determining region (CDR)1, a VH CDR2, and a VH CDR3 from the amino acid sequence of SEQ ID NO:35, and a light chain variable region (VL) comprising a VL CDR1, a VL CDR2, and a VL CDR3 from the amino acid sequence of SEQ ID NO:36;
   (b) a VH comprising a VH CDR1, a VH CDR2, and a VH CDR3 from the amino acid sequence of SEQ ID NO:62, and a VL comprising a VL CDR1, a VL CDR2, and a VL CDR3 from the amino acid sequence of SEQ ID NO:63,
   (c) a VH comprising a VH CDR1, a VH CDR2, and a VH CDR3 from the amino acid sequence of SEQ ID NO:44, and a VL comprising a VL CDR1, a VL CDR2, and a VL CDR3 from the amino acid sequence of SEQ ID NO:45, or
   (d) a VH comprising a VH CDR1, a VH CDR2, and a VH CDR3 from the amino acid sequence of SEQ ID NO:56, and a VL comprising a VL CDR1, a VL CDR2, and a VL CDR3 from the amino acid sequence of SEQ ID NO:57.

2. The method of claim 1, wherein:
   (a) the VH CDR1 comprises the amino acid sequence of SEQ ID NO:11, the VH CDR2 comprises the amino acid sequence of SEQ ID NO:16, the VH CDR3 comprises the amino acid sequence of SEQ ID NO:21, the VL CDR1 comprises the amino acid sequence of SEQ ID NO:25, the VL comprises the amino acid sequence of SEQ ID NO:29, and the VL CDR3 comprises the amino acid sequence of SEQ ID NO:32;
   (b) the VH CDR1 comprises the amino acid sequence of SEQ ID NO:12, the VH CDR2 comprises the amino acid sequence of SEQ ID NO:17, the VH CDR3 comprises the amino acid sequence of SEQ ID NO:22, the VL CDR1 comprises the amino acid sequence of SEQ ID NO:26, the VL CDR2 comprises the amino acid sequence of SEQ ID NO:30, and the VL CDR3 comprises the amino acid sequence of SEQ ID NO:32;
   (c) the VH CDR1 comprises the amino acid sequence of SEQ ID NO:13, the VH CDR2 comprises the amino acid sequence of SEQ ID NO:16, the VH CDR3 comprises the amino acid sequence of SEQ ID NO:21, the VL CDR1 comprises the amino acid sequence of SEQ ID NO:25, the VL CDR2 comprises the amino acid sequence of SEQ ID NO:29, and the VL CDR3 comprises the amino acid sequence of SEQ ID NO:32;
   (d) the VH CDR1 comprises the amino acid sequence of SEQ ID NO:14, the VH CDR2 comprises the amino acid sequence of SEQ ID NO:18, the VH CDR3 comprises the amino acid sequence of SEQ ID NO:23, the VL CDR1 comprises the amino acid sequence of SEQ ID NO:27, the VL CDR2 comprises the amino acid sequence of SEQ ID NO:30, and the VL CDR3 comprises the amino acid sequence of SEQ ID NO:33;
   (e) the VH CDR1 comprises the amino acid sequence of SEQ ID NO:15, the VH CDR2 comprises the amino acid sequence of SEQ ID NO:19, the VH CDR3 comprises the amino acid sequence of SEQ ID NO:24, the VL CDR1 comprises the amino acid sequence of SEQ ID NO:28, the VL CDR2 comprises the amino acid sequence of SEQ ID NO:31, and the VL CDR3 comprises the amino acid sequence of SEQ ID NO:34; or
   (f) the VH CDR1 comprises the amino acid sequence of SEQ ID NO:11, the VH CDR2 comprises the amino acid sequence of SEQ ID NO:20, the VH CDR3 comprises the amino acid sequence of SEQ ID NO:21, the VL CDR1 comprises the amino acid sequence of SEQ ID NO:25, the VL CDR2 comprises the amino acid sequence of SEQ ID NO:29, and the VL CDR3 comprises the amino acid sequence of SEQ ID NO:32.

3. The method of claim 2, wherein the VH has at least 80% sequence identity to the amino acid sequence of SEQ ID NO:35 and the VL has at least 80% sequence identity to the amino acid sequence of SEQ ID NO:36.

4. The method of claim 2, wherein the VH has at least 80% sequence identity to the amino acid sequence of SEQ ID NO:62, and the VL has at least 80% sequence identity to the amino acid sequence of SEQ ID NO:63.

5. The method of claim 1, wherein the VH CDR1 comprises the amino acid sequence of SEQ ID NO:13, the VH CDR2 comprises the amino acid sequence of SEQ ID NO:16, the VH CDR3 comprises the amino acid sequence of SEQ ID NO:21, the VL CDR1 comprises the amino acid sequence of SEQ ID NO:25, the VL CDR2 comprises the amino acid sequence of SEQ ID NO:29, and the VL CDR3 comprises the amino acid sequence of SEQ ID NO:32.

6. The method of claim 5, wherein the VH comprises the amino acid sequence of SEQ ID NO:62 and the VL comprises the amino acid sequence of SEQ ID NO:63.

7. The method of claim 5, the method comprising administering to the human subject the therapeutically effective amount of the antibody that specifically binds human ANGPTL8, wherein the antibody comprises a heavy chain having at least 90% sequence identity to the amino acid sequence of SEQ ID NO:64 and a light chain having at least 90% sequence identity to the amino acid sequence of SEQ ID NO:65.

8. The method of claim 1, wherein
(a) the VH CDR1 comprises the amino acid sequence of SEQ ID NO:11, the VH CDR2 comprises the amino acid sequence of SEQ ID NO:37, the VH CDR3 comprises the amino acid sequence of SEQ ID NO:38, the VL CDR1 comprises the amino acid sequence of SEQ ID NO:25, the VL CDR2 comprises the amino acid sequence of SEQ ID NO:29, and the VL CDR3 comprises the amino acid sequence of SEQ ID NO:41;
(b) the VH CDR1 comprises the amino acid sequence of SEQ ID NO:12, the VH CDR2 comprises the amino acid sequence of SEQ ID NO:17, the VH CDR3 comprises the amino acid sequence of SEQ ID NO:39, the VL CDR1 comprises the amino acid sequence of SEQ ID NO:26, the VL CDR2 comprises the amino acid sequence of SEQ ID NO:30, and the VL CDR3 comprises the amino acid sequence of SEQ ID NO:41;
(c) the VH CDR1 comprises the amino acid sequence of SEQ ID NO:13, the VH CDR2 comprises the amino acid sequence of SEQ ID NO:37, the VH CDR3 comprises the amino acid sequence of SEQ ID NO:38, the VL CDR1 comprises the amino acid sequence of SEQ ID NO:25, the VL CDR2 comprises the amino acid sequence of SEQ ID NO:29, and the VL CDR3 comprises the amino acid sequence of SEQ ID NO:41;
(d) the VH CDR1 comprises the amino acid sequence of SEQ ID NO:14, the VH CDR2 comprises the amino acid sequence of SEQ ID NO:18, the VH CDR3 comprises the amino acid sequence of SEQ ID NO:68, the VL CDR1 comprises the amino acid sequence of SEQ ID NO:27, the VL CDR2 comprises the amino acid sequence of SEQ ID NO:30, and the VL CDR3 comprises the amino acid sequence of SEQ ID NO:42;
(e) the VH CDR1 comprises the amino acid sequence of SEQ ID NO:15, the VH CDR2 comprises the amino acid sequence of SEQ ID NO:19, the VH CDR3 comprises the amino acid sequence of SEQ ID NO:69, the VL CDR1 comprises the amino acid sequence of SEQ ID NO:40, the VL CDR2 comprises the amino acid sequence of SEQ ID NO:31, and the VL CDR3 comprises the amino acid sequence of SEQ ID NO:43; or
(f) the VH CDR1 comprises the amino acid sequence of SEQ ID NO:11, the VH CDR2 comprises the amino acid sequence of SEQ ID NO:20, the VH CDR3 comprises the amino acid sequence of SEQ ID NO:38, the VL CDR1 comprises the amino acid sequence of SEQ ID NO:25, the VL CDR2 comprises the amino acid sequence of SEQ ID NO:29, and the VL CDR3 comprises the amino acid sequence of SEQ ID NO:41.

9. The method of claim 8, wherein the VH has at least 80% sequence identity to the amino acid sequence of SEQ ID NO:44 and the VL has at least 80% sequence identity to the amino acid sequence of SEQ ID NO:45.

10. The method of claim 1, wherein:
(a) the VH CDR1 comprises the amino acid sequence of SEQ ID NO:11, the VH CDR2 comprises the amino acid sequence of SEQ ID NO:46, the VH CDR3 comprises the amino acid sequence of SEQ ID NO:48, the VL CDR1 comprises the amino acid sequence of SEQ ID NO:52, the VL CDR2 comprises the amino acid sequence of SEQ ID NO:29, and the VL CDR3 comprises the amino acid sequence of SEQ ID NO:41;
(b) the VH CDR1 comprises the amino acid sequence of SEQ ID NO:12, the VH CDR2 comprises the amino acid sequence of SEQ ID NO:17, the VH CDR3 comprises the amino acid sequence of SEQ ID NO:49, the VL CDR1 comprises the amino acid sequence of SEQ ID NO:53, the VL CDR2 comprises the amino acid sequence of SEQ ID NO:30, and the VL CDR3 comprises the amino acid sequence of SEQ ID NO:41;
(c) the VH CDR1 comprises the amino acid sequence of SEQ ID NO:13, the VH CDR2 comprises the amino acid sequence of SEQ ID NO:46, the VH CDR3 comprises the amino acid sequence of SEQ ID NO:48, the VL CDR1 comprises the amino acid sequence of SEQ ID NO:52, the VL CDR2 comprises the amino acid sequence of SEQ ID NO:29, and the VL CDR3 comprises the amino acid sequence of SEQ ID NO:41;
(d) the VH CDR1 comprises the amino acid sequence of SEQ ID NO:14, the VH CDR2 comprises the amino acid sequence of SEQ ID NO:18, the VH CDR3 comprises the amino acid sequence of SEQ ID NO:50, the VL CDR1 comprises the amino acid sequence of SEQ ID NO:54, the VL CDR2 comprises the amino acid sequence of SEQ ID NO:30, and the VL CDR3 comprises the amino acid sequence of SEQ ID NO:42;
(e) the VH CDR1 comprises the amino acid sequence of SEQ ID NO:15, the VH CDR2 comprises the amino acid sequence of SEQ ID NO:47, the VH CDR3 comprises the amino acid sequence of SEQ ID NO:51, the VL CDR1 comprises the amino acid sequence of SEQ ID NO:55, the VL CDR2 comprises the amino acid sequence of SEQ ID NO:31, and the VL CDR3 comprises the amino acid sequence of SEQ ID NO:43; or
(f) the VH CDR1 comprises the amino acid sequence of SEQ ID NO:11, the VH CDR2 comprises the amino acid sequence of SEQ ID NO:20, the VH CDR3 comprises the amino acid sequence of SEQ ID NO:48, the VL CDR1 comprises the amino acid sequence of SEQ ID NO:52, the VL CDR2 comprises the amino acid sequence of SEQ ID NO:29, and the VL CDR3 comprises the amino acid sequence of SEQ ID NO:41.

11. The method of claim 10, wherein the VH has at least 80% sequence identity to the amino acid sequence of SEQ ID NO:56 and the VL has at least 80% sequence identity to the amino acid sequence of SEQ ID NO:57.

12. The method of claim 1, wherein:
(a) the VH has at least 80% sequence identity to the amino acid sequence of SEQ ID NO:35, and the VL has at least 80% sequence identity to the amino acid sequence of SEQ ID NO:36;
(b) the VH has at least 80% sequence identity to the amino acid sequence of SEQ ID NO:62, and the VL has at least 80% sequence identity to the amino acid sequence of SEQ ID NO:63;

(c) the VH has at least 80% sequence identity to the amino acid sequence of SEQ ID NO:44, and the VL has at least 80% sequence identity to the amino acid sequence of SEQ ID NO:45; or (d) the VH has at least 80% sequence identity to the amino acid sequence of SEQ ID NO:56, and the VL has at least 80% sequence identity to the amino acid sequence of SEQ ID NO:57.

13. The method of claim 1, wherein the antibody is a humanized or chimeric antibody.

14. The method of claim 1, wherein the antibody or antigen-binding fragment thereof is a Fab, Fab', F(ab')2, Fv, scFv, (scFv)2, single chain antibody, dual variable region antibody, linear antibody, a bispecific antibody, or a multi-specific antibody.

15. The method of claim 1, wherein the antibody or antigen-binding fragment thereof:
is an antagonist of ANGPTL8;
(ii) inhibits ANGPTL8 activity;
(iii) lowers triglyceride levels;
(iv) lowers LDL-cholesterol levels; and/or
(v) increases HDL-cholesterol levels.

16. A method of lowering triglyceride levels in a human subject, the method comprising administering to the human subject a therapeutically effective amount of an antibody that specifically binds ANGPTL8, wherein the antibody comprises a heavy chain having the amino acid sequence of SEQ ID NO:64 and a light chain having the amino acid sequence of SEQ ID NO:65.

17. A method of modulating cholesterol levels in a human subject, the method comprising administering to the human subject a therapeutically effective amount of an antibody or antigen-binding fragment thereof that specifically binds human ANGPTL8, wherein the antibody or antigen-binding fragment thereof comprises:
a) a heavy chain variable region VH comprising a VH CDR1, a VH CDR2, and a VH CDR3 from the amino acid sequence of SEQ ID NO:35, and a VL comprising a VL CDR1, a VL CDR2, and a VL CDR3 from the amino acid sequence of SEQ ID NO:36;
(b) a VH comprising a VH CDR1, a VH CDR2, and a VH CDR3 from the amino acid sequence of SEQ ID NO:62, and a VL comprising a VL CDR1, a VL CDR2, and a VL CDR3 from the amino acid sequence of SEQ ID NO:63;
(c) a VH comprising a VH CDR1, a VH CDR2, and a VH CDR3 from the amino acid sequence of SEQ ID NO:44, and a VL comprising a VL CDR1, a VL CDR2, and a VL CDR3 from the amino acid sequence of SEQ ID NO:45; or
(d) a VH comprising a VH CDR1, a VH CDR2, and a VH CDR3 from the amino acid sequence of SEQ ID NO:56, and a VL comprising a VL CDR1, a VL CDR2, and a VL CDR3 from the amino acid sequence of SEQ ID NO:57;
wherein the modulating is increasing HDL-cholesterol levels or decreasing LDL-cholesterol levels.

18. The method of claim 17, wherein:
(a) the VH CDR1 comprises the amino acid sequence of SEQ ID NO:11, the VH CDR2 comprises the amino acid sequence of SEQ ID NO:16, the VH CDR3 comprises the amino acid sequence of SEQ ID NO:21, the VL CDR1 comprises the amino acid sequence of SEQ ID NO:25, the VL comprises the amino acid sequence of SEQ ID NO:29, and the VL CDR3 comprises the amino acid sequence of SEQ ID NO:32;

(b) the VH CDR1 comprises the amino acid sequence of SEQ ID NO:12, the VH CDR2 comprises the amino acid sequence of SEQ ID NO:17, the VH CDR3 comprises the amino acid sequence of SEQ ID NO:22, the VL CDR1 comprises the amino acid sequence of SEQ ID NO:26, the VL CDR2 comprises the amino acid sequence of SEQ ID NO:30, and the VL CDR3 comprises the amino acid sequence of SEQ ID NO:32;

(c) the VH CDR1 comprises the amino acid sequence of SEQ ID NO:13, the VH CDR2 comprises the amino acid sequence of SEQ ID NO:16, the VH CDR3 comprises the amino acid sequence of SEQ ID NO:21, the VL CDR1 comprises the amino acid sequence of SEQ ID NO:25, the VL CDR2 comprises the amino acid sequence of SEQ ID NO:29, and the VL CDR3 comprises the amino acid sequence of SEQ ID NO:32;

(d) the VH CDR1 comprises the amino acid sequence of SEQ ID NO:14, the VH CDR2 comprises the amino acid sequence of SEQ ID NO:18, the VH CDR3 comprises the amino acid sequence of SEQ ID NO:23, the VL CDR1 comprises the amino acid sequence of SEQ ID NO:27, the VL CDR2 comprises the amino acid sequence of SEQ ID NO:30, and the VL CDR3 comprises the amino acid sequence of SEQ ID NO:33;

(e) the VH CDR1 comprises the amino acid sequence of SEQ ID NO:15, the VH CDR2 comprises the amino acid sequence of SEQ ID NO:19, the VH CDR3 comprises the amino acid sequence of SEQ ID NO:24, the VL CDR1 comprises the amino acid sequence of SEQ ID NO:28, the VL CDR2 comprises the amino acid sequence of SEQ ID NO:31, and the VL CDR3 comprises the amino acid sequence of SEQ ID NO:34; or (f) the VH CDR1 comprises the amino acid sequence of SEQ ID NO:11, the VH CDR2 comprises the amino acid sequence of SEQ ID NO:20, the VH CDR3 comprises the amino acid sequence of SEQ ID NO:21, the VL CDR1 comprises the amino acid sequence of SEQ ID NO:25, the VL CDR2 comprises the amino acid sequence of SEQ ID NO:29, and the VL CDR3 comprises the amino acid sequence of SEQ ID NO:32.

19. The method of claim 17, wherein the VH CDR1 comprises the amino acid sequence of SEQ ID NO:13, the VH CDR2 comprises the amino acid sequence of SEQ ID NO:16, the VH CDR3 comprises the amino acid sequence of SEQ ID NO:21, the VL CDR1 comprises the amino acid sequence of SEQ ID NO:25, the VL CDR2 comprises the amino acid sequence of SEQ ID NO:29, and the VL CDR3 comprises the amino acid sequence of SEQ ID NO:32.

20. The method of claim 19, wherein the VH comprises the amino acid sequence of SEQ ID NO:62 and the VL comprises the amino acid sequence of SEQ ID NO:63.

21. The method of claim 19, wherein the antibody comprises a heavy chain having at least 90% sequence identity to the amino acid sequence of SEQ ID NO:64 and a light chain having at least 90% sequence identity to the amino acid sequence of SEQ ID NO:65.

22. The method of claim 17, wherein
(a) the VH CDR1 comprises the amino acid sequence of SEQ ID NO:11, the VH CDR2 comprises the amino acid sequence of SEQ ID NO:37, the VH CDR3 comprises the amino acid sequence of SEQ ID NO:38, the VL CDR1 comprises the amino acid sequence of SEQ ID NO:25, the VL CDR2 comprises the amino acid sequence of SEQ ID NO:29, and the VL CDR3 comprises the amino acid sequence of SEQ ID NO:41;

(b) the VH CDR1 comprises the amino acid sequence of SEQ ID NO:12, the VH CDR2 comprises the amino acid sequence of SEQ ID NO:17, the VH CDR3 comprises the amino acid sequence of SEQ ID NO:39, the VL CDR1 comprises the amino acid sequence of SEQ ID NO:26, the VL CDR2 comprises the amino acid sequence of SEQ ID NO:30, and the VL CDR3 comprises the amino acid sequence of SEQ ID NO:41;

(c) the VH CDR1 comprises the amino acid sequence of SEQ ID NO:13, the VH CDR2 comprises the amino acid sequence of SEQ ID NO:37, the VH CDR3 comprises the amino acid sequence of SEQ ID NO:38, the VL CDR1 comprises the amino acid sequence of SEQ ID NO:25, the VL CDR2 comprises the amino acid sequence of SEQ ID NO:29, and the VL CDR3 comprises the amino acid sequence of SEQ ID NO:41;

(d) the VH CDR1 comprises the amino acid sequence of SEQ ID NO:14, the VH CDR2 comprises the amino acid sequence of SEQ ID NO:18, the VH CDR3 comprises the amino acid sequence of SEQ ID NO:68, the VL CDR1 comprises the amino acid sequence of SEQ ID NO:27, the VL CDR2 comprises the amino acid sequence of SEQ ID NO:30, and the VL CDR3 comprises the amino acid sequence of SEQ ID NO:42;

(e) the VH CDR1 comprises the amino acid sequence of SEQ ID NO:15, the VH CDR2 comprises the amino acid sequence of SEQ ID NO:19, the VH CDR3 comprises the amino acid sequence of SEQ ID NO:69, the VL CDR1 comprises the amino acid sequence of SEQ ID NO:40, the VL CDR2 comprises the amino acid sequence of SEQ ID NO:31, and the VL CDR3 comprises the amino acid sequence of SEQ ID NO:43; or (f) the VH CDR1 comprises the amino acid sequence of SEQ ID NO:11, the VH CDR2 comprises the amino acid sequence of SEQ ID NO:20, the VH CDR3 comprises the amino acid sequence of SEQ ID NO:38, the VL CDR1 comprises the amino acid sequence of SEQ ID NO:25, the VL CDR2 comprises the amino acid sequence of SEQ ID NO:29, and the VL CDR3 comprises the amino acid sequence of SEQ ID NO:41.

23. The method of claim 17, wherein:

(a) the VH CDR1 comprises the amino acid sequence of SEQ ID NO:11, the VH CDR2 comprises the amino acid sequence of SEQ ID NO:46, the VH CDR3 comprises the amino acid sequence of SEQ ID NO:48, the VL CDR1 comprises the amino acid sequence of SEQ ID NO:52, the VL CDR2 comprises the amino acid sequence of SEQ ID NO:29, and the VL CDR3 comprises the amino acid sequence of SEQ ID NO:41;

(b) the VH CDR1 comprises the amino acid sequence of SEQ ID NO:12, the VH CDR2 comprises the amino acid sequence of SEQ ID NO:17, the VH CDR3 comprises the amino acid sequence of SEQ ID NO:49, the VL CDR1 comprises the amino acid sequence of SEQ ID NO:53, the VL CDR2 comprises the amino acid sequence of SEQ ID NO:30, and the VL CDR3 comprises the amino acid sequence of SEQ ID NO:41;

(c) the VH CDR1 comprises the amino acid sequence of SEQ ID NO:13, the VH CDR2 comprises the amino acid sequence of SEQ ID NO:46, the VH CDR3 comprises the amino acid sequence of SEQ ID NO:48, the VL CDR1 comprises the amino acid sequence of SEQ ID NO:52, the VL CDR2 comprises the amino acid sequence of SEQ ID NO:29, and the VL CDR3 comprises the amino acid sequence of SEQ ID NO:41;

(d) the VH CDR1 comprises the amino acid sequence of SEQ ID NO:14, the VH CDR2 comprises the amino acid sequence of SEQ ID NO:18, the VH CDR3 comprises the amino acid sequence of SEQ ID NO:50, the VL CDR1 comprises the amino acid sequence of SEQ ID NO:54, the VL CDR2 comprises the amino acid sequence of SEQ ID NO:30, and the VL CDR3 comprises the amino acid sequence of SEQ ID NO:42;

(e) the VH CDR1 comprises the amino acid sequence of SEQ ID NO:15, the VH CDR2 comprises the amino acid sequence of SEQ ID NO:47, the VH CDR3 comprises the amino acid sequence of SEQ ID NO:51, the VL CDR1 comprises the amino acid sequence of SEQ ID NO:55, the VL CDR2 comprises the amino acid sequence of SEQ ID NO:31, and the VL CDR3 comprises the amino acid sequence of SEQ ID NO:43; or (f) the VH CDR1 comprises the amino acid sequence of SEQ ID NO:11, the VH CDR2 comprises the amino acid sequence of SEQ ID NO:20, the VH CDR3 comprises the amino acid sequence of SEQ ID NO:48, the VL CDR1 comprises the amino acid sequence of SEQ ID NO:52, the VL CDR2 comprises the amino acid sequence of SEQ ID NO:29, and the VL CDR3 comprises the amino acid sequence of SEQ ID NO:41.

24. The method of claim 17, wherein:

(a) the VH has at least 80% sequence identity to the amino acid sequence of SEQ ID NO:35, and the VL has at least 80% sequence identity to the amino acid sequence of SEQ ID NO:36;

(b) the VH has at least 80% sequence identity to the amino acid sequence of SEQ ID NO:62, and the VL has at least 80% sequence identity to the amino acid sequence of SEQ ID NO:63;

(c) the VH has at least 80% sequence identity to the amino acid sequence of SEQ ID NO:44, and the VL has at least 80% sequence identity to the amino acid sequence of SEQ ID NO:45; or (d) the VH has at least 80% sequence identity to the amino acid sequence of SEQ ID NO:56, and the VL has at least 80% sequence identity to the amino acid sequence of SEQ ID NO:57.

25. The method of claim 17, wherein the modulating is increasing HDL-cholesterol levels.

26. A method of modulating cholesterol levels in a human subject, the method comprising administering to the human subject a therapeutically effective amount of an antibody that specifically binds ANGPTL8, wherein the antibody comprises a heavy chain having the amino acid sequence of SEQ ID NO:64 and a light chain having the amino acid sequence of SEQ ID NO:65, and wherein the modulating is increasing HDL-cholesterol levels or decreasing LDL-cholesterol levels.

27. The method of claim 26, wherein the modulating is increasing HDL-cholesterol levels.

28. A method of treating a disease or disorder associated with elevated triglyceride levels in a human subject, the method comprising administering to the human subject a therapeutically effective amount of an antibody or antigen-binding fragment thereof that specifically binds human ANGPTL8, wherein the antibody or antigen-binding fragment thereof comprises:

a) a VH comprising a VH CDR1, a VH CDR2, and a VH CDR3 from the amino acid sequence of SEQ ID NO:35, and a VL comprising a VL CDR1, a VL CDR2, and a VL CDR3 from the amino acid sequence of SEQ ID NO:36;

(b) a VH comprising a VH CDR1, a VH CDR2, and a VH CDR3 from the amino acid sequence of SEQ ID NO:62, and a VL comprising a VL CDR1, a VL CDR2, and a VL CDR3 from the amino acid sequence of SEQ ID NO:63;

(c) a VH comprising a VH CDR1, a VH CDR2, and a VH CDR3 from the amino acid sequence of SEQ ID NO:44, and a VL comprising a VL CDR1, a VL CDR2, and a VL CDR3 from the amino acid sequence of SEQ ID NO:45, or (d) a VH comprising a VH CDR1, a VH CDR2, and a VH CDR3 from the amino acid sequence of SEQ ID NO:56, and a VL comprising a VL CDR1, a VL CDR2, and a VL CDR3 from the amino acid sequence of SEQ ID NO:57.

29. The method of claim 28, wherein the disease or disorder is hypertriglyceridemia, metabolic syndrome, atherosclerosis, obesity, diabetes, hypothyroidism, acute pancreatitis, liver disease, or kidney disease.

30. The method of claim 28, wherein:

(a) the VH CDR1 comprises the amino acid sequence of SEQ ID NO:11, the VH CDR2 comprises the amino acid sequence of SEQ ID NO:16, the VH CDR3 comprises the amino acid sequence of SEQ ID NO:21, the VL CDR1 comprises the amino acid sequence of SEQ ID NO:25, the VL comprises the amino acid sequence of SEQ ID NO:29, and the VL CDR3 comprises the amino acid sequence of SEQ ID NO:32;

(b) the VH CDR1 comprises the amino acid sequence of SEQ ID NO:12, the VH CDR2 comprises the amino acid sequence of SEQ ID NO:17, the VH CDR3 comprises the amino acid sequence of SEQ ID NO:22, the VL CDR1 comprises the amino acid sequence of SEQ ID NO:26, the VL CDR2 comprises the amino acid sequence of SEQ ID NO:30, and the VL CDR3 comprises the amino acid sequence of SEQ ID NO:32;

(c) the VH CDR1 comprises the amino acid sequence of SEQ ID NO:13, the VH CDR2 comprises the amino acid sequence of SEQ ID NO:16, the VH CDR3 comprises the amino acid sequence of SEQ ID NO:21, the VL CDR1 comprises the amino acid sequence of SEQ ID NO:25, the VL CDR2 comprises the amino acid sequence of SEQ ID NO:29, and the VL CDR3 comprises the amino acid sequence of SEQ ID NO:32;

(d) the VH CDR1 comprises the amino acid sequence of SEQ ID NO:14, the VH CDR2 comprises the amino acid sequence of SEQ ID NO:18, the VH CDR3 comprises the amino acid sequence of SEQ ID NO:23, the VL CDR1 comprises the amino acid sequence of SEQ ID NO:27, the VL CDR2 comprises the amino acid sequence of SEQ ID NO:30, and the VL CDR3 comprises the amino acid sequence of SEQ ID NO:33;

(e) the VH CDR1 comprises the amino acid sequence of SEQ ID NO:15, the VH CDR2 comprises the amino acid sequence of SEQ ID NO:19, the VH CDR3 comprises the amino acid sequence of SEQ ID NO:24, the VL CDR1 comprises the amino acid sequence of SEQ ID NO:28, the VL CDR2 comprises the amino acid sequence of SEQ ID NO:31, and the VL CDR3 comprises the amino acid sequence of SEQ ID NO:34; or (f) the VH CDR1 comprises the amino acid sequence of SEQ ID NO:11, the VH CDR2 comprises the amino acid sequence of SEQ ID NO:20, the VH CDR3 comprises the amino acid sequence of SEQ ID NO:21, the VL CDR1 comprises the amino acid sequence of SEQ ID NO:25, the VL CDR2 comprises the amino acid sequence of SEQ ID NO:29, and the VL CDR3 comprises the amino acid sequence of SEQ ID NO:32.

31. The method of claim 28, wherein the VH CDR1 comprises the amino acid sequence of SEQ ID NO:13, the VH CDR2 comprises the amino acid sequence of SEQ ID NO:16, the VH CDR3 comprises the amino acid sequence of SEQ ID NO:21, the VL CDR1 comprises the amino acid sequence of SEQ ID NO:25, the VL CDR2 comprises the amino acid sequence of SEQ ID NO:29, and the VL CDR3 comprises the amino acid sequence of SEQ ID NO:32.

32. The method of claim 31, wherein the VH comprises the amino acid sequence of SEQ ID NO:62 and the VL comprises the amino acid sequence of SEQ ID NO:63.

33. The method of claim 31, wherein the antibody comprises a heavy chain having at least 90% sequence identity to the amino acid sequence of SEQ ID NO:64 and a light chain having at least 90% sequence identity to the amino acid sequence of SEQ ID NO:65.

34. The method of claim 28, wherein (a) the VH CDR1 comprises the amino acid sequence of SEQ ID NO:11, the VH CDR2 comprises the amino acid sequence of SEQ ID NO:37, the VH CDR3 comprises the amino acid sequence of SEQ ID NO:38, the VL CDR1 comprises the amino acid sequence of SEQ ID NO:25, the VL CDR2 comprises the amino acid sequence of SEQ ID NO:29, and the VL CDR3 comprises the amino acid sequence of SEQ ID NO:41;

(b) the VH CDR1 comprises the amino acid sequence of SEQ ID NO:12, the VH CDR2 comprises the amino acid sequence of SEQ ID NO:17, the VH CDR3 comprises the amino acid sequence of SEQ ID NO:39, the VL CDR1 comprises the amino acid sequence of SEQ ID NO:26, the VL CDR2 comprises the amino acid sequence of SEQ ID NO:30, and the VL CDR3 comprises the amino acid sequence of SEQ ID NO:41;

(c) the VH CDR1 comprises the amino acid sequence of SEQ ID NO:13, the VH CDR2 comprises the amino acid sequence of SEQ ID NO:37, the VH CDR3 comprises the amino acid sequence of SEQ ID NO:38, the VL CDR1 comprises the amino acid sequence of SEQ ID NO:25, the VL CDR2 comprises the amino acid sequence of SEQ ID NO:29, and the VL CDR3 comprises the amino acid sequence of SEQ ID NO:41;

(d) the VH CDR1 comprises the amino acid sequence of SEQ ID NO:14, the VH CDR2 comprises the amino acid sequence of SEQ ID NO:18, the VH CDR3 comprises the amino acid sequence of SEQ ID NO:68, the VL CDR1 comprises the amino acid sequence of SEQ ID NO:27, the VL CDR2 comprises the amino acid sequence of SEQ ID NO:30, and the VL CDR3 comprises the amino acid sequence of SEQ ID NO:42;

(e) the VH CDR1 comprises the amino acid sequence of SEQ ID NO:15, the VH CDR2 comprises the amino acid sequence of SEQ ID NO:19, the VH CDR3 comprises the amino acid sequence of SEQ ID NO:69, the VL CDR1 comprises the amino acid sequence of SEQ ID NO:40, the VL CDR2 comprises the amino acid sequence of SEQ ID NO:31, and the VL CDR3 comprises the amino acid sequence of SEQ ID NO:43; or (f) the VH CDR1 comprises the amino acid sequence of SEQ ID NO:11, the VH CDR2 comprises the amino acid sequence of SEQ ID NO:20, the VH CDR3 comprises the amino acid sequence of SEQ ID NO:38, the VL CDR1 comprises the amino acid sequence of SEQ ID NO:25, the VL CDR2 comprises the amino acid sequence of SEQ ID NO:29, and the VL CDR3 comprises the amino acid sequence of SEQ ID NO:41.

35. The method of claim 28, wherein:
(a) the VH CDR1 comprises the amino acid sequence of SEQ ID NO:11, the VH CDR2 comprises the amino acid sequence of SEQ ID NO:46, the VH CDR3 comprises the amino acid sequence of SEQ ID NO:48, the VL CDR1 comprises the amino acid sequence of SEQ ID NO:52, the VL CDR2 comprises the amino acid sequence of SEQ ID NO:29, and the VL CDR3 comprises the amino acid sequence of SEQ ID NO:41;
(b) the VH CDR1 comprises the amino acid sequence of SEQ ID NO:12, the VH CDR2 comprises the amino acid sequence of SEQ ID NO:17, the VH CDR3 comprises the amino acid sequence of SEQ ID NO:49, the VL CDR1 comprises the amino acid sequence of SEQ ID NO:53, the VL CDR2 comprises the amino acid sequence of SEQ ID NO:30, and the VL CDR3 comprises the amino acid sequence of SEQ ID NO:41;
(c) the VH CDR1 comprises the amino acid sequence of SEQ ID NO:13, the VH CDR2 comprises the amino acid sequence of SEQ ID NO:46, the VH CDR3 comprises the amino acid sequence of SEQ ID NO:48, the VL CDR1 comprises the amino acid sequence of SEQ ID NO:52, the VL CDR2 comprises the amino acid sequence of SEQ ID NO:29, and the VL CDR3 comprises the amino acid sequence of SEQ ID NO:41;
(d) the VH CDR1 comprises the amino acid sequence of SEQ ID NO:14, the VH CDR2 comprises the amino acid sequence of SEQ ID NO:18, the VH CDR3 comprises the amino acid sequence of SEQ ID NO:50, the VL CDR1 comprises the amino acid sequence of SEQ ID NO:54, the VL CDR2 comprises the amino acid sequence of SEQ ID NO:30, and the VL CDR3 comprises the amino acid sequence of SEQ ID NO:42;
(e) the VH CDR1 comprises the amino acid sequence of SEQ ID NO:15, the VH CDR2 comprises the amino acid sequence of SEQ ID NO:47, the VH CDR3 comprises the amino acid sequence of SEQ ID NO:51, the VL CDR1 comprises the amino acid sequence of SEQ ID NO:55, the VL CDR2 comprises the amino acid sequence of SEQ ID NO:31, and the VL CDR3 comprises the amino acid sequence of SEQ ID NO:43; or
(f) the VH CDR1 comprises the amino acid sequence of SEQ ID NO:11, the VH CDR2 comprises the amino acid sequence of SEQ ID NO:20, the VH CDR3 comprises the amino acid sequence of SEQ ID NO:48, the VL CDR1 comprises the amino acid sequence of SEQ ID NO:52, the VL CDR2 comprises the amino acid sequence of SEQ ID NO:29, and the VL CDR3 comprises the amino acid sequence of SEQ ID NO:41.

36. The method of claim 28, wherein:
(a) the VH has at least 80% sequence identity to the amino acid sequence of SEQ ID NO:35, and the VL has at least 80% sequence identity to the amino acid sequence of SEQ ID NO:36;
(b) the VH has at least 80% sequence identity to the amino acid sequence of SEQ ID NO:62, and the VL has at least 80% sequence identity to the amino acid sequence of SEQ ID NO:63;
(c) the VH has at least 80% sequence identity to the amino acid sequence of SEQ ID NO:44, and the VL has at least 80% sequence identity to the amino acid sequence of SEQ ID NO:45; or
(d) the VH has at least 80% sequence identity to the amino acid sequence of SEQ ID NO:56, and the VL has at least 80% sequence identity to the amino acid sequence of SEQ ID NO:57.

37. A method of treating a disease or disorder associated with elevated triglyceride levels in a human subject, the method comprising administering to the human subject a therapeutically effective amount of an antibody that specifically binds ANGPTL8, wherein the antibody comprises a heavy chain having the amino acid sequence of SEQ ID NO:64 and a light chain having the amino acid sequence of SEQ ID NO:65.

38. The method of claim 37, wherein the disease or disorder is hypertriglyceridemia, metabolic syndrome, atherosclerosis, obesity, diabetes, hypothyroidism, acute pancreatitis, liver disease, or kidney disease.

* * * * *

UNITED STATES PATENT AND TRADEMARK OFFICE
CERTIFICATE OF CORRECTION

PATENT NO. : 11,566,067 B2
APPLICATION NO. : 16/996623
DATED : January 31, 2023
INVENTOR(S) : Chun Chu et al.

Page 1 of 2

It is certified that error appears in the above-identified patent and that said Letters Patent is hereby corrected as shown below:

On the Title Page

Column 2, Right Column, (Other Publications), Line 4:
Delete "XP0554.54807," and insert -- XP055454807, --.

Column 2, Right Column, (Other Publications), Line 5:
Delete "2011]," and insert -- 2018], --.

In the Claims

Column 97, Line 29:
In Claim 1, delete "a)" and insert -- (a) --.

Column 97, Line 41:
In Claim 1, delete "NO:63," and insert -- NO:63; --.

Column 97, Line 46:
In Claim 1, delete "NO:45," and insert -- NO:45; --.

Column, 101, Line 12:
In Claim 14, delete "F(ab')2," and insert -- F(ab')$_2$, --.

Column 101, Line 13:
In Claim 14, delete "(scFv)2," and insert -- (scFv)$_2$, --.

Column 101, Line 19:
In Claim 15, before "is" insert -- (i) --.

Column 101, Line 37:
In Claim 17, delete "a)" and insert -- (a) --.

Signed and Sealed this
Twenty-eighth Day of March, 2023

Katherine Kelly Vidal
*Director of the United States Patent and Trademark Office*

Column 104, Line 63:
In Claim 28, delete "a)" and insert -- (a) --.

Column 105, Line 10:
In Claim 28, delete "NO:45," and insert -- NO:45; --.

SEQUENCE LISTING

<160> NUMBER OF SEQ ID NOS: 69

<210> SEQ ID NO 1
<211> LENGTH: 198
<212> TYPE: PRT
<213> ORGANISM: Homo sapiens
<220> FEATURE:
<223> OTHER INFORMATION: Human ANGPTL8 sequence with predicted signal
      sequence

<400> SEQUENCE: 1

Met Pro Val Pro Ala Leu Cys Leu Leu Trp Ala Leu Ala Met Val Thr
1               5                   10                  15

Arg Pro Ala Ser Ala Ala Pro Met Gly Gly Pro Glu Leu Ala Gln His
                20                  25                  30

Glu Glu Leu Thr Leu Leu Phe His Gly Thr Leu Gln Leu Gly Gln Ala
            35                  40                  45

Leu Asn Gly Val Tyr Arg Thr Thr Glu Gly Arg Leu Thr Lys Ala Arg
        50                  55                  60

Asn Ser Leu Gly Leu Tyr Gly Arg Thr Ile Glu Leu Leu Gly Gln Glu
65                  70                  75                  80

Val Ser Arg Gly Arg Asp Ala Ala Gln Glu Leu Arg Ala Ser Leu Leu
                85                  90                  95

Glu Thr Gln Met Glu Glu Asp Ile Leu Gln Leu Gln Ala Glu Ala Thr
            100                 105                 110

Ala Glu Val Leu Gly Glu Val Ala Gln Ala Gln Lys Val Leu Arg Asp
        115                 120                 125

Ser Val Gln Arg Leu Glu Val Gln Leu Arg Ser Ala Trp Leu Gly Pro
    130                 135                 140

Ala Tyr Arg Glu Phe Glu Val Leu Lys Ala His Ala Asp Lys Gln Ser
145                 150                 155                 160

His Ile Leu Trp Ala Leu Thr Gly His Val Gln Arg Gln Arg Arg Glu
                165                 170                 175

Met Val Ala Gln Gln His Arg Leu Arg Gln Ile Gln Glu Arg Leu His
            180                 185                 190

Thr Ala Ala Leu Pro Ala
        195

<210> SEQ ID NO 2
<211> LENGTH: 177
<212> TYPE: PRT
<213> ORGANISM: Homo sapiens
<220> FEATURE:

-continued

<223> OTHER INFORMATION: Human ANGPTL8 sequence without predicted
      signal sequence

<400> SEQUENCE: 2

Ala Pro Met Gly Gly Pro Glu Leu Ala Gln His Glu Glu Leu Thr Leu
1               5                   10                  15

Leu Phe His Gly Thr Leu Gln Leu Gly Gln Ala Leu Asn Gly Val Tyr
            20                  25                  30

Arg Thr Thr Glu Gly Arg Leu Thr Lys Ala Arg Asn Ser Leu Gly Leu
        35                  40                  45

Tyr Gly Arg Thr Ile Glu Leu Leu Gly Gln Glu Val Ser Arg Gly Arg
    50                  55                  60

Asp Ala Ala Gln Glu Leu Arg Ala Ser Leu Leu Glu Thr Gln Met Glu
65                  70                  75                  80

Glu Asp Ile Leu Gln Leu Gln Ala Glu Ala Thr Ala Glu Val Leu Gly
                85                  90                  95

Glu Val Ala Gln Ala Gln Lys Val Leu Arg Asp Ser Val Gln Arg Leu
            100                 105                 110

Glu Val Gln Leu Arg Ser Ala Trp Leu Gly Pro Ala Tyr Arg Glu Phe
        115                 120                 125

Glu Val Leu Lys Ala His Ala Asp Lys Gln Ser His Ile Leu Trp Ala
    130                 135                 140

Leu Thr Gly His Val Gln Arg Gln Arg Glu Met Val Ala Gln Gln
145                 150                 155                 160

His Arg Leu Arg Gln Ile Gln Glu Arg Leu His Thr Ala Ala Leu Pro
                165                 170                 175

Ala

<210> SEQ ID NO 3
<211> LENGTH: 62
<212> TYPE: PRT
<213> ORGANISM: Homo sapiens
<220> FEATURE:
<223> OTHER INFORMATION: Human ANGPTL8 amino acids 22-83

<400> SEQUENCE: 3

Ala Pro Met Gly Gly Pro Glu Leu Ala Gln His Glu Glu Leu Thr Leu
1               5                   10                  15

Leu Phe His Gly Thr Leu Gln Leu Gly Gln Ala Leu Asn Gly Val Tyr
            20                  25                  30

Arg Thr Thr Glu Gly Arg Leu Thr Lys Ala Arg Asn Ser Leu Gly Leu
        35                  40                  45

Tyr Gly Arg Thr Ile Glu Leu Leu Gly Gln Glu Val Ser Arg
    50                  55                  60

<210> SEQ ID NO 4
<211> LENGTH: 55
<212> TYPE: PRT
<213> ORGANISM: Homo sapiens
<220> FEATURE:
<223> OTHER INFORMATION: Human ANGPTL8 amino acids 84-138

<400> SEQUENCE: 4

Gly Arg Asp Ala Ala Gln Glu Leu Arg Ala Ser Leu Leu Glu Thr Gln
1               5                   10                  15

Met Glu Glu Asp Ile Leu Gln Leu Gln Ala Glu Ala Thr Ala Glu Val
            20                  25                  30

Leu Gly Glu Val Ala Gln Ala Gln Lys Val Leu Arg Asp Ser Val Gln

```
                35                  40                  45

Arg Leu Glu Val Gln Leu Arg
    50                  55

<210> SEQ ID NO 5
<211> LENGTH: 60
<212> TYPE: PRT
<213> ORGANISM: Homo sapiens
<220> FEATURE:
<223> OTHER INFORMATION: Human ANGPTL8 amino acids 139-198

<400> SEQUENCE: 5

Ser Ala Trp Leu Gly Pro Ala Tyr Arg Glu Phe Glu Val Leu Lys Ala
1               5                   10                  15

His Ala Asp Lys Gln Ser His Ile Leu Trp Ala Leu Thr Gly His Val
            20                  25                  30

Gln Arg Gln Arg Arg Glu Met Val Ala Gln Gln His Arg Leu Arg Gln
        35                  40                  45

Ile Gln Glu Arg Leu His Thr Ala Ala Leu Pro Ala
    50                  55                  60

<210> SEQ ID NO 6
<211> LENGTH: 36
<212> TYPE: PRT
<213> ORGANISM: Homo sapiens
<220> FEATURE:
<223> OTHER INFORMATION: Human ANGPTL8 amino acids 25-60 (hSE1 peptide)

<400> SEQUENCE: 6

Gly Gly Pro Glu Leu Ala Gln His Glu Glu Leu Thr Leu Leu Phe His
1               5                   10                  15

Gly Thr Leu Gln Leu Gly Gln Ala Leu Asn Gly Val Tyr Arg Thr Thr
            20                  25                  30

Glu Gly Arg Leu
        35

<210> SEQ ID NO 7
<211> LENGTH: 25
<212> TYPE: PRT
<213> ORGANISM: Homo sapiens
<220> FEATURE:
<223> OTHER INFORMATION: Human ANGPTL8 amino acids 22-46 (Sumo peptide)

<400> SEQUENCE: 7

Ala Pro Met Gly Gly Pro Glu Leu Ala Gln His Glu Glu Leu Thr Leu
1               5                   10                  15

Leu Phe His Gly Thr Leu Gln Leu Gly
            20                  25

<210> SEQ ID NO 8
<211> LENGTH: 15
<212> TYPE: PRT
<213> ORGANISM: Homo sapiens
<220> FEATURE:
<223> OTHER INFORMATION: Human ANGPTL8 amino acids 32-46

<400> SEQUENCE: 8

His Glu Glu Leu Thr Leu Leu Phe His Gly Thr Leu Gln Leu Gly
1               5                   10                  15

<210> SEQ ID NO 9
<211> LENGTH: 198
<212> TYPE: PRT
```

<213> ORGANISM: Cynomolgus monkey
<220> FEATURE:
<223> OTHER INFORMATION: ANGPTL8 with signal sequence

<400> SEQUENCE: 9

Met Leu Val Pro Ala Leu Cys Leu Leu Trp Ala Leu Ala Met Val Ile
1               5                   10                  15

Gln Pro Ala Ser Ala Ala Pro Val Gly Ser Pro Glu Leu Ala Glu His
            20                  25                  30

Glu Glu Leu Thr Leu Leu Phe His Gly Thr Leu Gln Leu Gly Gln Ala
        35                  40                  45

Leu Asn Gly Val Tyr Lys Thr Thr Glu Gly Arg Leu Thr Lys Ala Arg
50                  55                  60

Asn Ser Leu Gly Leu Tyr Gly Arg Thr Val Glu Leu Leu Gly Gln Glu
65                  70                  75                  80

Val Ser Arg Gly Arg Asp Ala Ala Gln Glu Leu Arg Ala Ser Leu Leu
                85                  90                  95

Glu Thr Gln Met Glu Glu Asp Ile Leu Gln Leu Lys Ala Glu Ala Ile
            100                 105                 110

Ala Glu Val Leu Glu Glu Val Ala Gln Ala Gln Lys Val Leu Gln Asp
        115                 120                 125

Ser Val Arg Arg Leu Glu Val Gln Leu Arg Ser Ala Trp Leu Gly Pro
    130                 135                 140

Ala Tyr Gln Glu Phe Glu Val Leu Lys Ala His Ala Asp Lys Gln Ser
145                 150                 155                 160

His Ile Leu Trp Ala Leu Thr Gly His Val Gln Arg Gln Arg Arg Glu
                165                 170                 175

Met Val Ala Gln Gln His Arg Leu Arg Gln Ile Gln Glu Arg Ile His
            180                 185                 190

Lys Ala Ala Leu Pro Ala
        195

<210> SEQ ID NO 10
<211> LENGTH: 198
<212> TYPE: PRT
<213> ORGANISM: Mouse
<220> FEATURE:
<223> OTHER INFORMATION: ANGPTL8 with signal sequence

<400> SEQUENCE: 10

Met Ala Val Leu Ala Leu Cys Leu Leu Trp Thr Leu Ala Ser Ala Val
1               5                   10                  15

Arg Pro Ala Pro Val Ala Pro Leu Gly Gly Pro Glu Pro Ala Gln Tyr
            20                  25                  30

Glu Glu Leu Thr Leu Leu Phe His Gly Ala Leu Gln Leu Gly Gln Ala
        35                  40                  45

Leu Asn Gly Val Tyr Arg Ala Thr Glu Ala Arg Leu Thr Glu Ala Gly
50                  55                  60

His Ser Leu Gly Leu Tyr Asp Arg Ala Leu Glu Phe Leu Gly Thr Glu
65                  70                  75                  80

Val Arg Gln Gly Gln Asp Ala Thr Gln Glu Leu Arg Thr Ser Leu Ser
                85                  90                  95

Glu Ile Gln Val Glu Glu Asp Ala Leu His Leu Arg Ala Glu Ala Thr
            100                 105                 110

Ala Arg Ser Leu Gly Glu Val Ala Arg Ala Gln Gln Ala Leu Arg Asp
        115                 120                 125

-continued

Thr Val Arg Arg Leu Gln Val Gln Leu Arg Gly Ala Trp Leu Gly Gln
    130                 135                 140

Ala His Gln Glu Phe Glu Thr Leu Lys Ala Arg Ala Asp Lys Gln Ser
145                 150                 155                 160

His Leu Leu Trp Ala Leu Thr Gly His Val Gln Arg Gln Gln Arg Glu
                165                 170                 175

Met Ala Glu Gln Gln Gln Trp Leu Arg Gln Ile Gln Gln Arg Leu His
                180                 185                 190

Thr Ala Ala Leu Pro Ala
        195

<210> SEQ ID NO 11
<211> LENGTH: 10
<212> TYPE: PRT
<213> ORGANISM: Artificial Sequence
<220> FEATURE:
<223> OTHER INFORMATION: Antibodies 1E5, 1E9 and 1A8 VH CDR1 (Exemplary
      and AbM)

<400> SEQUENCE: 11

Gly Tyr Thr Phe Thr Asp Tyr Thr Ile His
1               5                   10

<210> SEQ ID NO 12
<211> LENGTH: 8
<212> TYPE: PRT
<213> ORGANISM: Artificial Sequence
<220> FEATURE:
<223> OTHER INFORMATION: Antibodies 1E5, 1E9 and 1A8 VH CDR1 (IMGT)

<400> SEQUENCE: 12

Gly Tyr Thr Phe Thr Asp Tyr Thr
1               5

<210> SEQ ID NO 13
<211> LENGTH: 5
<212> TYPE: PRT
<213> ORGANISM: Artificial Sequence
<220> FEATURE:
<223> OTHER INFORMATION: Antibodies 1E5, 1E9 and 1A8 VH CDR1 (Kabat)

<400> SEQUENCE: 13

Asp Tyr Thr Ile His
1               5

<210> SEQ ID NO 14
<211> LENGTH: 7
<212> TYPE: PRT
<213> ORGANISM: Artificial Sequence
<220> FEATURE:
<223> OTHER INFORMATION: Antibodies 1E5, 1E9 and 1A8 VH CDR1 (Chothia)

<400> SEQUENCE: 14

Gly Tyr Thr Phe Thr Asp Tyr
1               5

<210> SEQ ID NO 15
<211> LENGTH: 6
<212> TYPE: PRT
<213> ORGANISM: Artificial Sequence
<220> FEATURE:
<223> OTHER INFORMATION: Antibodies 1E5, 1E9 and 1A8 VH CDR1 (Contact)

<400> SEQUENCE: 15

Thr Asp Tyr Thr Ile His

```
<210> SEQ ID NO 16
<211> LENGTH: 17
<212> TYPE: PRT
<213> ORGANISM: Artificial Sequence
<220> FEATURE:
<223> OTHER INFORMATION: Antibody 1E5 VH CDR2 (Exemplary and Kabat)

<400> SEQUENCE: 16

Trp Phe Tyr Pro Gly Ser Asp Asn Ile Lys Tyr Asn Ala Lys Phe Lys
1               5                   10                  15

Asp

<210> SEQ ID NO 17
<211> LENGTH: 8
<212> TYPE: PRT
<213> ORGANISM: Artificial Sequence
<220> FEATURE:
<223> OTHER INFORMATION: Antibodies 1E5, 1E9 and 1A8 VH CDR2 (IMGT)

<400> SEQUENCE: 17

Phe Tyr Pro Gly Ser Asp Asn Ile
1               5

<210> SEQ ID NO 18
<211> LENGTH: 4
<212> TYPE: PRT
<213> ORGANISM: Artificial Sequence
<220> FEATURE:
<223> OTHER INFORMATION: Antibodies 1E5, 1E9 and 1A8 VH CDR2 (Chothia)

<400> SEQUENCE: 18

Pro Gly Ser Asp
1

<210> SEQ ID NO 19
<211> LENGTH: 13
<212> TYPE: PRT
<213> ORGANISM: Artificial Sequence
<220> FEATURE:
<223> OTHER INFORMATION: Antibodies 1E5 and 1E9 VH CDR2 (Contact)

<400> SEQUENCE: 19

Trp Ile Gly Trp Phe Tyr Pro Gly Ser Asp Asn Ile Lys
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Antibodies 1E5, 1E9 and 1A8 VH CDR2 (AbM)

<400> SEQUENCE: 20

Trp Phe Tyr Pro Gly Ser Asp Asn Ile Lys
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Antibody 1E5 VH CDR3 (Exemplary, Kabat and
      AbM)

<400> SEQUENCE: 21
```

-continued

His Glu Ala Phe Ser Tyr Tyr Asp Val Ala Trp Phe Ala Tyr
1               5                   10

<210> SEQ ID NO 22
<211> LENGTH: 16
<212> TYPE: PRT
<213> ORGANISM: Artificial Sequence
<220> FEATURE:
<223> OTHER INFORMATION: Antibody 1E5 VH CDR3 (IMGT)

<400> SEQUENCE: 22

Ala Arg His Glu Ala Phe Ser Tyr Tyr Asp Val Ala Trp Phe Ala Tyr
1               5                   10                  15

<210> SEQ ID NO 23
<211> LENGTH: 12
<212> TYPE: PRT
<213> ORGANISM: Artificial Sequence
<220> FEATURE:
<223> OTHER INFORMATION: Antibodies 1E5 VH CDR3 (Chothia)

<400> SEQUENCE: 23

Glu Ala Phe Ser Tyr Tyr Asp Val Ala Trp Phe Ala
1               5                   10

<210> SEQ ID NO 24
<211> LENGTH: 15
<212> TYPE: PRT
<213> ORGANISM: Artificial Sequence
<220> FEATURE:
<223> OTHER INFORMATION: Antibodies 1E5 VH CDR3 (Contact)

<400> SEQUENCE: 24

Ala Arg His Glu Ala Phe Ser Tyr Tyr Asp Val Ala Trp Phe Ala
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Antibodies 1E5 and 1E9 VL CDR1 (Exemplary,
      Kabat and AbM)

<400> SEQUENCE: 25

Arg Ser Ser Gln Ser Leu Val His Ser Asn Gly Asn Thr Tyr Leu His
1               5                   10                  15

<210> SEQ ID NO 26
<211> LENGTH: 11
<212> TYPE: PRT
<213> ORGANISM: Artificial Sequence
<220> FEATURE:
<223> OTHER INFORMATION: Antibodies 1E5 and 1E9 VL CDR1 (IMGT)

<400> SEQUENCE: 26

Gln Ser Leu Val His Ser Asn Gly Asn Thr Tyr
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Antibodies 1E5 and 1E9 VL CDR1 (Chothia)

<400> SEQUENCE: 27

Ser Gln Ser Leu Val His Ser Asn Gly Asn Thr Tyr
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Antibody 1E5 VL CDR1 (Contact)

<400> SEQUENCE: 28

Val His Ser Asn Gly Asn Thr Tyr Leu His Trp Tyr
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Antibodies 1E5, 1E9 and 1A8 VL CDR2(Exemplary,
      Kabat and AbM)

<400> SEQUENCE: 29

Thr Val Ser Asn Arg Phe Ser
1               5

<210> SEQ ID NO 30
<211> LENGTH: 3
<212> TYPE: PRT
<213> ORGANISM: Artificial Sequence
<220> FEATURE:
<223> OTHER INFORMATION: Antibodies 1E5, 1E9 and 1A8 VL CDR2 (IMGT and
      Chothia)

<400> SEQUENCE: 30

Thr Val Ser
1

<210> SEQ ID NO 31
<211> LENGTH: 10
<212> TYPE: PRT
<213> ORGANISM: Artificial Sequence
<220> FEATURE:
<223> OTHER INFORMATION: Antibodies 1E5, 1E9 and 1A8 VL CDR2 (Contact)

<400> SEQUENCE: 31

Leu Leu Ile Tyr Thr Val Ser Asn Arg Phe
1               5                   10

<210> SEQ ID NO 32
<211> LENGTH: 9
<212> TYPE: PRT
<213> ORGANISM: Artificial Sequence
<220> FEATURE:
<223> OTHER INFORMATION: Antibody 1E5 VL CDR3 (Exemplary, IMGT, Kbat
      and AbM)

<400> SEQUENCE: 32

Ser Gln Thr Thr His Phe Pro Tyr Thr
1               5

<210> SEQ ID NO 33
<211> LENGTH: 6
<212> TYPE: PRT
<213> ORGANISM: Artificial Sequence
<220> FEATURE:
<223> OTHER INFORMATION: Antibody 1E5 VL CDR3 (Chothia)

```
<400> SEQUENCE: 33

Thr Thr His Phe Pro Tyr
1               5

<210> SEQ ID NO 34
<211> LENGTH: 8
<212> TYPE: PRT
<213> ORGANISM: Artificial Sequence
<220> FEATURE:
<223> OTHER INFORMATION: Antibody 1E5 VL CDR3 (Contact)

<400> SEQUENCE: 34

Ser Gln Thr Thr His Phe Pro Tyr
1               5

<210> SEQ ID NO 35
<211> LENGTH: 123
<212> TYPE: PRT
<213> ORGANISM: Artificial Sequence
<220> FEATURE:
<223> OTHER INFORMATION: 1E5 Heavy Chain Variable Region

<400> SEQUENCE: 35

Gln Val Gln Leu Gln Gln Ser Gly Ala Glu Leu Val Lys Pro Gly Thr
1               5                   10                  15

Ser Val Arg Leu Ser Cys Lys Ala Ser Gly Tyr Thr Phe Thr Asp Tyr
            20                  25                  30

Thr Ile His Trp Val Lys Leu Arg Ser Gly Gln Gly Leu Glu Trp Ile
        35                  40                  45

Gly Trp Phe Tyr Pro Gly Ser Asp Asn Ile Lys Tyr Asn Ala Lys Phe
    50                  55                  60

Lys Asp Lys Ala Thr Leu Thr Ala Asp Lys Ser Ser Ser Thr Val Tyr
65                  70                  75                  80

Met Asp Leu Gly Arg Leu Thr Ser Glu Asp Ser Ala Val Tyr Phe Cys
                85                  90                  95

Ala Arg His Glu Ala Phe Ser Tyr Tyr Asp Val Ala Trp Phe Ala Tyr
            100                 105                 110

Trp Gly Gln Gly Thr Leu Val Thr Val Ser Ala
        115                 120

<210> SEQ ID NO 36
<211> LENGTH: 112
<212> TYPE: PRT
<213> ORGANISM: Artificial Sequence
<220> FEATURE:
<223> OTHER INFORMATION: 1E5 Light Chain Variable Region

<400> SEQUENCE: 36

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Thr Val Ser Asn Arg Phe Ser Gly Val Pro
    50                  55                  60

Asp Arg Phe Ser Gly Ser Gly Ser Gly Ser Asp Phe Thr Leu Asn Phe
65                  70                  75                  80

Ser Arg Val Glu Ala Glu Asp Leu Gly Val Tyr Phe Cys Ser Gln Thr
```

```
                    85                  90                  95
Thr His Phe Pro Tyr Thr Phe Gly Gly Gly Thr Lys Leu Glu Ile Lys
                    100                 105                 110

<210> SEQ ID NO 37
<211> LENGTH: 17
<212> TYPE: PRT
<213> ORGANISM: Artificial Sequence
<220> FEATURE:
<223> OTHER INFORMATION: Antibody 1E9 VH CDR2 (Exemplary and Kabat)

<400> SEQUENCE: 37

Trp Phe Tyr Pro Gly Ser Asp Asn Ile Lys Phe Asn Ala Lys Phe Arg
1               5                   10                  15
Asp

<210> SEQ ID NO 38
<211> LENGTH: 14
<212> TYPE: PRT
<213> ORGANISM: Artificial Sequence
<220> FEATURE:
<223> OTHER INFORMATION: Antibody 1E9 VH CDR3 (Exemplary, Kabat and
      AbM)

<400> SEQUENCE: 38

His Glu Ala Phe Tyr Val Tyr Asp Val Ala Trp Phe Ala Asn
1               5                   10

<210> SEQ ID NO 39
<211> LENGTH: 16
<212> TYPE: PRT
<213> ORGANISM: Artificial Sequence
<220> FEATURE:
<223> OTHER INFORMATION: Antibody 1E9 VH CDR3 (IMGT)

<400> SEQUENCE: 39

Ala Arg His Glu Ala Phe Tyr Val Tyr Asp Val Ala Trp Phe Ala Asn
1               5                   10                  15

<210> SEQ ID NO 40
<211> LENGTH: 12
<212> TYPE: PRT
<213> ORGANISM: Artificial Sequence
<220> FEATURE:
<223> OTHER INFORMATION: Antibody 1E9 VL CDR1 (Contact)

<400> SEQUENCE: 40

Val His Ser Asn Gly Asn Thr Tyr Leu His Trp Phe
1               5                   10

<210> SEQ ID NO 41
<211> LENGTH: 9
<212> TYPE: PRT
<213> ORGANISM: Artificial Sequence
<220> FEATURE:
<223> OTHER INFORMATION: Antibodies 1E9 and 1A8 VL CDR3 (Exemplary,
      IMGT, Kabat and AbM)

<400> SEQUENCE: 41

Ser Gln Ser Thr His Phe Pro Tyr Thr
1               5

<210> SEQ ID NO 42
<211> LENGTH: 6
<212> TYPE: PRT
<213> ORGANISM: Artificial Sequence
```

```
<220> FEATURE:
<223> OTHER INFORMATION: Antibodies 1E9 and 1A8 VL CDR3 (Chothia)

<400> SEQUENCE: 42

Ser Thr His Phe Pro Tyr
1               5

<210> SEQ ID NO 43
<211> LENGTH: 8
<212> TYPE: PRT
<213> ORGANISM: Artificial Sequence
<220> FEATURE:
<223> OTHER INFORMATION: Antibodies 1E9 and 1A8 VL CDR3 (Contact)

<400> SEQUENCE: 43

Ser Gln Ser Thr His Phe Pro Tyr
1               5

<210> SEQ ID NO 44
<211> LENGTH: 123
<212> TYPE: PRT
<213> ORGANISM: Artificial Sequence
<220> FEATURE:
<223> OTHER INFORMATION: 1E9 Heavy chain variable region

<400> SEQUENCE: 44

Gln Val Gln Leu Gln Gln Ser Gly Thr Glu Leu Val Lys Pro Gly Ala
1               5                   10                  15

Ser Val Lys Leu Ser Cys Lys Ala Ser Gly Tyr Thr Phe Thr Asp Tyr
                20                  25                  30

Thr Ile His Trp Val Lys Gln Arg Ser Gly Gln Gly Leu Glu Trp Ile
            35                  40                  45

Gly Trp Phe Tyr Pro Gly Ser Asp Asn Ile Lys Phe Asn Ala Lys Phe
        50                  55                  60

Arg Asp Lys Ala Thr Leu Thr Ala Asp Lys Ser Ser Ser Thr Val Tyr
65                  70                  75                  80

Met Glu Leu Ser Arg Leu Thr Ser Glu Asp Ser Ala Val Tyr Phe Cys
                85                  90                  95

Ala Arg His Glu Ala Phe Tyr Val Tyr Asp Val Ala Trp Phe Ala Asn
            100                 105                 110

Trp Gly Gln Gly Thr Leu Val Thr Val Ser Thr
        115                 120

<210> SEQ ID NO 45
<211> LENGTH: 112
<212> TYPE: PRT
<213> ORGANISM: Artificial Sequence
<220> FEATURE:
<223> OTHER INFORMATION: 1E9 Light chain variable region

<400> SEQUENCE: 45

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Tyr Leu His Trp Phe Leu Gln Lys Pro Gly Gln Ser
            35                  40                  45

Pro Asn Leu Leu Ile Tyr Thr Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80
```

Ser Arg Val Glu Ala Gly Asp Leu Gly Val Tyr Phe Cys Ser Gln Ser
            85                  90                  95

Thr His Phe Pro Tyr Thr Phe Gly Gly Thr Lys Leu Glu Ile Lys
            100                 105                 110

<210> SEQ ID NO 46
<211> LENGTH: 17
<212> TYPE: PRT
<213> ORGANISM: Artificial Sequence
<220> FEATURE:
<223> OTHER INFORMATION: Antibody 1A8 VH CDR2 (Exemplary and Kabat)

<400> SEQUENCE: 46

Trp Phe Tyr Pro Gly Ser Asp Asn Ile Lys Tyr Asn Glu Lys Phe Lys
1               5                   10                  15

Asp

<210> SEQ ID NO 47
<211> LENGTH: 20
<212> TYPE: PRT
<213> ORGANISM: Artificial Sequence
<220> FEATURE:
<223> OTHER INFORMATION: Antibody 1A8 VH CDR2 (Contact)

<400> SEQUENCE: 47

Trp Ile Gly Trp Phe Tyr Pro Gly Ser Asp Asn Ile Lys Tyr Asn Glu
1               5                   10                  15

Lys Phe Lys Asp
            20

<210> SEQ ID NO 48
<211> LENGTH: 14
<212> TYPE: PRT
<213> ORGANISM: Artificial Sequence
<220> FEATURE:
<223> OTHER INFORMATION: Antibody 1A8 VH CDR3 (Exemplary, Kabat and
      AbM)

<400> SEQUENCE: 48

His Glu Ala Tyr Tyr Val Tyr Asp Val Ala Trp Phe Ala Tyr
1               5                   10

<210> SEQ ID NO 49
<211> LENGTH: 16
<212> TYPE: PRT
<213> ORGANISM: Artificial Sequence
<220> FEATURE:
<223> OTHER INFORMATION: Antibody 1A8 VH CDR3 (IMGT)

<400> SEQUENCE: 49

Ala Arg His Glu Ala Tyr Tyr Val Tyr Asp Val Ala Trp Phe Ala Tyr
1               5                   10                  15

<210> SEQ ID NO 50
<211> LENGTH: 12
<212> TYPE: PRT
<213> ORGANISM: Artificial Sequence
<220> FEATURE:
<223> OTHER INFORMATION: Antibody 1A8 VH CDR3 (Chothia)

<400> SEQUENCE: 50

Glu Ala Tyr Tyr Val Tyr Asp Val Ala Trp Phe Ala
1               5                   10

```
<210> SEQ ID NO 51
<211> LENGTH: 15
<212> TYPE: PRT
<213> ORGANISM: Artificial Sequence
<220> FEATURE:
<223> OTHER INFORMATION: Antibody 1A8 VH CDR3 (Contact)

<400> SEQUENCE: 51

Ala Arg His Glu Ala Tyr Tyr Val Tyr Asp Val Ala Trp Phe Ala
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: Antibody 1A8 VL CDR1 (Exemplary, Kabat and
      AbM)

<400> SEQUENCE: 52

Ser Ser Ser Gln Ser Leu Val His Ser Asn Gly Asn Thr Phe Leu His
1               5                   10                  15

<210> SEQ ID NO 53
<211> LENGTH: 11
<212> TYPE: PRT
<213> ORGANISM: Artificial Sequence
<220> FEATURE:
<223> OTHER INFORMATION: Antibody 1A8 VL CDR1 (IMGT)

<400> SEQUENCE: 53

Gln Ser Leu Val His Ser Asn Gly Asn Thr Phe
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Antibody 1A8 VL CDR1 (Chothia)

<400> SEQUENCE: 54

Ser Gln Ser Leu Val His Ser Asn Gly Asn Thr Phe
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Antibody 1A8 VL CDR1 (Contact)

<400> SEQUENCE: 55

Val His Ser Asn Gly Asn Thr Phe Leu His Trp Phe
1               5                   10

<210> SEQ ID NO 56
<211> LENGTH: 123
<212> TYPE: PRT
<213> ORGANISM: Artificial Sequence
<220> FEATURE:
<223> OTHER INFORMATION: 1A8 Heavy chain variable region

<400> SEQUENCE: 56

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Asp Tyr
```

```
                    20                  25                  30
Thr Ile His Trp Val Lys Gln Arg Ser Gly Gln Gly Leu Glu Trp Ile
                35                  40                  45
Gly Trp Phe Tyr Pro Gly Ser Asp Asn Ile Lys Tyr Asn Glu Lys Phe
        50                  55                  60
Lys Asp Lys Ala Thr Leu Thr Ala Asp Lys Ser Ser Ile Val Tyr
65                  70                  75                  80
Met Glu Leu Ser Arg Leu Thr Ser Glu Asp Ser Ala Val Tyr Phe Cys
                85                  90                  95
Ala Arg His Glu Ala Tyr Tyr Val Tyr Asp Val Ala Trp Phe Ala Tyr
                100                 105                 110
Trp Gly Gln Gly Thr Leu Val Thr Val Ser Ala
            115                 120

<210> SEQ ID NO 57
<211> LENGTH: 112
<212> TYPE: PRT
<213> ORGANISM: Artificial Sequence
<220> FEATURE:
<223> OTHER INFORMATION: 1A8 Light chain variable region

<400> SEQUENCE: 57

Asp Val Val Met Thr Gln Thr Pro Leu Ser Leu Pro Val Ser Leu Gly
1               5                   10                  15
Asp Gln Ala Ser Ile Ser Cys Ser Ser Ser Gln Ser Leu Val His Ser
                20                  25                  30
Asn Gly Asn Thr Phe Leu His Trp Phe Leu Gln Arg Pro Gly Gln Ser
            35                  40                  45
Pro Lys Leu Leu Ile Tyr Thr Val Ser Asn Arg Phe Ser Gly Val Pro
        50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Phe Cys Ser Gln Ser
                85                  90                  95
Thr His Phe Pro Tyr Thr Phe Gly Gly Gly Thr Thr Leu Glu Ile Lys
                100                 105                 110

<210> SEQ ID NO 58
<211> LENGTH: 17
<212> TYPE: PRT
<213> ORGANISM: Artificial Sequence
<220> FEATURE:
<223> OTHER INFORMATION: Heavy Chain CDR2 consensus sequence
<220> FEATURE:
<221> NAME/KEY: misc_feature
<222> LOCATION: (11)..(11)
<223> OTHER INFORMATION: Xaa = Tyr or Phe
<220> FEATURE:
<221> NAME/KEY: misc_feature
<222> LOCATION: (13)..(13)
<223> OTHER INFORMATION: Xaa = Ala or Glu
<220> FEATURE:
<221> NAME/KEY: misc_feature
<222> LOCATION: (16)..(16)
<223> OTHER INFORMATION: Xaa = Lys or Arg

<400> SEQUENCE: 58

Trp Phe Tyr Pro Gly Ser Asp Asn Ile Lys Xaa Asn Xaa Lys Phe Xaa
1               5                   10                  15
Asp
```

```
<210> SEQ ID NO 59
<211> LENGTH: 14
<212> TYPE: PRT
<213> ORGANISM: Artificial Sequence
<220> FEATURE:
<223> OTHER INFORMATION: Heavy chain CDR3 consensus sequence
<220> FEATURE:
<221> NAME/KEY: misc_feature
<222> LOCATION: (4)..(4)
<223> OTHER INFORMATION: Xaa = Tyr or Phe
<220> FEATURE:
<221> NAME/KEY: misc_feature
<222> LOCATION: (5)..(5)
<223> OTHER INFORMATION: Xaa = Ser or Tyr
<220> FEATURE:
<221> NAME/KEY: misc_feature
<222> LOCATION: (6)..(6)
<223> OTHER INFORMATION: Xaa = Tyr or Val
<220> FEATURE:
<221> NAME/KEY: misc_feature
<222> LOCATION: (14)..(14)
<223> OTHER INFORMATION: Xaa =  Tyr or Asn

<400> SEQUENCE: 59

His Glu Ala Xaa Xaa Xaa Tyr Asp Val Ala Trp Phe Ala Xaa
1               5                   10

<210> SEQ ID NO 60
<211> LENGTH: 16
<212> TYPE: PRT
<213> ORGANISM: Artificial Sequence
<220> FEATURE:
<223> OTHER INFORMATION: Light chain CDR1 consensus sequence
<220> FEATURE:
<221> NAME/KEY: misc_feature
<222> LOCATION: (1)..(1)
<223> OTHER INFORMATION: Xaa = Arg or Ser
<220> FEATURE:
<221> NAME/KEY: misc_feature
<222> LOCATION: (14)..(14)
<223> OTHER INFORMATION: Xaa = Tyr or Phe

<400> SEQUENCE: 60

Xaa Ser Ser Gln Ser Leu Val His Ser Asn Gly Asn Thr Xaa Leu His
1               5                   10                  15

<210> SEQ ID NO 61
<211> LENGTH: 9
<212> TYPE: PRT
<213> ORGANISM: Artificial Sequence
<220> FEATURE:
<223> OTHER INFORMATION: Light chain CDR3 consensus sequence
<220> FEATURE:
<221> NAME/KEY: misc_feature
<222> LOCATION: (3)..(3)
<223> OTHER INFORMATION: Xaa = Thr or Ser

<400> SEQUENCE: 61

Ser Gln Xaa Thr His Phe Pro Tyr Thr
1               5

<210> SEQ ID NO 62
<211> LENGTH: 123
<212> TYPE: PRT
<213> ORGANISM: Artificial Sequence
<220> FEATURE:
<223> OTHER INFORMATION: Hz1E5.A1 Heavy chain variable region

<400> SEQUENCE: 62

Glu Val Gln Leu Val Gln Ser Gly Ala Glu Val Lys Lys Pro Gly Ser
1               5                   10                  15
```

Ser Val Lys Val Ser Cys Lys Ala Ser Gly Tyr Thr Phe Thr Asp Tyr
            20                  25                  30

Thr Ile His Trp Val Arg Gln Ala Pro Gly Gln Gly Leu Glu Trp Met
        35                  40                  45

Gly Trp Phe Tyr Pro Gly Ser Asp Asn Ile Lys Tyr Asn Ala Lys Phe
    50                  55                  60

Lys Asp Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Glu Ala Phe Ser Tyr Tyr Asp Val Ala Trp Phe Ala Tyr
            100                 105                 110

Trp Gly Gln Gly Thr Leu Val Thr Val Ser Ser
            115                 120

<210> SEQ ID NO 63
<211> LENGTH: 112
<212> TYPE: PRT
<213> ORGANISM: Artificial Sequence
<220> FEATURE:
<223> OTHER INFORMATION: Hz1E5.A1 Light chain variable region

<400> SEQUENCE: 63

Asp Val Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Asp Phe Thr Leu Lys Ile
65                  70                  75                  80

Ser Arg Val Glu Ala Glu Asp Val Gly Val Tyr Phe Cys Ser Gln Thr
                85                  90                  95

Thr His Phe Pro Tyr Thr Phe Gly Gln Gly Thr Lys Val Glu Ile Lys
            100                 105                 110

<210> SEQ ID NO 64
<211> LENGTH: 453
<212> TYPE: PRT
<213> ORGANISM: Artificial Sequence
<220> FEATURE:
<223> OTHER INFORMATION: Hz1E5.A1 Heavy chain without signal sequence

<400> SEQUENCE: 64

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Thr Ile His Trp Val Arg Gln Ala Pro Gly Gln Gly Leu Glu Trp Met
        35                  40                  45

Gly Trp Phe Tyr Pro Gly Ser Asp Asn Ile Lys Tyr Asn Ala Lys Phe
    50                  55                  60

Lys Asp Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Glu Ala Phe Ser Tyr Tyr Asp Val Ala Trp Phe Ala Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
    450

<210> SEQ ID NO 65
<211> LENGTH: 219
<212> TYPE: PRT
<213> ORGANISM: Artificial Sequence
<220> FEATURE:
<223> OTHER INFORMATION: Hz1E5.A1 Light chain without signal sequence

<400> SEQUENCE: 65

```
Asp Val Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Asp Phe Thr Leu Lys Ile
65                  70                  75                  80

Ser Arg Val Glu Ala Glu Asp Val Gly Val Tyr Phe Cys Ser Gln Thr
                85                  90                  95

Thr His Phe Pro Tyr Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 66
<211> LENGTH: 8
<212> TYPE: PRT
<213> ORGANISM: Artificial Sequence
<220> FEATURE:
<223> OTHER INFORMATION: FLAG tag

<400> SEQUENCE: 66

```
Asp Tyr Lys Asp Asp Asp Asp Lys
1               5
```

<210> SEQ ID NO 67
<211> LENGTH: 36
<212> TYPE: PRT
<213> ORGANISM: Artificial Sequence
<220> FEATURE:
<223> OTHER INFORMATION: Cyno ANGPLT8 amino acids 25-60 (cSE1 peptide)

<400> SEQUENCE: 67

```
Gly Ser Pro Glu Leu Ala Glu His Glu Glu Leu Thr Leu Leu Phe His
1               5                   10                  15

Gly Thr Leu Gln Leu Gly Gln Ala Leu Asn Gly Val Tyr Lys Thr Thr
            20                  25                  30

Glu Gly Arg Leu
        35
```

<210> SEQ ID NO 68
<211> LENGTH: 12
<212> TYPE: PRT

```
<213> ORGANISM: Artificial Sequence
<220> FEATURE:
<223> OTHER INFORMATION: Antibodies 1E9 VH CDR3 (Chothia)

<400> SEQUENCE: 68

Glu Ala Phe Tyr Val Tyr Asp Val Ala Trp Phe Ala
1               5                   10

<210> SEQ ID NO 69
<211> LENGTH: 15
<212> TYPE: PRT
<213> ORGANISM: Artificial Sequence
<220> FEATURE:
<223> OTHER INFORMATION: Antibodies 1E9 VH CDR3 (Contact)

<400> SEQUENCE: 69

Ala Arg His Glu Ala Phe Tyr Val Tyr Asp Val Ala Trp Phe Ala
1               5                   10                  15
```